US012558406B2

(12) United States Patent
Kang et al.

(10) Patent No.: US 12,558,406 B2
(45) Date of Patent: Feb. 24, 2026

(54) ANTI-TIGIT ANTIBODIES AND USE THEREOF

(71) Applicant: MediMabBio Inc., Seongnam-si (KR)

(72) Inventors: Yuhoi Kang, Seongnam-si (KR); Hongseok Jo, Hwaseong-si (KR)

(73) Assignee: MEDIMABBIO INC., Seongnam-si (KR)

( * ) Notice: Subject to any disclaimer, the term of this patent is extended or adjusted under 35 U.S.C. 154(b) by 0 days.

(21) Appl. No.: 18/290,171

(22) PCT Filed: May 10, 2022

(86) PCT No.: PCT/KR2022/006695
§ 371 (c)(1),
(2) Date: Sep. 25, 2024

(87) PCT Pub. No.: WO2022/240159
PCT Pub. Date: Nov. 17, 2022

(65) Prior Publication Data
US 2025/0064909 A1     Feb. 27, 2025

(30) Foreign Application Priority Data
May 10, 2021     (KR) ........................ 10-2021-0060014

(51) Int. Cl.
A61K 39/00     (2006.01)
A61P 35/00     (2006.01)
C07K 16/28     (2006.01)

(52) U.S. Cl.
CPC ....... *A61K 39/00* (2013.01); *A61K 39/001111* (2018.08); *A61P 35/00* (2018.01); *C07K 16/2803* (2013.01); *C07K 16/2818* (2013.01); *A61K 2039/507* (2013.01); *C07K 2317/24* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 2016/0176963 A1 | 6/2016 | Maurer et al. |
| 2016/0376365 A1 | 12/2016 | Gurney et al. |
| 2019/0100591 A1 | 4/2019 | Cooper et al. |
| 2021/0040201 A1 | 2/2021 | Shi et al. |
| 2021/0054071 A1 | 2/2021 | Zhang et al. |
| 2021/0087266 A1 | 3/2021 | Chou et al. |

FOREIGN PATENT DOCUMENTS

| | | | | |
|---|---|---|---|---|
| CN | 107207594 | 9/2017 | | |
| CN | 108290936 | 7/2018 | | |
| CN | 109384846 | 2/2019 | | |
| CN | 111526888 | 8/2020 | | |
| JP | 2013-531982 | 8/2013 | | |
| JP | 2018-532383 | 11/2018 | | |
| JP | 2019-513817 | 5/2019 | | |
| KR | 10-2017-0041272 | 4/2017 | | |
| KR | 10-2018-0014050 | 2/2018 | | |
| KR | 10-2018-0119653 | 11/2018 | | |
| KR | 10-2020-0105849 | 9/2020 | | |
| KR | 10-2020-0143250 | 12/2020 | | |
| WO | 2016-028656 | 2/2016 | | |
| WO | 2017-053748 | 3/2017 | | |
| WO | 2017-152088 | 9/2017 | | |
| WO | WO2018220446 A1 * | 12/2018 | ......... | C07K 16/3061 |
| WO | 2019-129261 | 7/2019 | | |

OTHER PUBLICATIONS

EPO, Supplementary European Search Report of the corresponding European Patent Application No. 22807807.7, dated Jun. 25, 2024, total 8 pages.
JPO, Office Action of JP 2023-569839 dated Apr. 23, 2024.
KIPO, PCT Search Report & Written Opinion of PCT/KR2022/006695 dated Aug. 17, 2022, total 15 pages.
EPO, Office Action of EP 22807807.7 dated Feb. 7, 2025, total 6 pages.
Yini Sun et al., "Anti-TIGIT differentially affects sepsis survival in immunologically experienced versus previously naive hosts", JCI Insight. 2021;6(5):e141245, Mar. 8, 2021, total 16 pages.
Cristina Caldas et al., "Humanization of the anti-CD18 antibody 6.7: an unexpected effect of a framework residue in binding to antigen", Molecular Immunology, vol. 39, No. 15, May 1, 2003, pp. 941-952.
EPO, Office Action of EP 22807807.7 dated Jul. 23, 2025, total 8 pages.
Mathieu Dondelinger et al., "Understanding the Significance and Implications of Antibody Numbering and Antigen-Binding Surface/Residue Definition", Front. Immunol., vol. 9, Article 2278, Oct. 16, 2018, total 15 pages.

* cited by examiner

*Primary Examiner* — Peter J Reddig
*Assistant Examiner* — Estella M. Gustilo
(74) *Attorney, Agent, or Firm* — LEX IP MEISTER, PLLC

(57) ABSTRACT

The present invention relates to: novel anti-TIGIT antibodies; and uses thereof for increasing immunity, anticancer treatments, and preventing and/or treating immunological diseases.

20 Claims, 50 Drawing Sheets
Specification includes a Sequence Listing.

[Fig. 1]
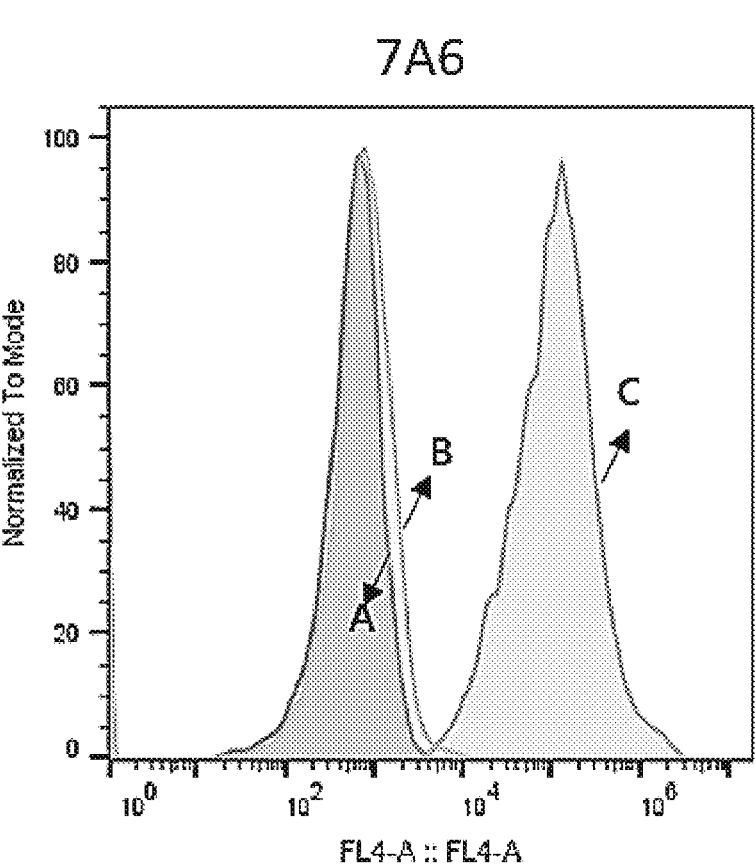
7A6
A ☐ CHO-K1 + 5.0 μg/mL antibody
B ☐ CHO-K1 TIGIT + 5.0 μg/mL antibody
C ☐ Background

[Fig. 2]

Alignment of Chimeric and Humanized Variable Domain Sequences

Heavy chain

|  | SEQ NO. | | 10 | 20 | 30 | CDR-1 35A | 40 | CDR-2 50 |
|---|---|---|---|---|---|---|---|---|
| 7A6_VH0 | 9 | DVQLQESGPGLVKPSQSLSLTCTVTGYSI | TSDYAWNWI | RQFPGNKLEWMGYI | SYSGSARY |
| 7A6_VH1 | 10 | DVQLQESGPGLVKPSQTLSLTCTVTGYSI | TSDYAWNWI | RQPPGKGLEWMGYI | SYSGSARY |
| 7A6_VH2 | 11 | DVQLQESGPGLVKPSQTLSLTCTVTGYSI | TSDYAWNWI | RQPPGKGLEWMGYI | SYSGSARY |
| 7A6_VH3 | 12 | QVQLQESGPGLVKPSQTLSLTCTVTGYSI | TSDYAWNWI | RQPPGKGLEWMGYI | SYSGSARY |
| 7A6_VH4 | 13 | QVQLQESGPGLVKPSQTLSLTCTVTGYSI | TSDYAWNWI | RQPPGKGLEWMGYI | SYSGSARY |
| 7A6_VH5 | 14 | QVQLQESGPGLVKPSQTLSLTCTVTGYSI | TSDYAWNWI | RQPPGKGLEWMGYI | SYSGSARY |

|  | 60 | 70 | 80  82ABC | 90 | CDR-3 100 A | 110  113 |
|---|---|---|---|---|---|---|
| 7A6_VH0 | NPSLKSRISI | TRDTSMNQFFLQLNSVTAEDTATYYCARKGYPAYFAYWGQGTLVTVSS |
| 7A6_VH1 | NPSLKSRITI | SRDTSMNQFSLKLNSVTAEDTATYYCARKGYPAYFAYWGQGTLVTVSS |
| 7A6_VH2 | NPSLKSRITI | SRDTSKNQFSLKLSSVTAEDTATYYCARKGYPAYFAYWGQGTLVTVSS |
| 7A6_VH3 | NPSLKSRVTI | SRDTSKNQFSLKLSSVTAEDTATYYCARKGYPAYFAYWGQGTLVTVSS |
| 7A6_VH4 | NPSLKSRVTI | SRDTSKNQFSLKLSSVTAADTAVYYCARKGYPAYFAYWGQGTLVTVSS |
| 7A6_VH5 | NPSLKSRVTI | SVDTSKNQFSLKLSSVTAADTAVYYCARKGYPAYFAYWGQGTLVTVSS |

[Fig. 21 _continued
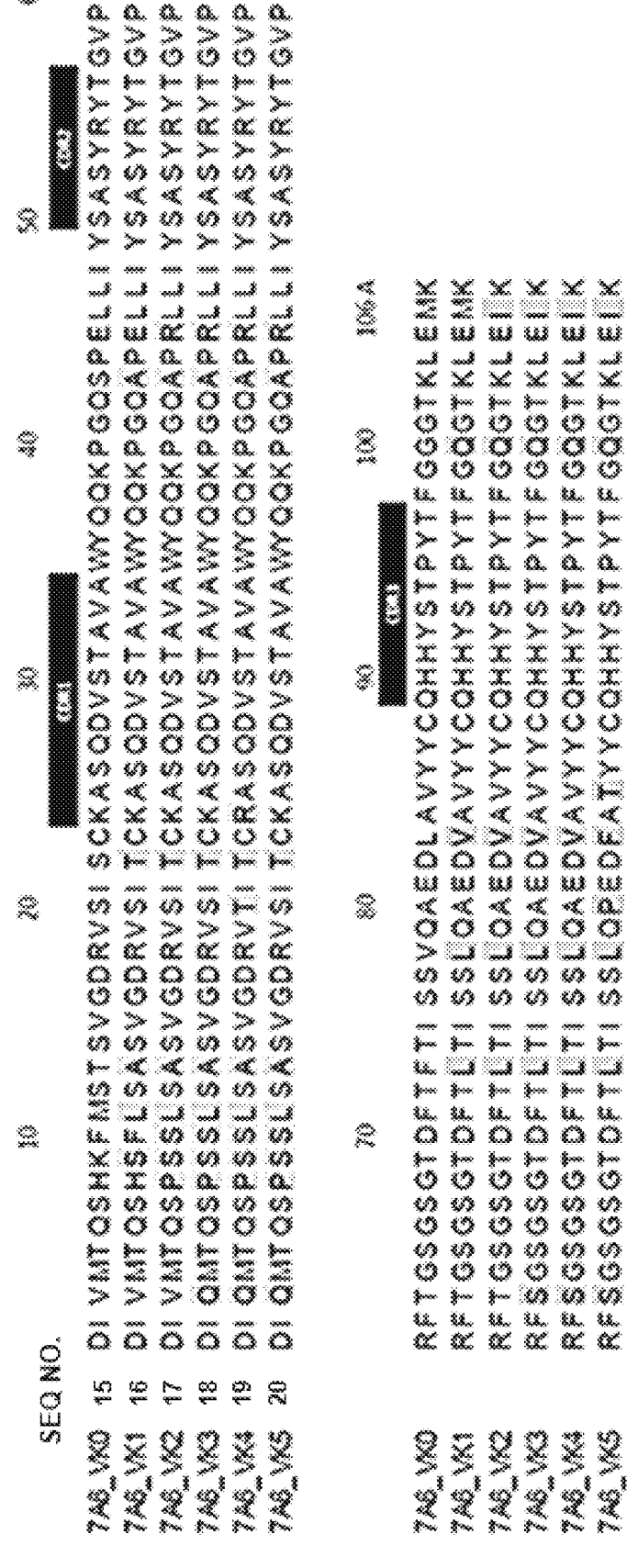
Light chain

[Fig. 3a]
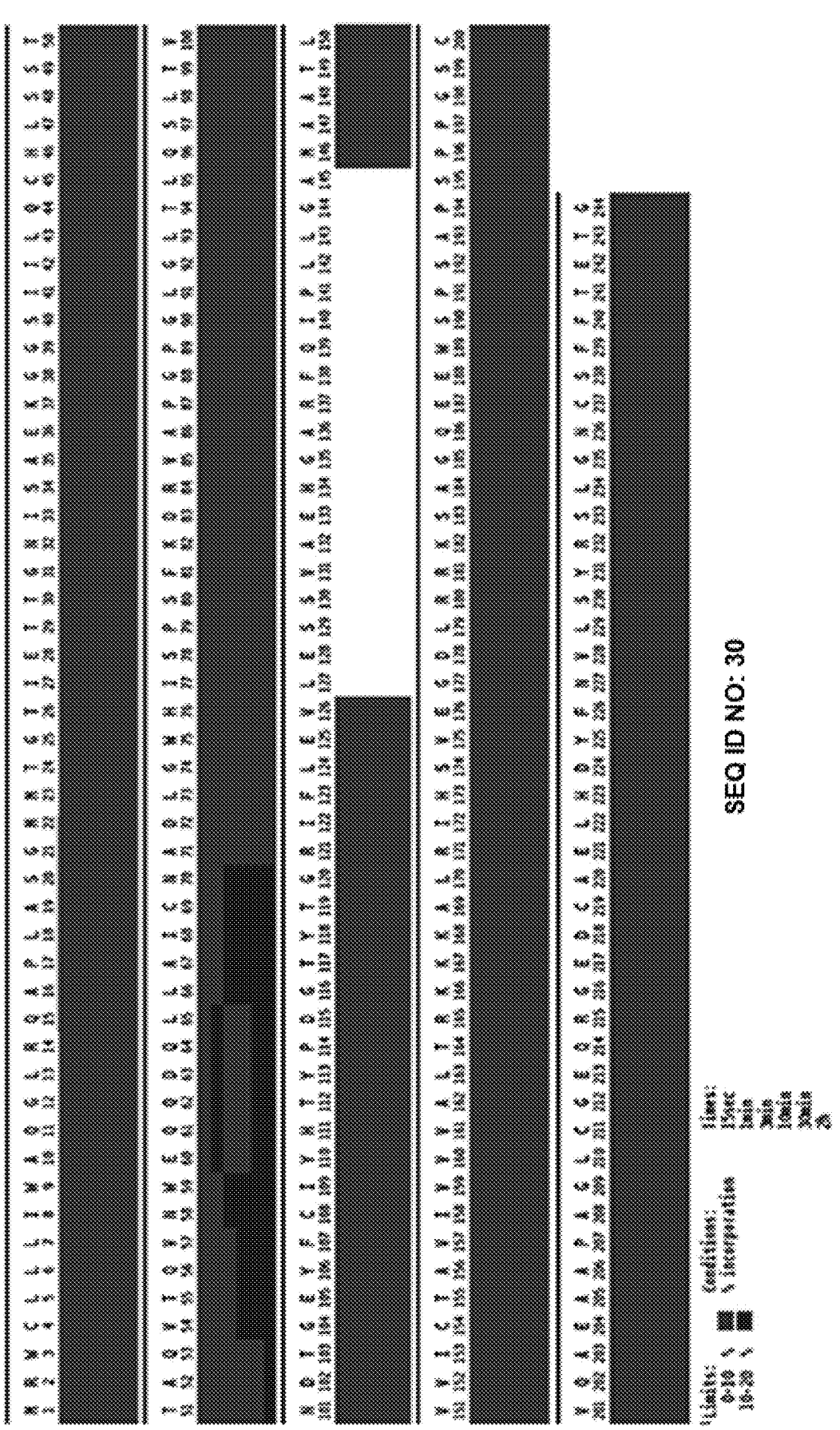
SEQ ID NO: 30

〖Fig. 3b〗
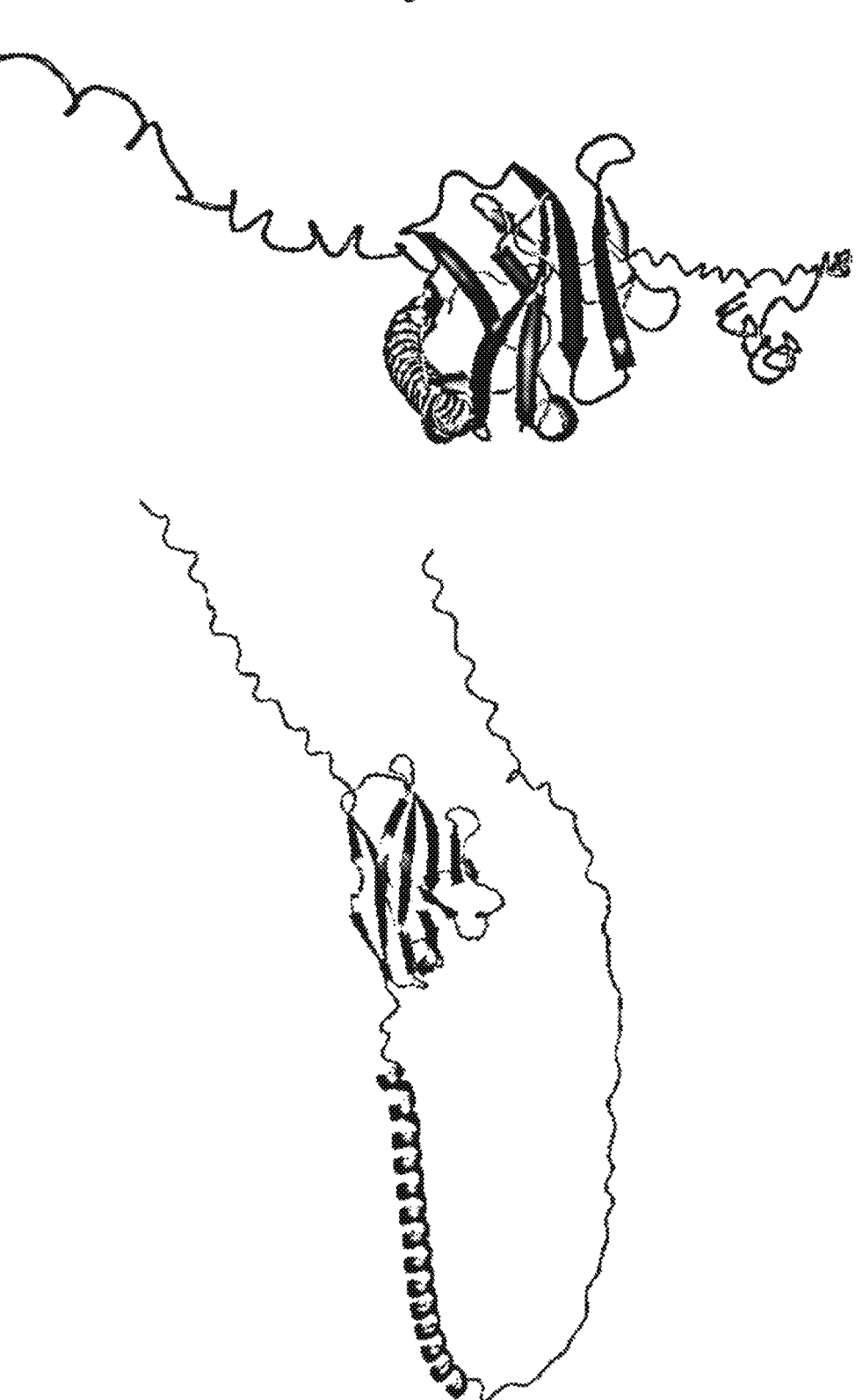

[Fig. 4]
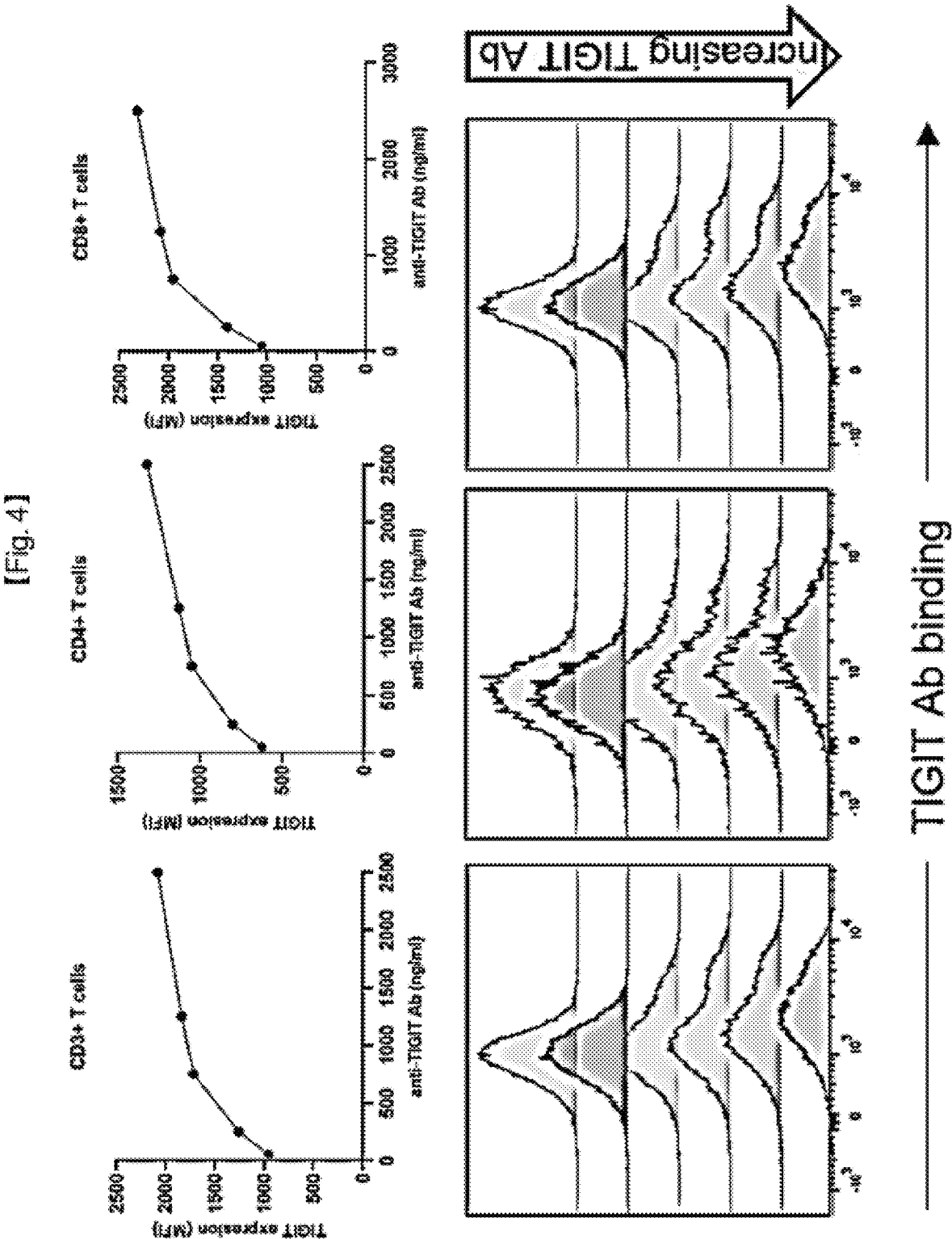

【Fig. 5】
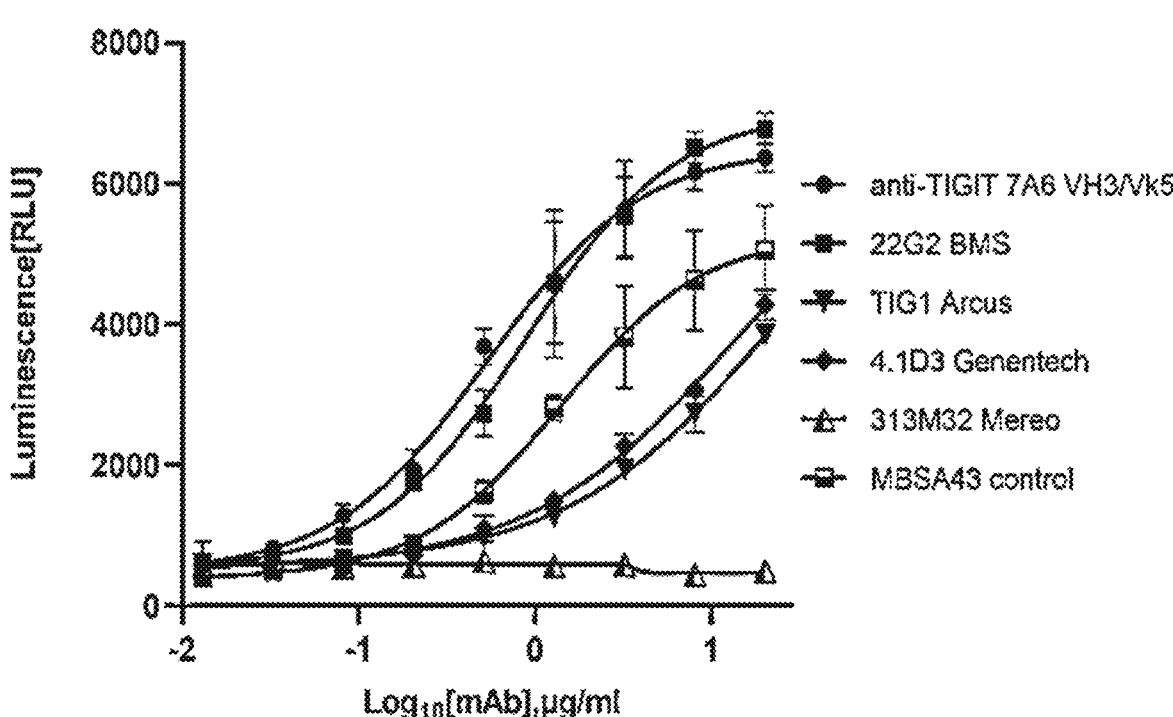
| ID | EC50 |
|---|---|
| anti-TIGIT 7A6VH3/Vk5 | 0.5209 |
| 22G2 BMS | 0.8034 |
| TIG1 Arcus | 3.739 |
| 4.1D3 Genentech | 3.274 |
| MBSA43 control | 1.235 |
| 313M32 Mereo | - |

【Fig. 6】
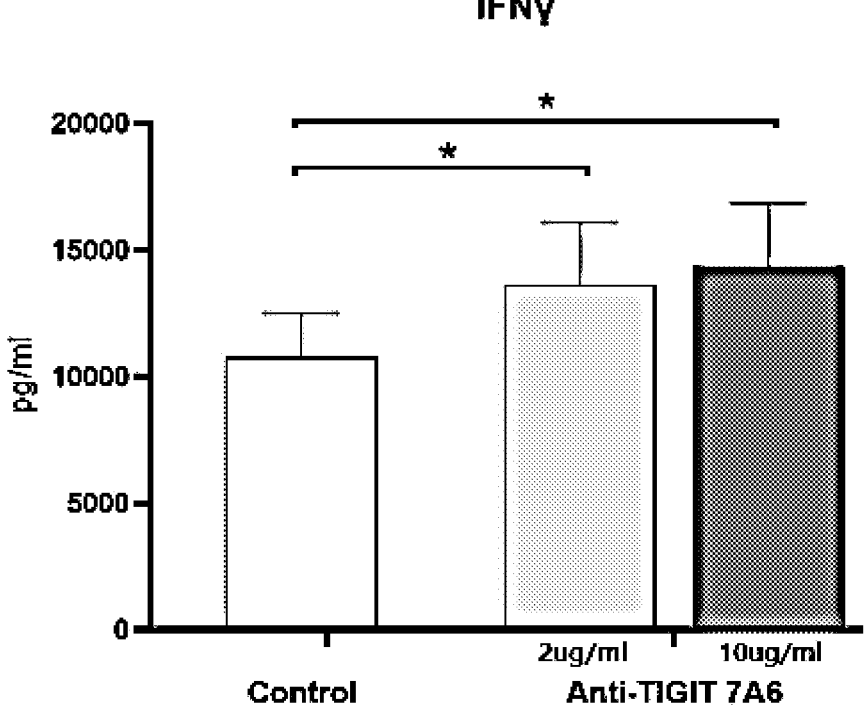

【Fig. 7a】
CD4+ T cells
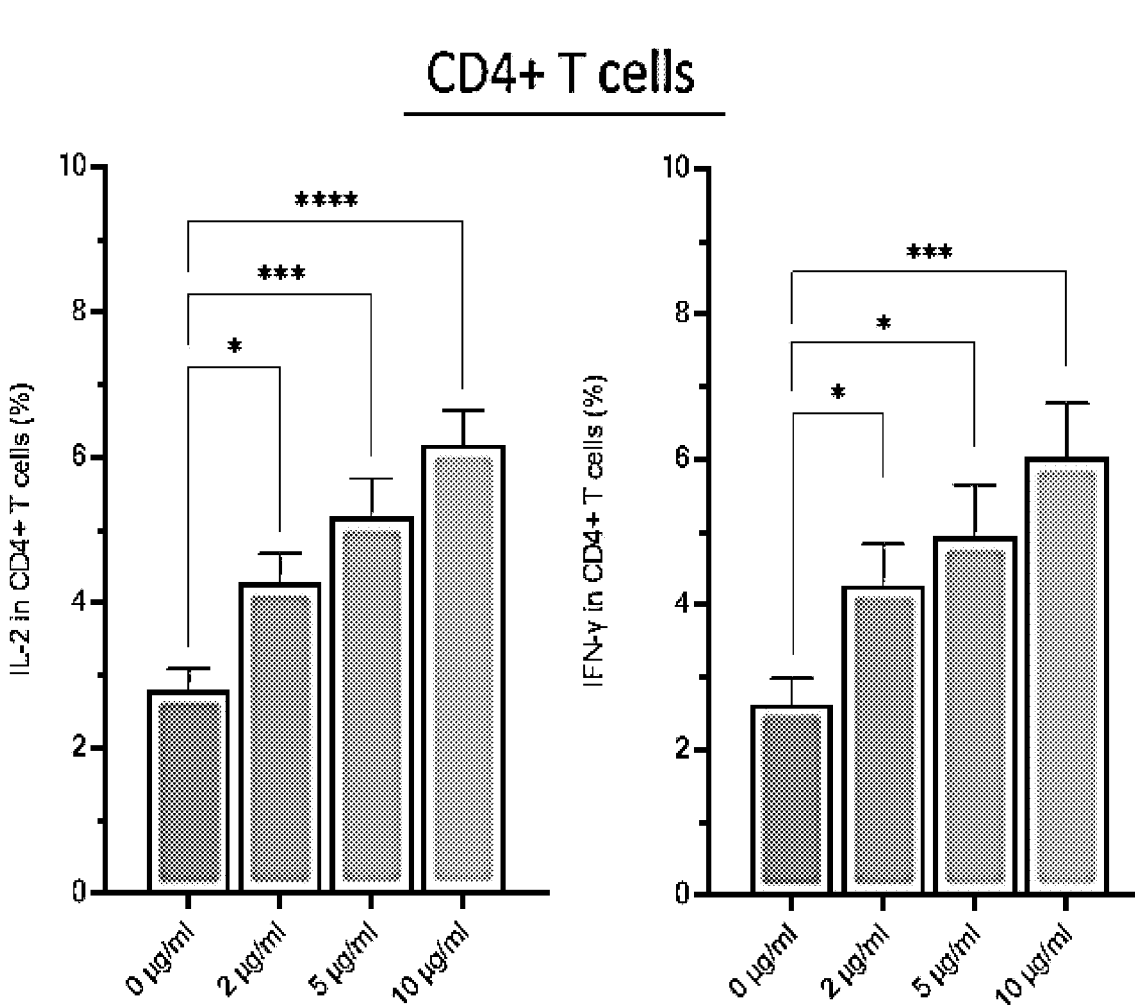

【Fig. 7b】
CD8+ T cells
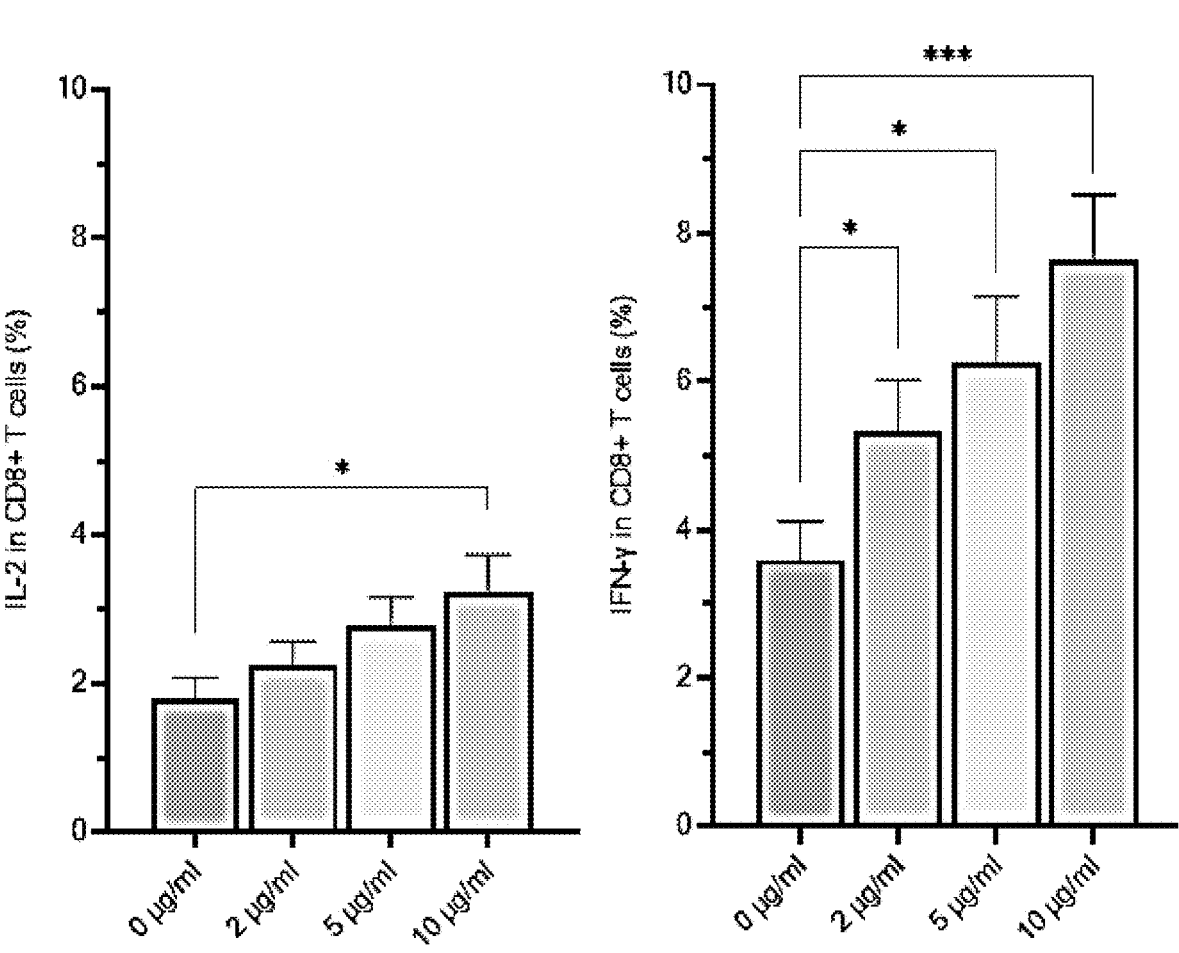

【Fig. 8a】
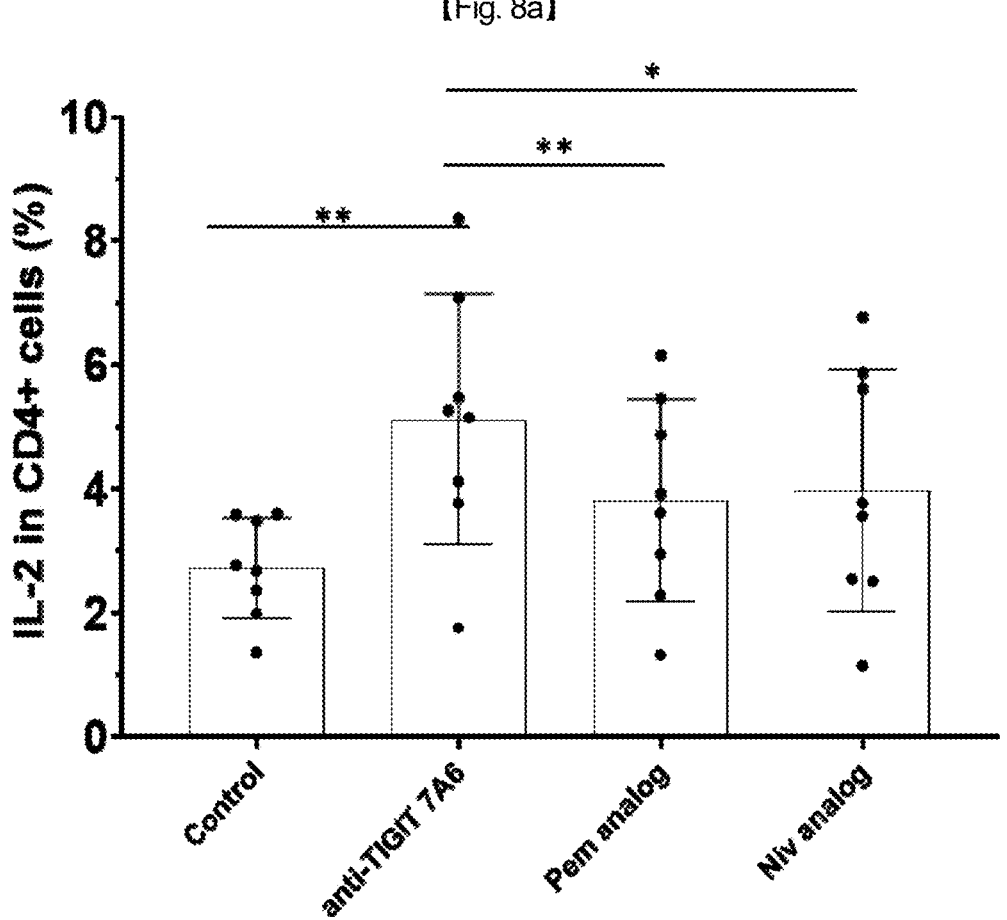

【Fig. 8b】
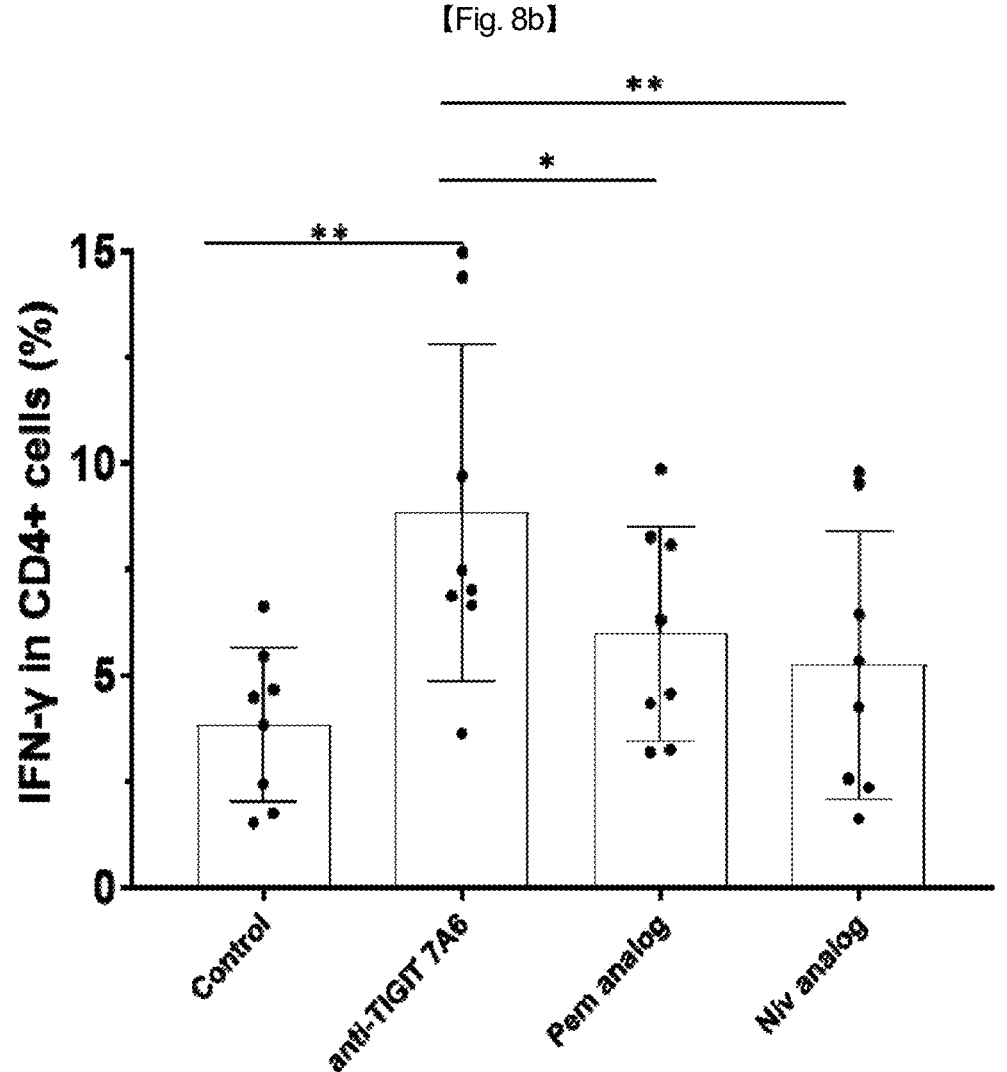

【Fig. 8c】
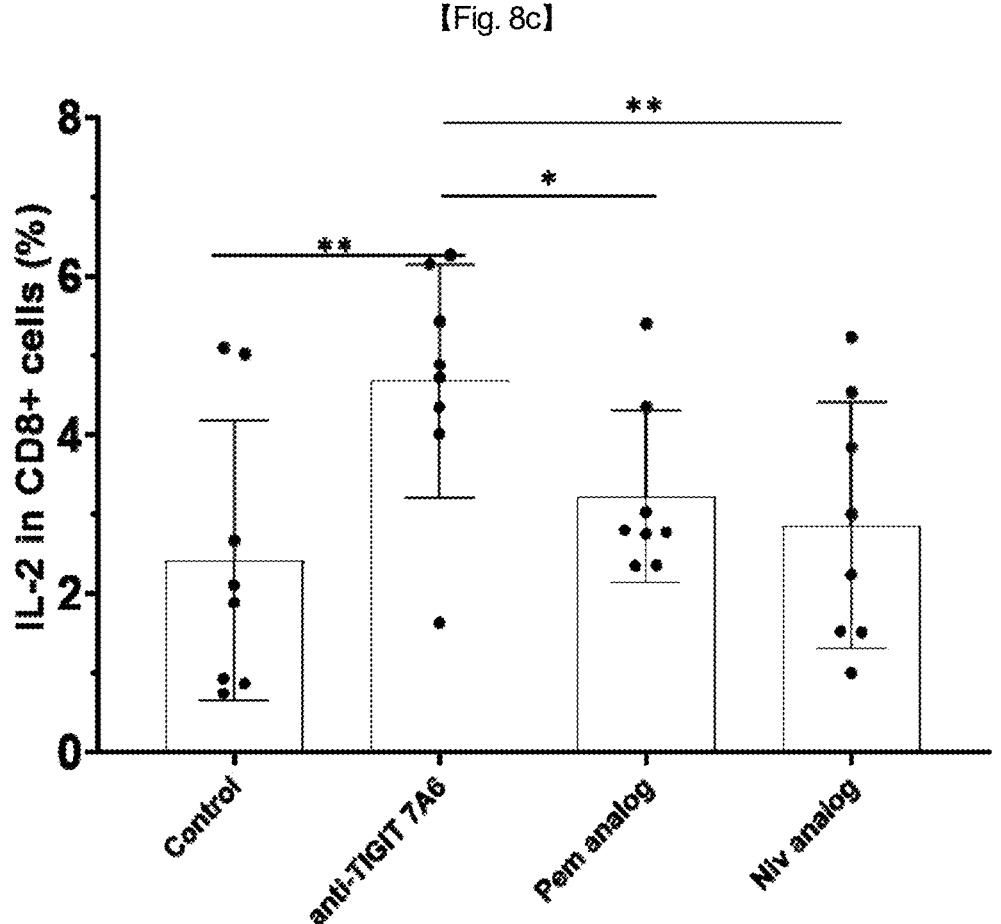

【Fig. 8d】
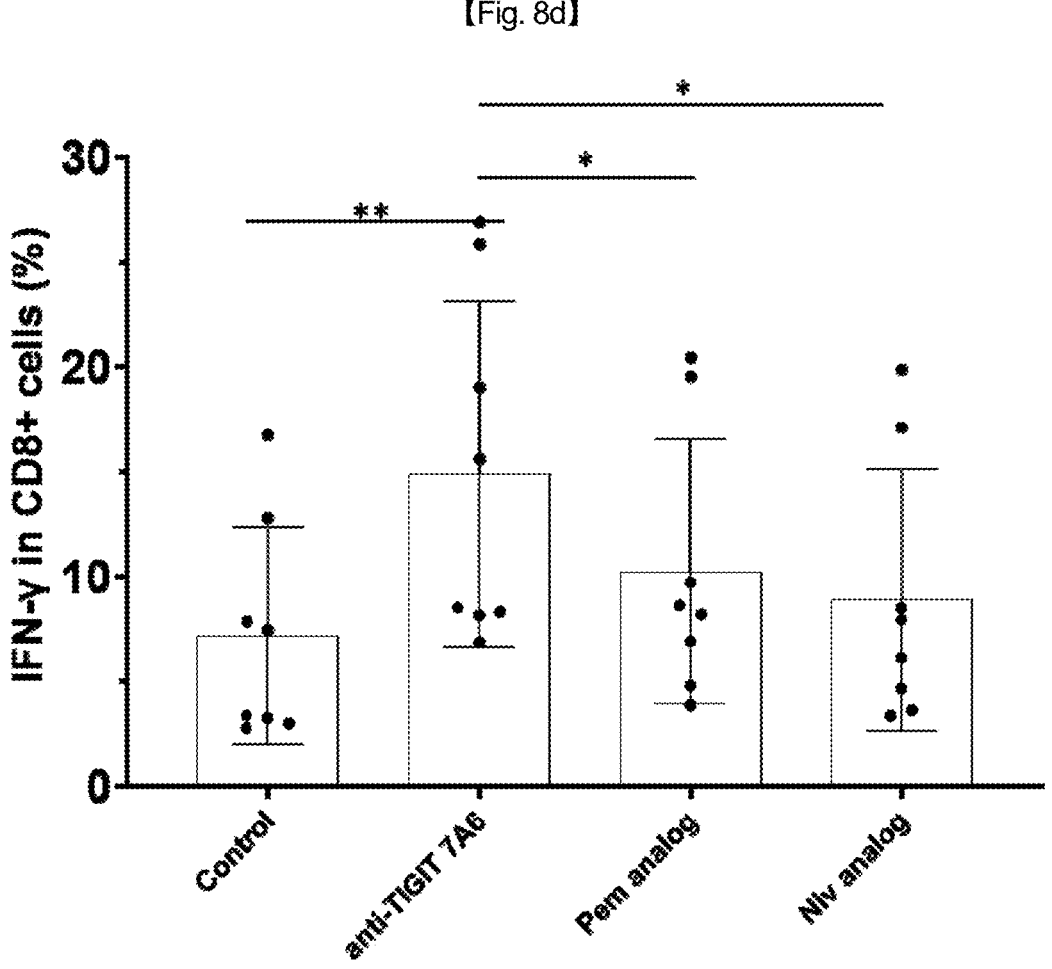

【Fig. 9a】
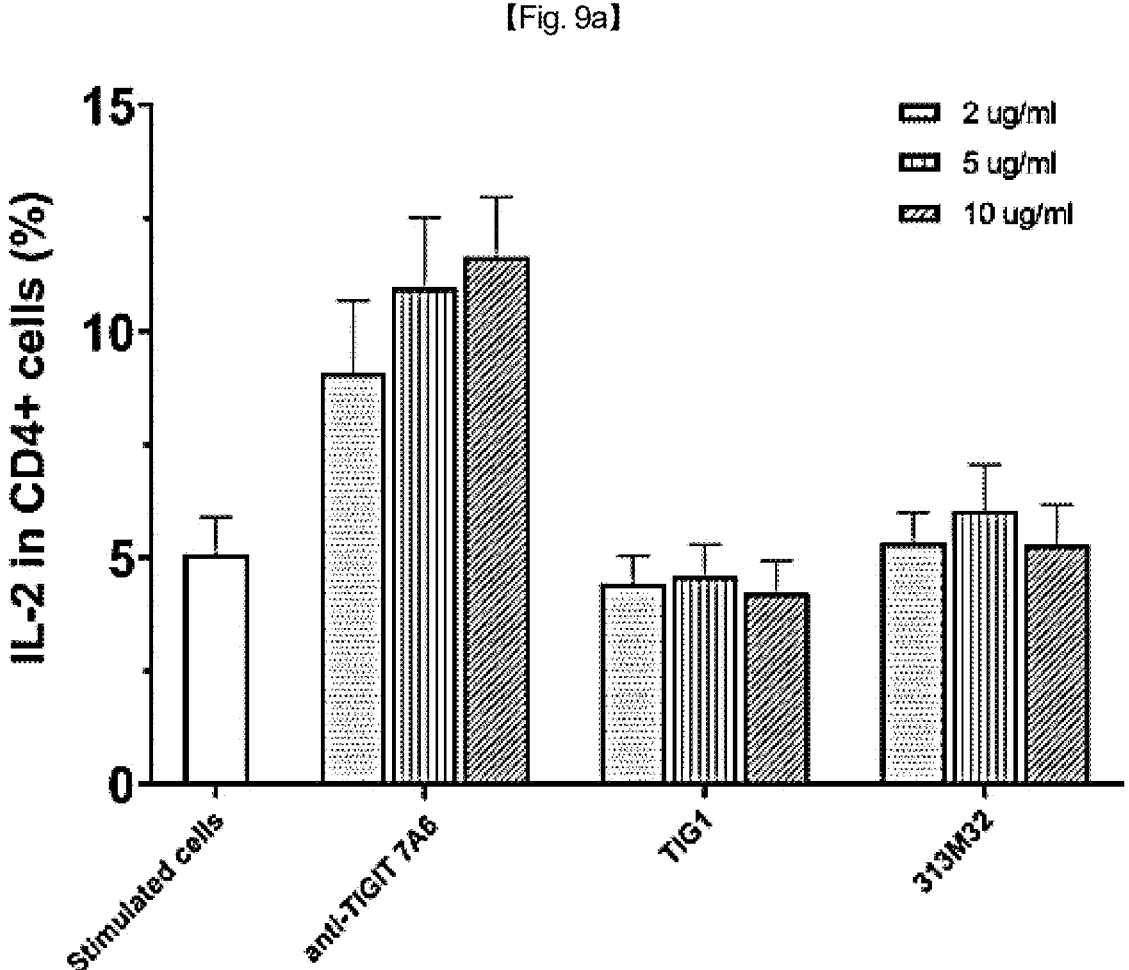

【Fig. 9b】
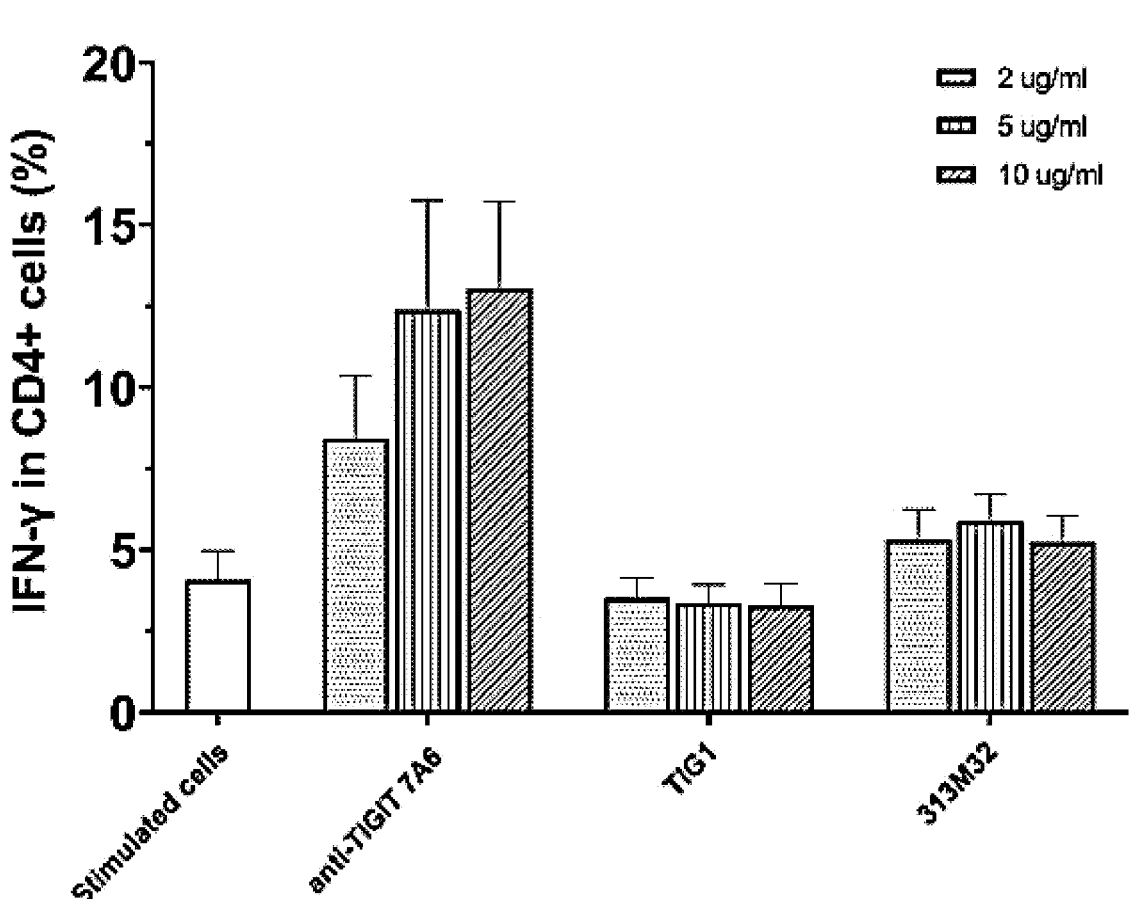

【Fig. 9c】
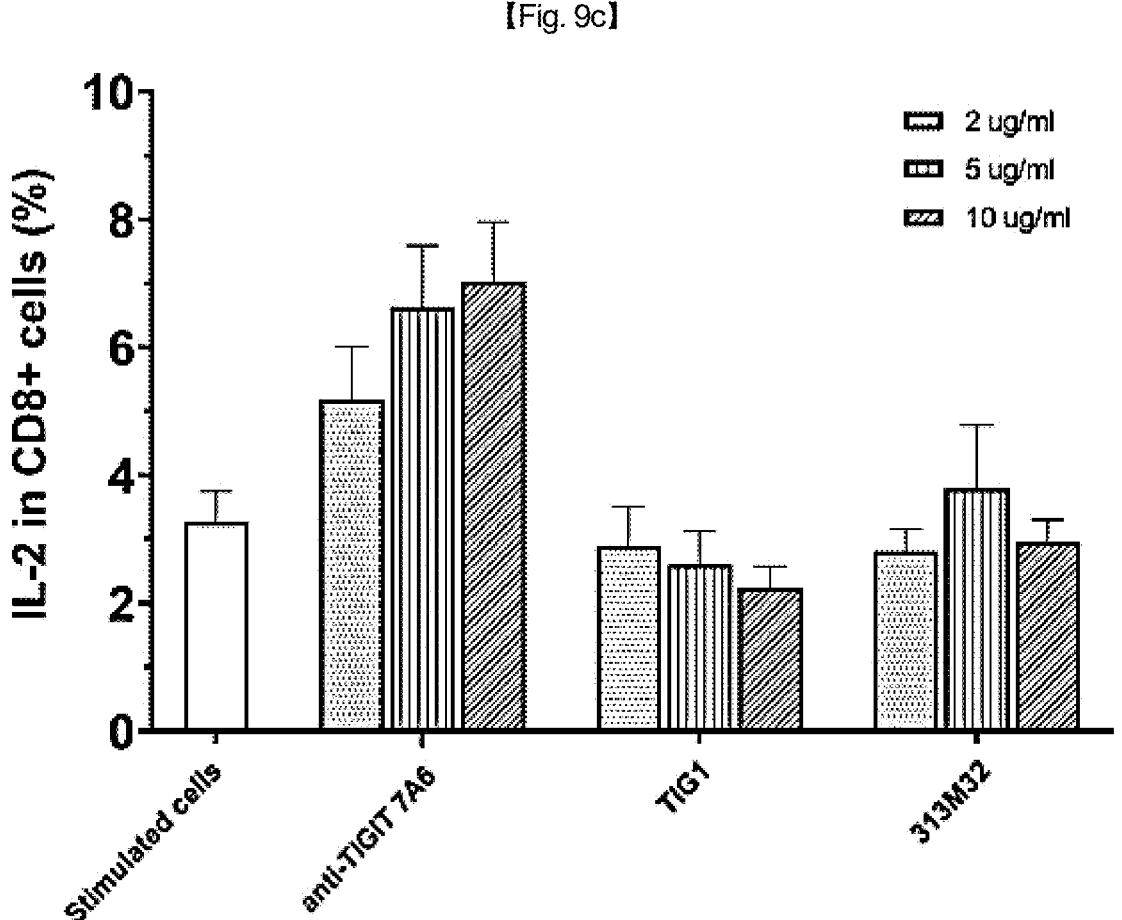

【Fig. 9d】
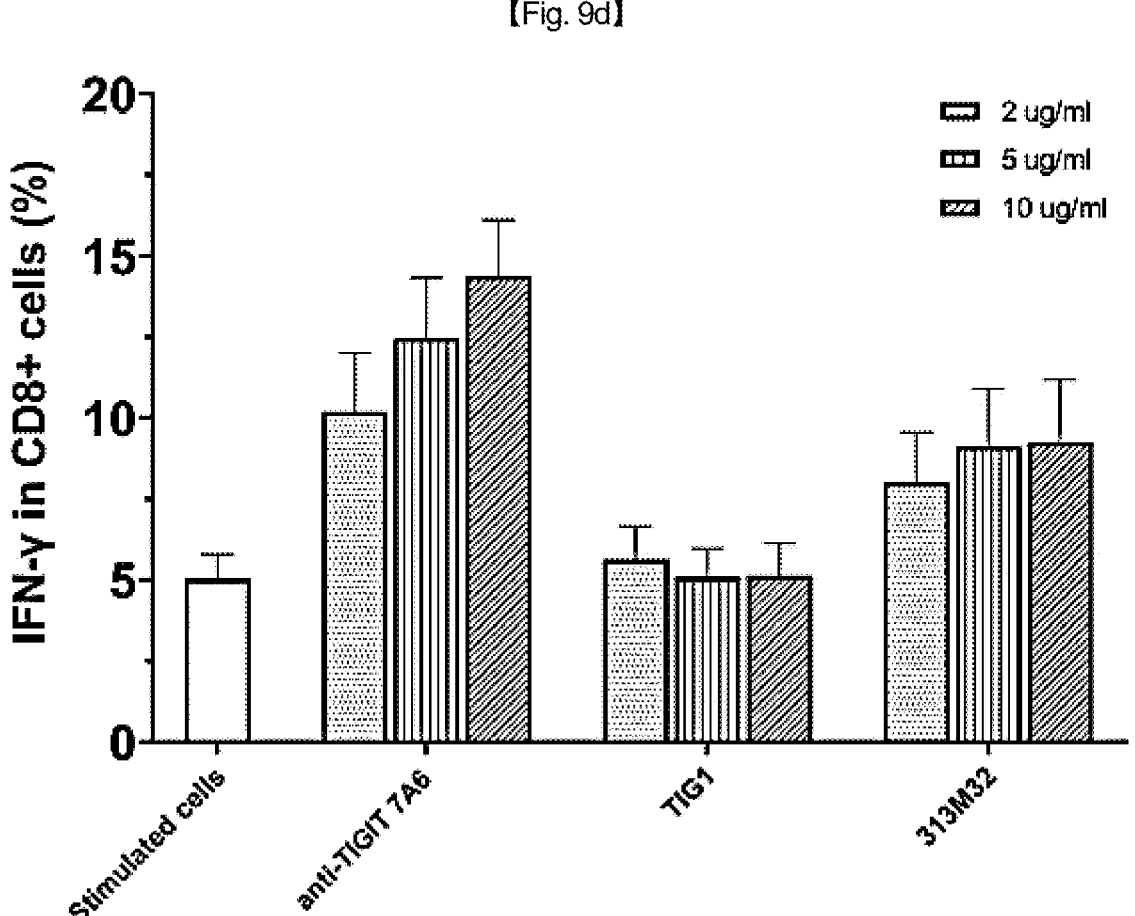

【Fig. 10a】
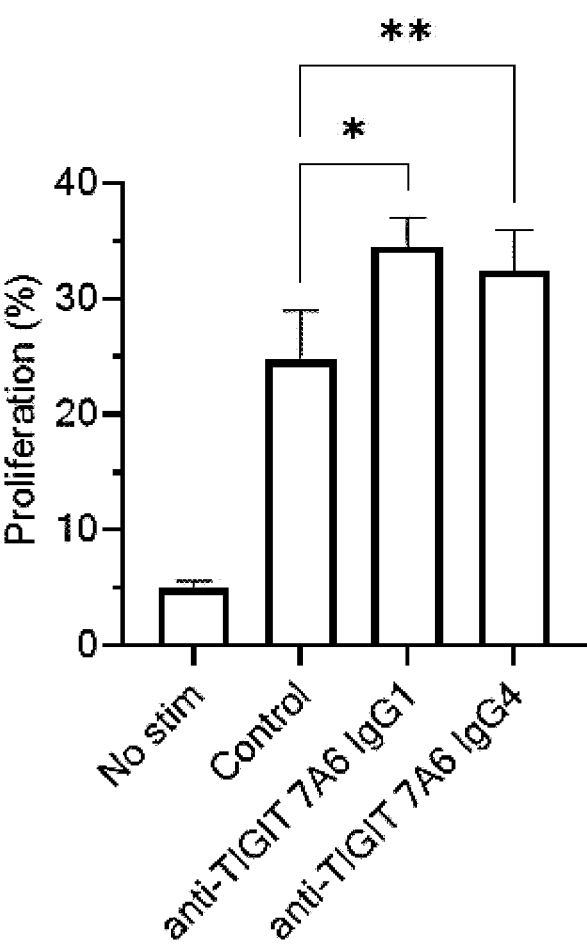

【Fig. 10b】
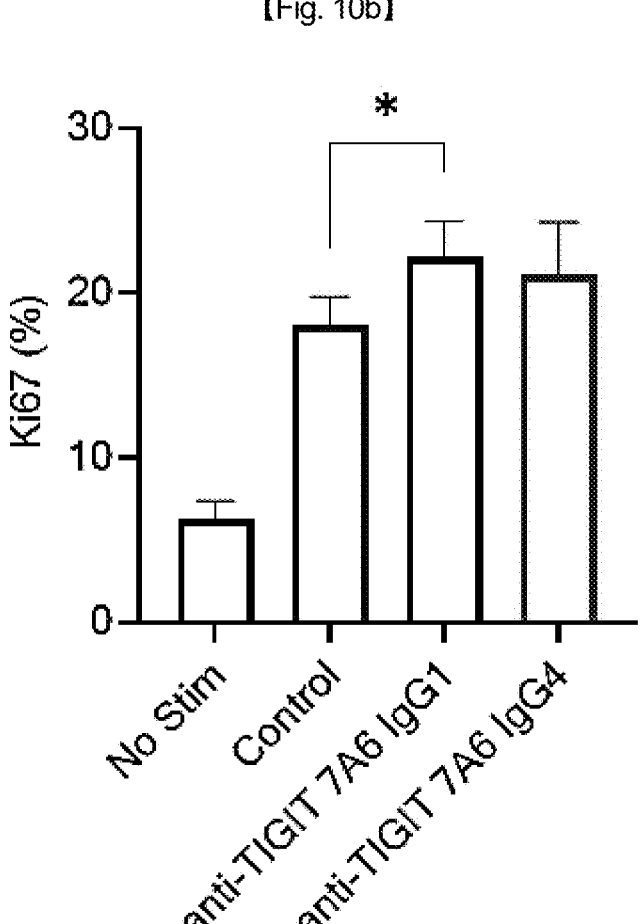

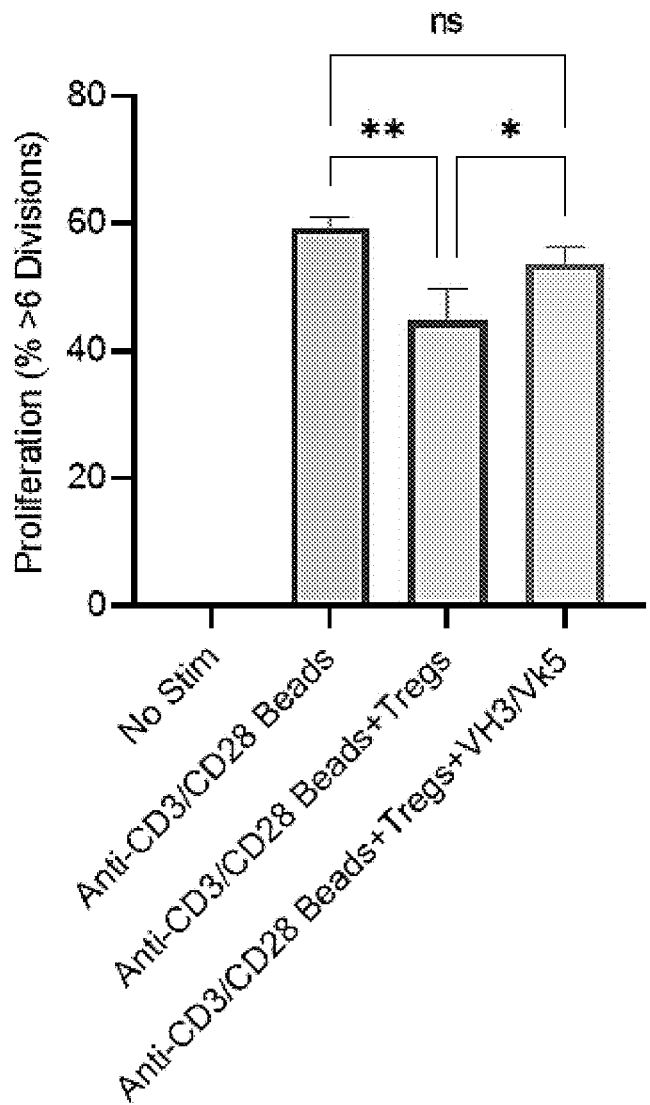
【Fig. 11】
CD8+ T cell proliferation in ± T$_{reg}$ cells ± 7A6 VH3/Vk5

【Fig. 12】
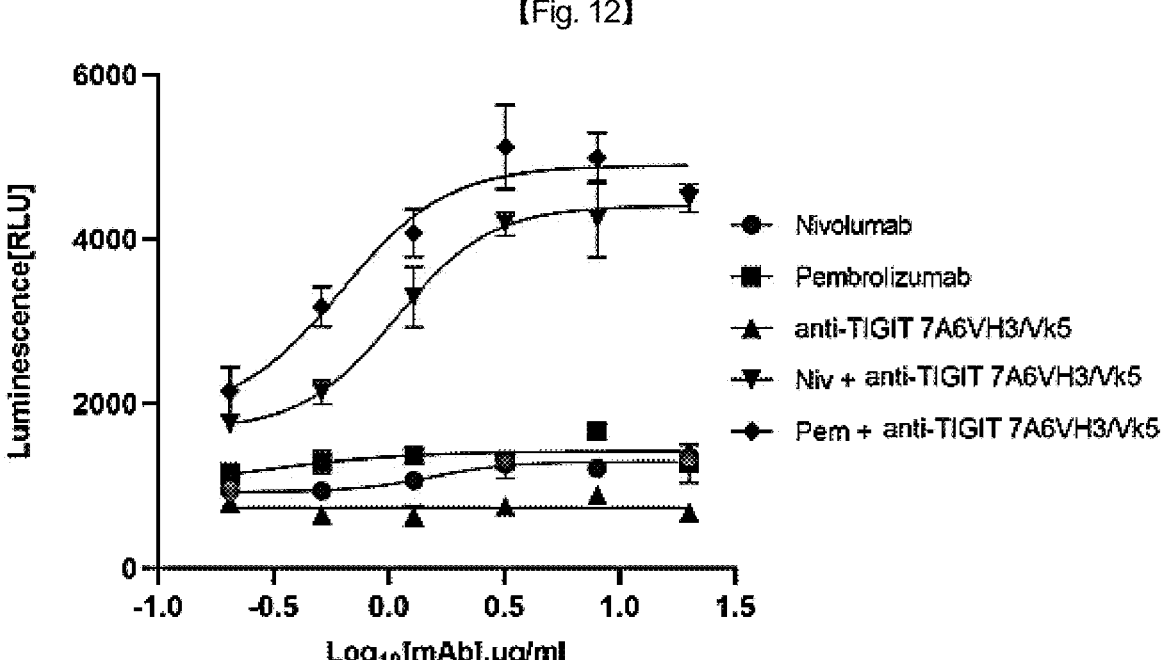
| ID | EC50 |
|---|---|
| Nivolumab | - |
| Pembrolizumab | - |
| anti-TIGIT 7A6 | - |
| Niv+anti-TIGIT 7A6 | 0.5944 |
| Pem+anti-TIGIT 7A6 | 0.38 |

【Fig. 13a】
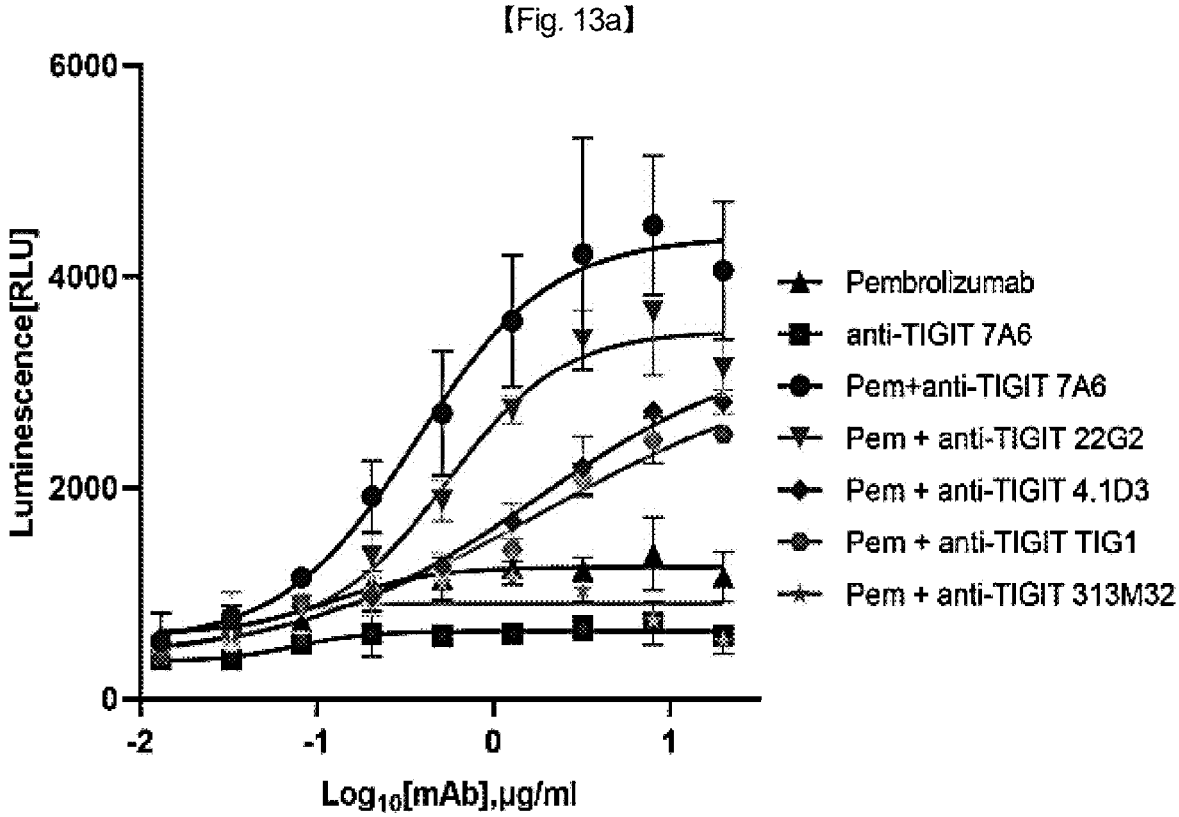
| ID | EC50 |
|---|---|
| Pembrolizumab | - |
| anti-TIGIT 7A6 VH3/Vk5 | - |
| Pem + 7A6 VH3/Vk5 | 0.3986 |
| Pem + 22G2 | 0.4906 |
| Pem + 4.1D3 | 0.8271 |
| Pem + TIG1 | 0.6114 |
| Pem + 313M32 | - |

【Fig. 13b】
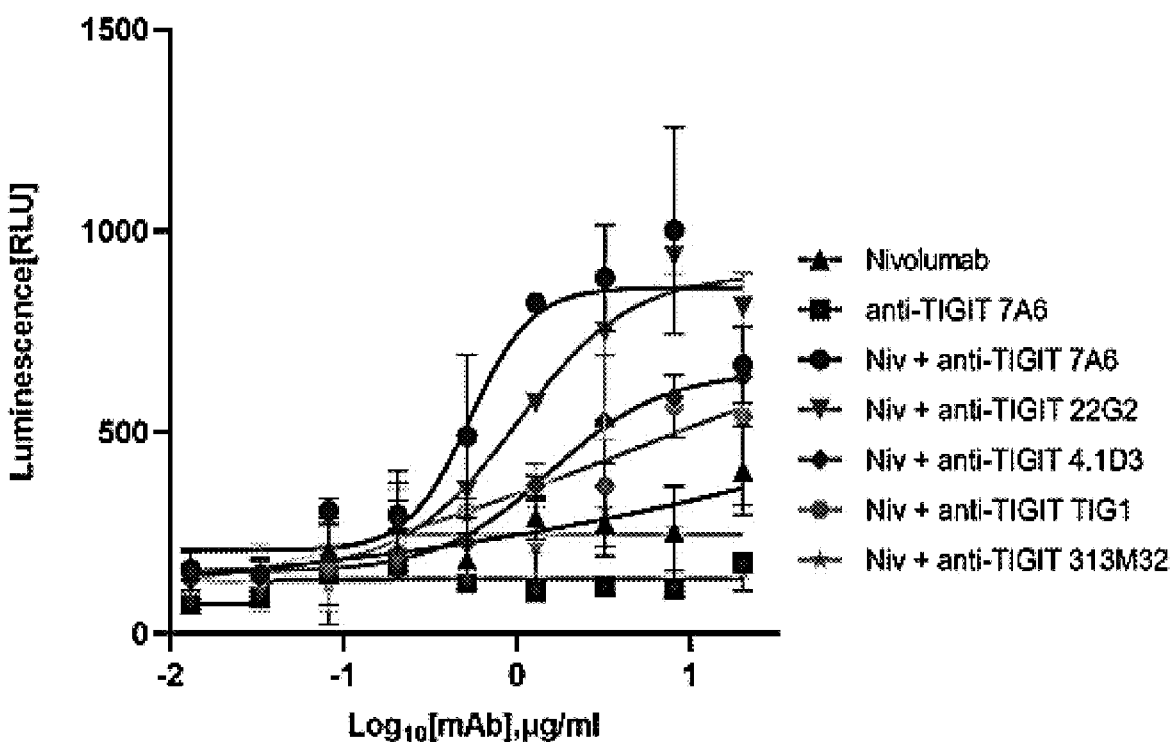
| ID | EC50 |
|---|---|
| Nivolumab | - |
| anti-TIGIT 7A6 VH3/Vk5 | - |
| Niv + 7A6 VH3/Vk5 | 0.5814 |
| Niv + 22G2 | 0.9742 |
| Niv + 4.1D3 | 1.258 |
| Niv + TIG1 | 0.9229 |
| Niv + 313M32 | - |

【Fig. 14a】
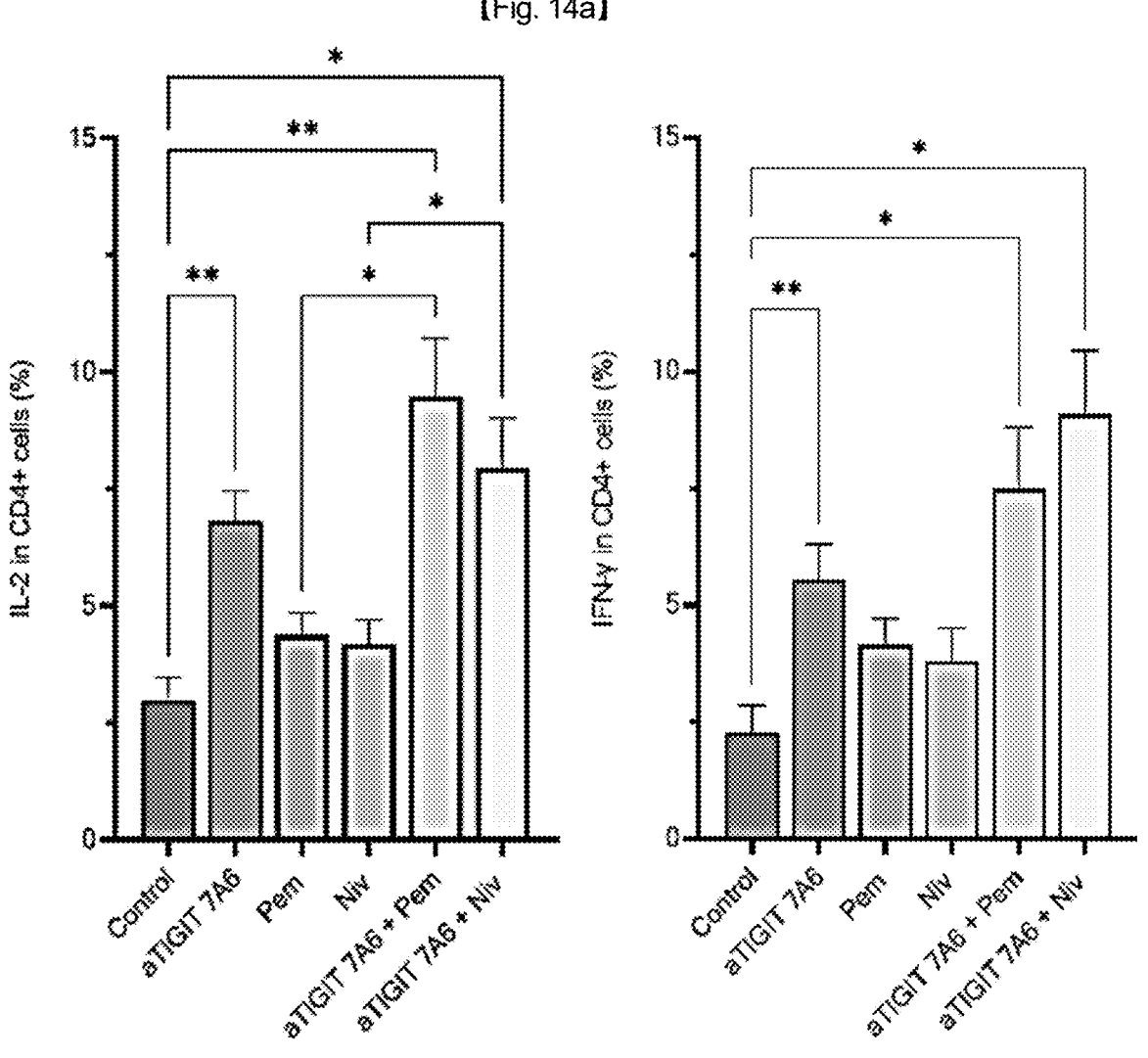

【Fig. 14b】
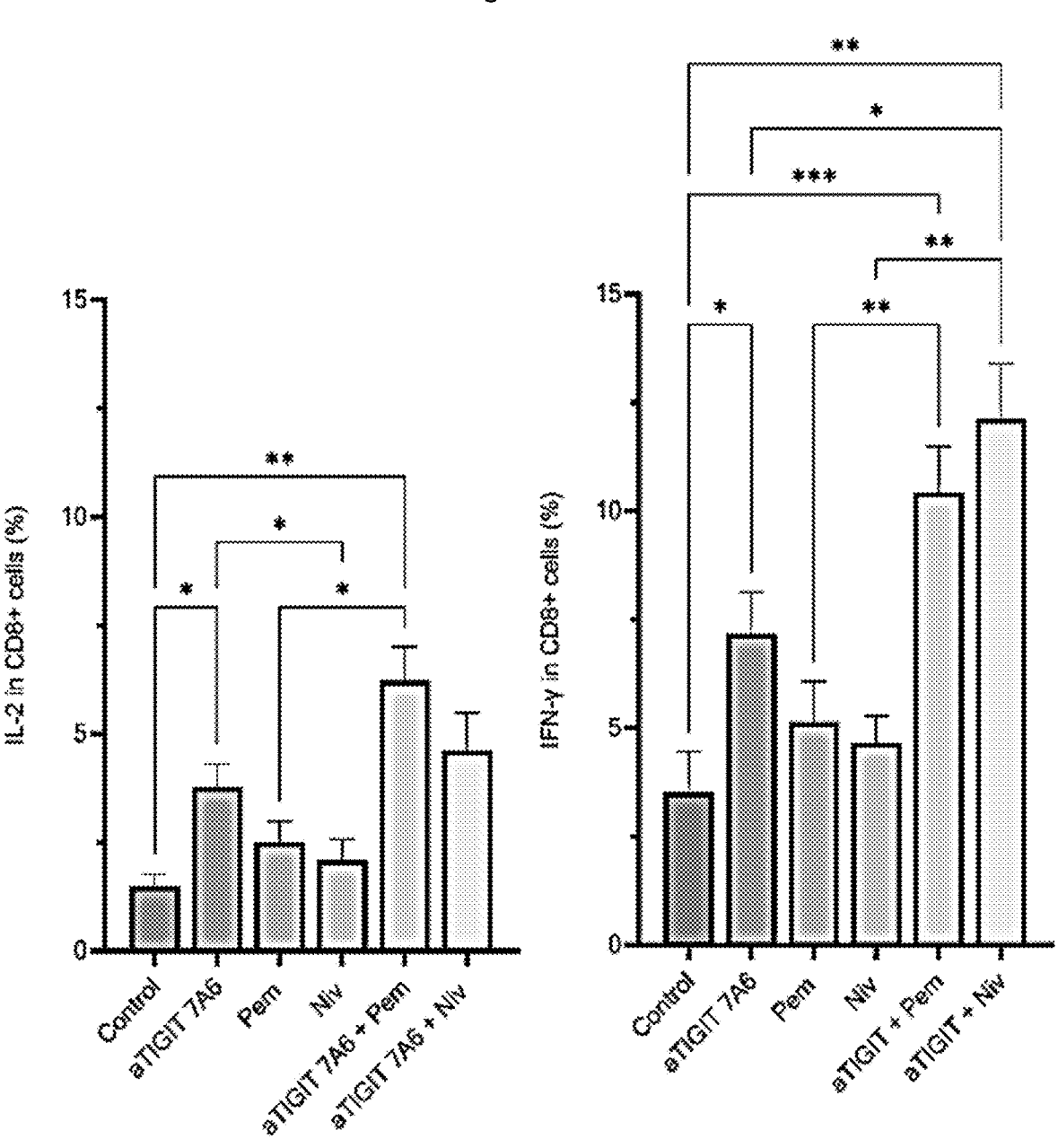

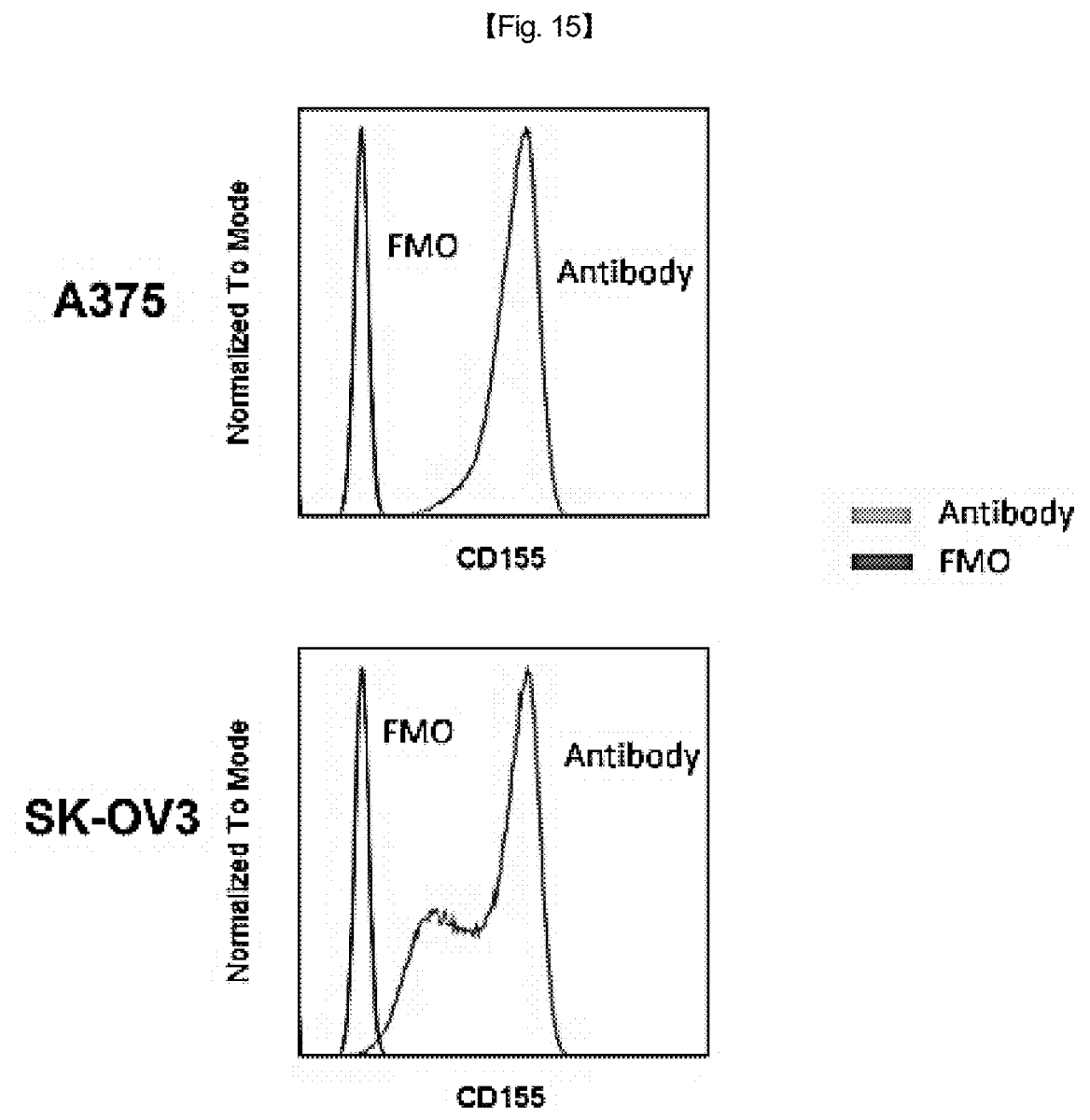

【Fig. 15】

[Fig. 16]
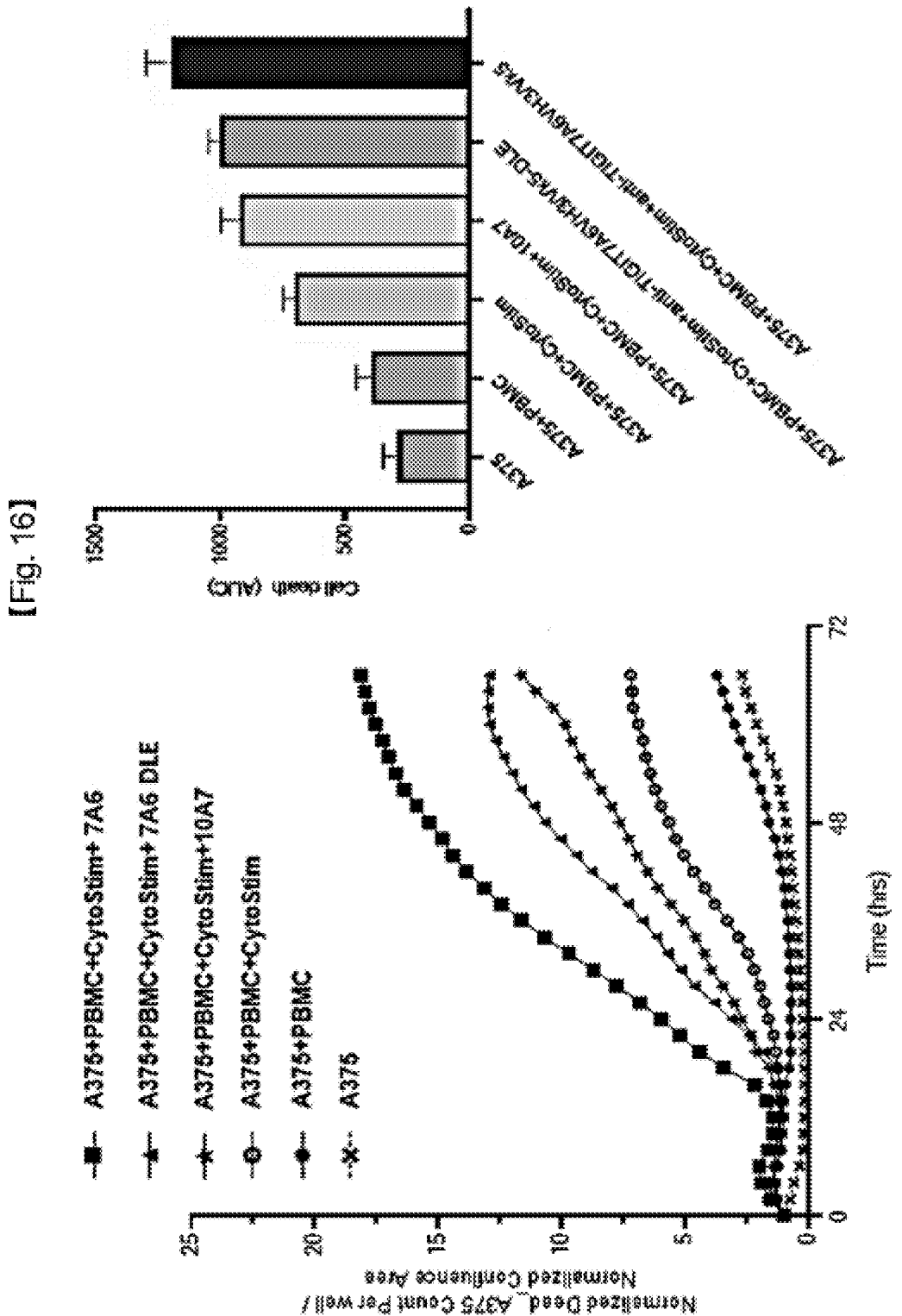

【Fig. 17a】
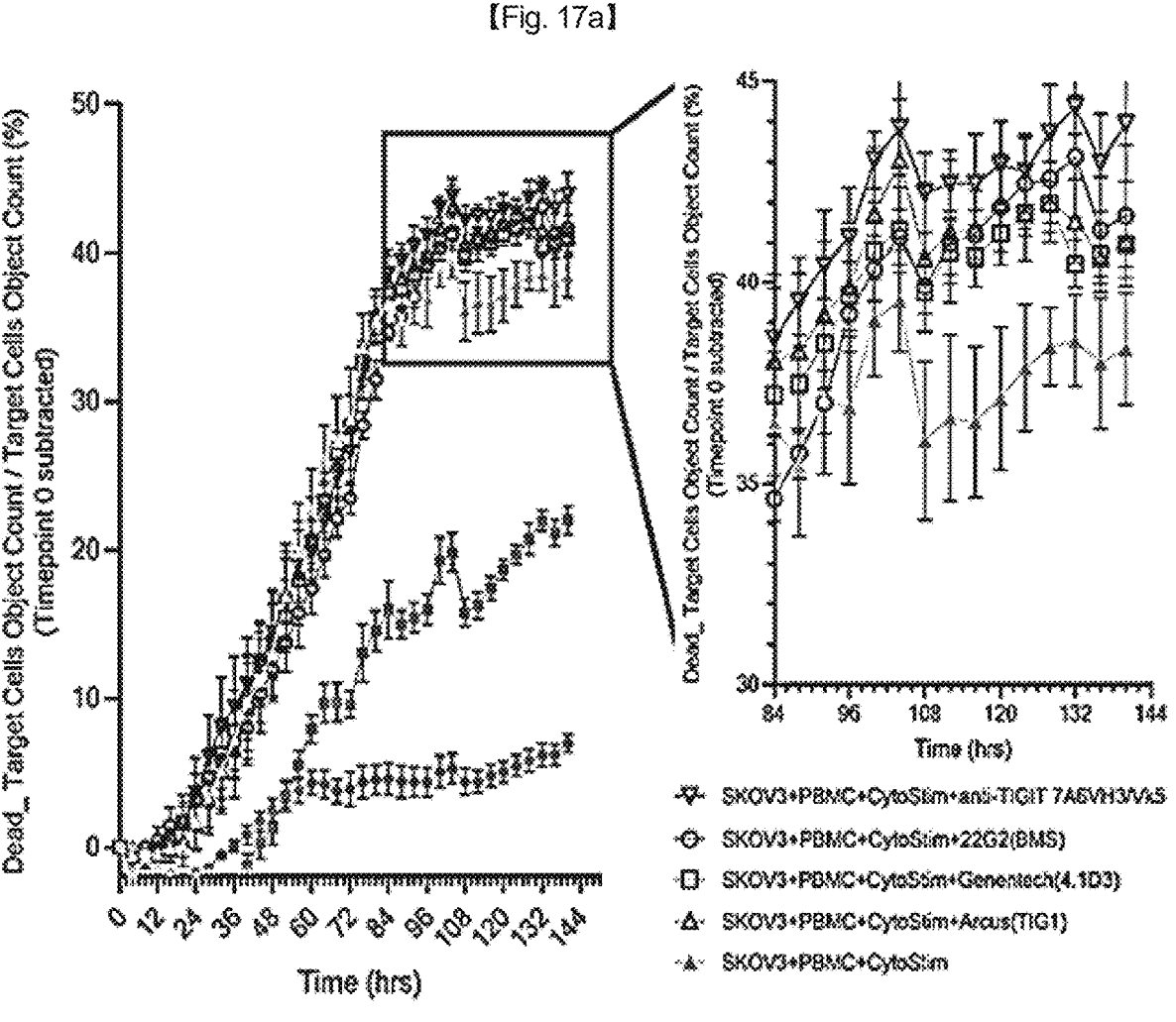
- ─◆─ SKOV3 only
- ─■─ SKOV3+PBMC
- ─▲─ SKOV3+PBMC+CytoStim
- ─○─ SKOV3+PBMC+CytoStim+22G2(BMS)
- ─□─ SKOV3+PBMC+CytoStim+Genentech(4.1D3)
- ─△─ SKOV3+PBMC+CytoStim+Arcus(TIG1)
- ─▽─ SKOV3+PBMC+CytoStim+anti-TIGIT 7A6VH3/Vk5

【Fig. 17b】
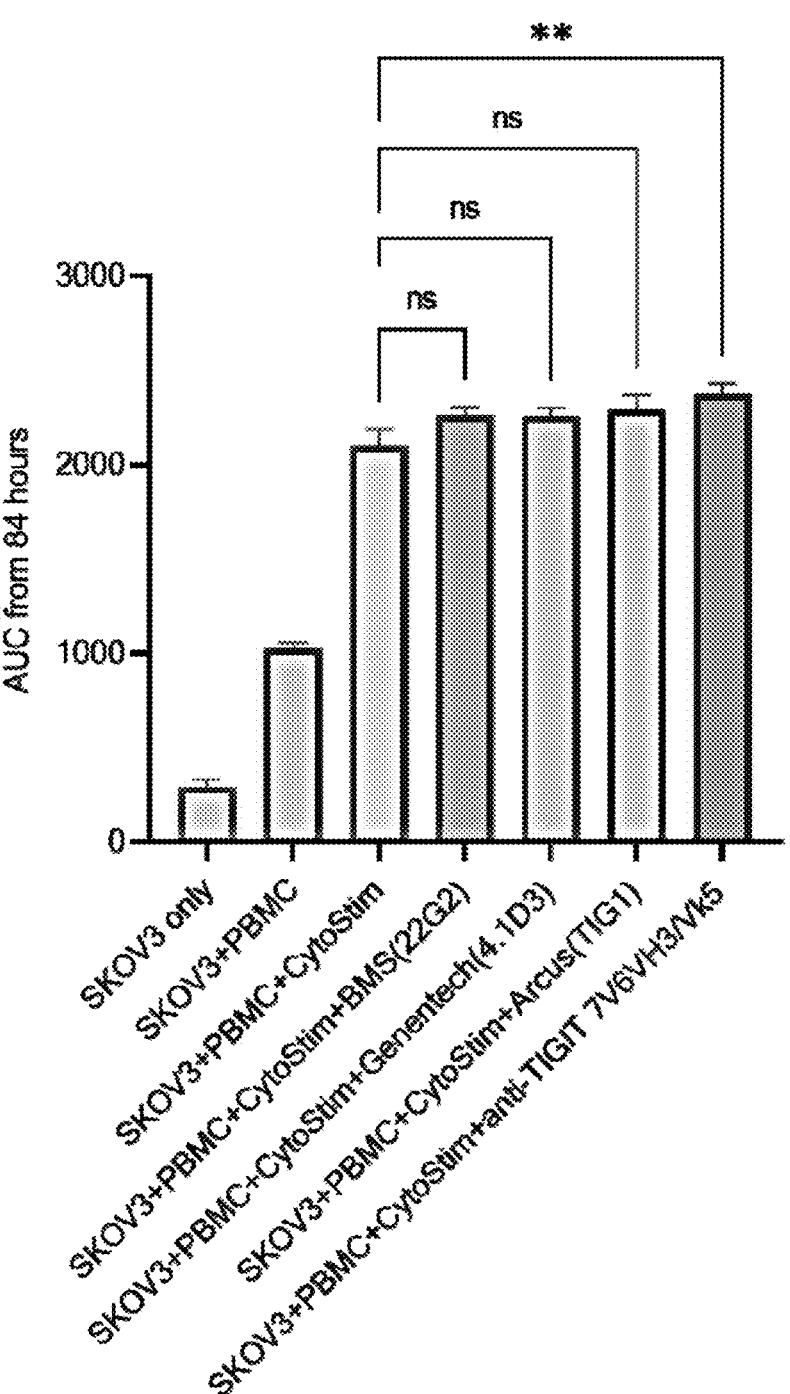

[Fig. 18]
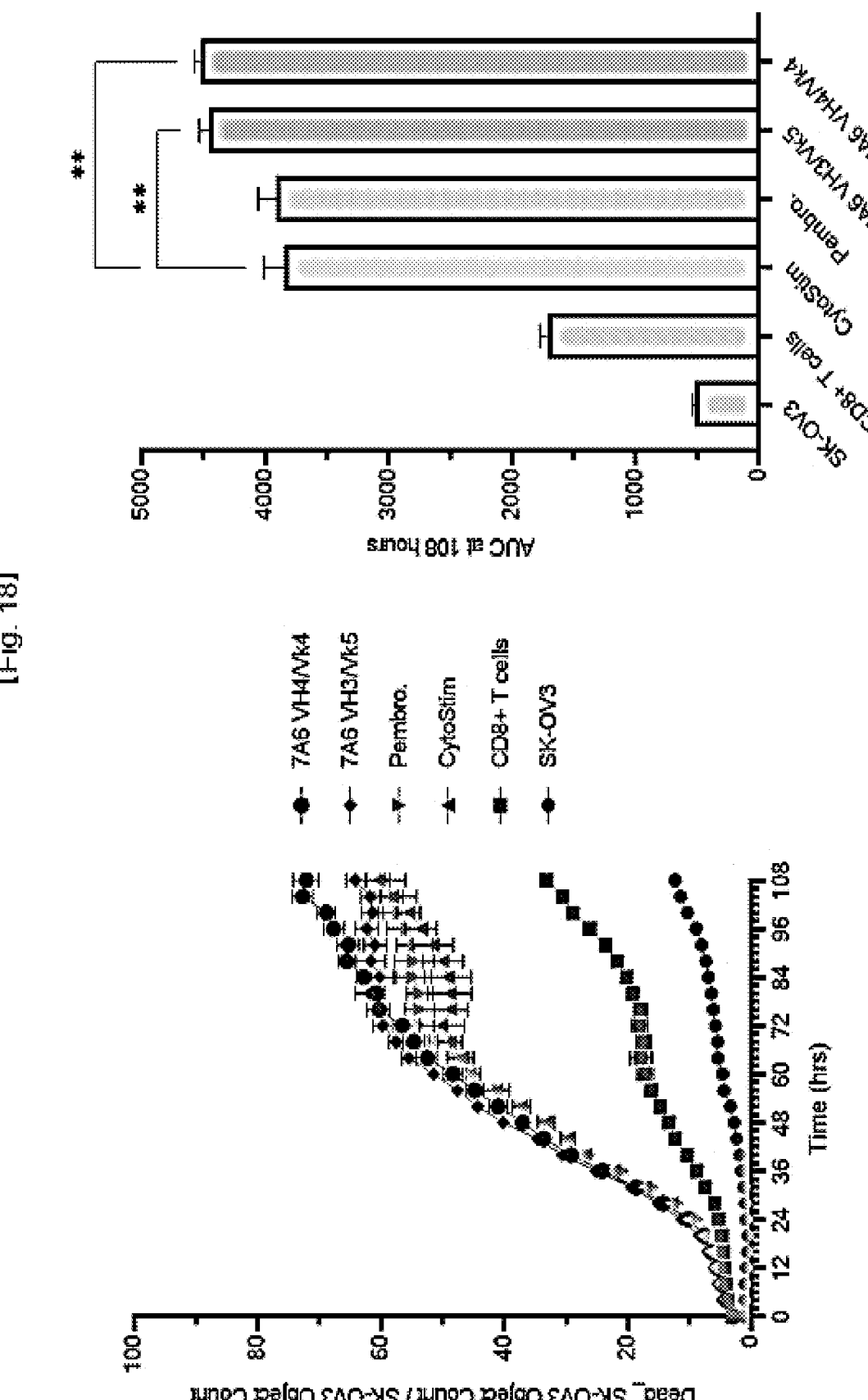

[Fig. 19]
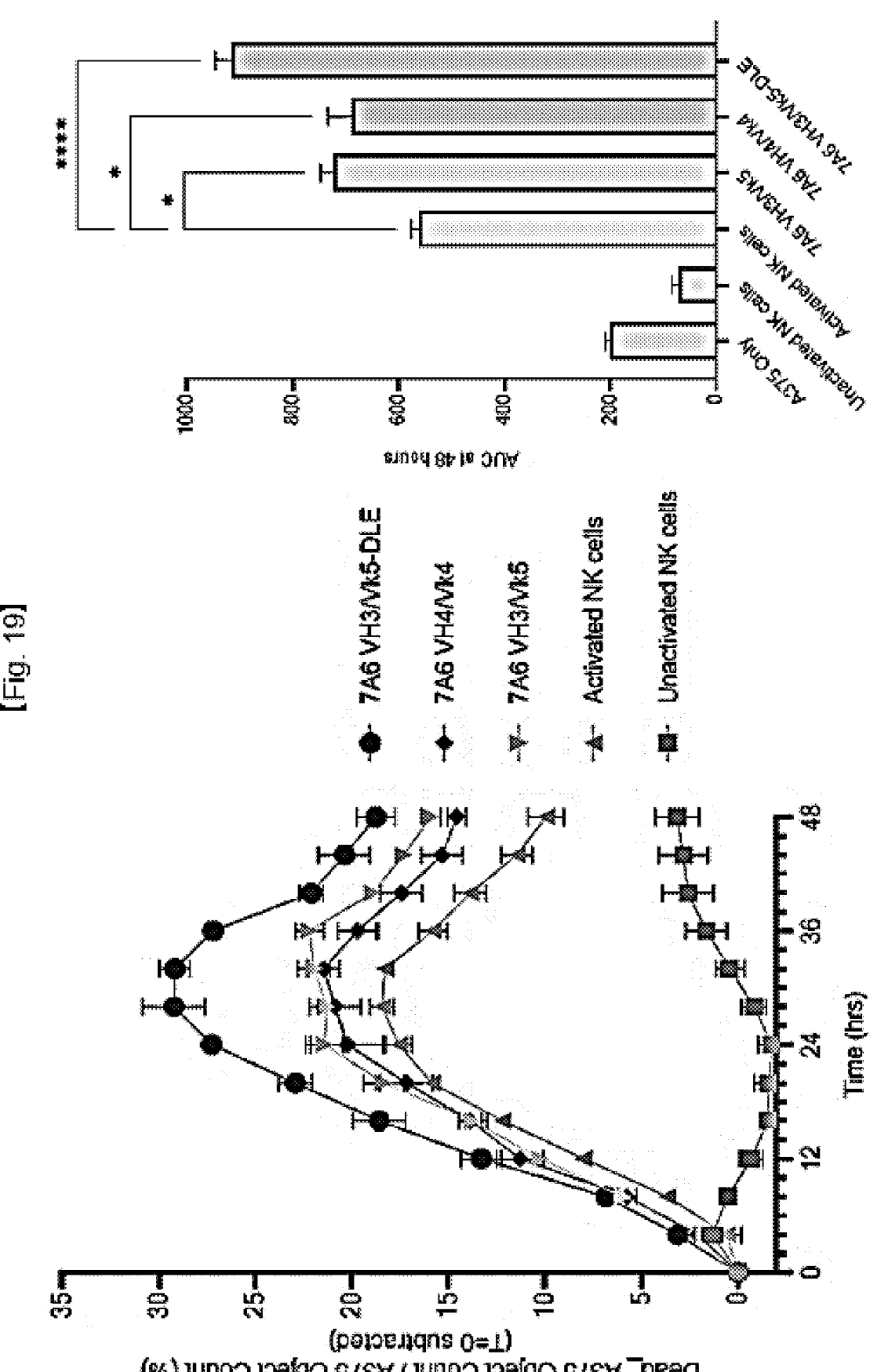

【Fig. 20】
Mean Tumor Volume ± SEM
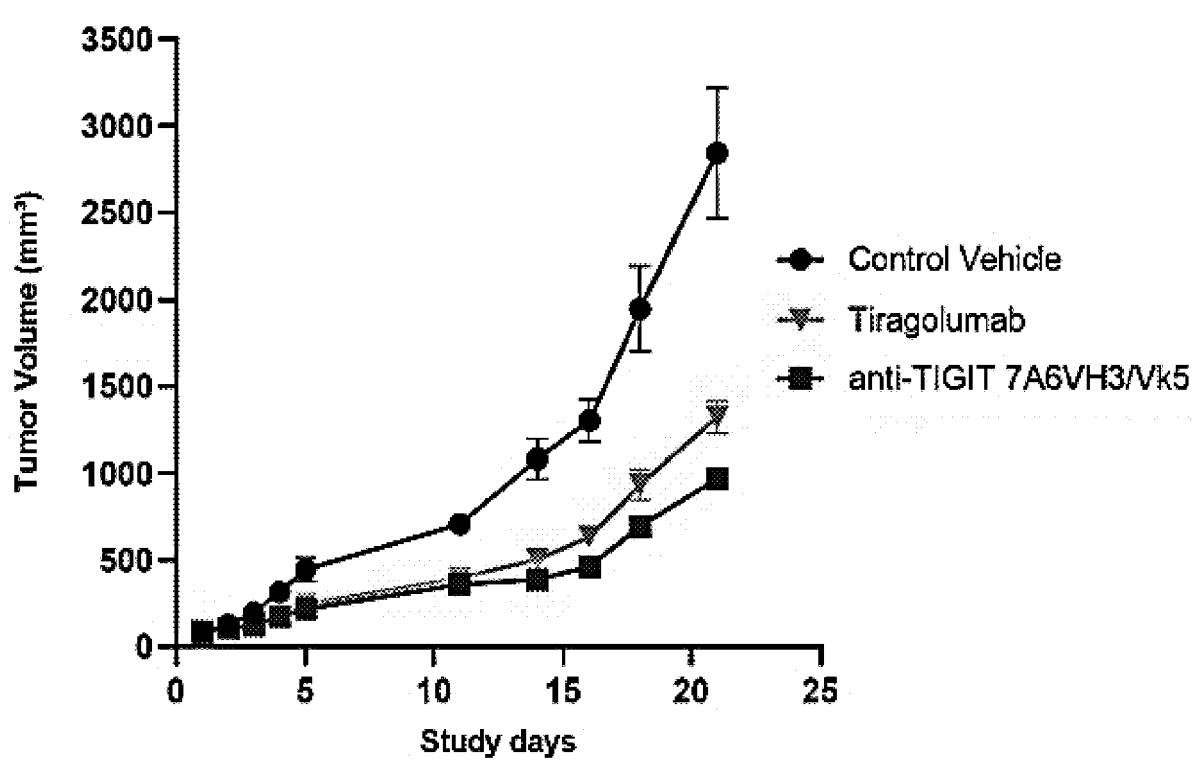

【Fig. 21】
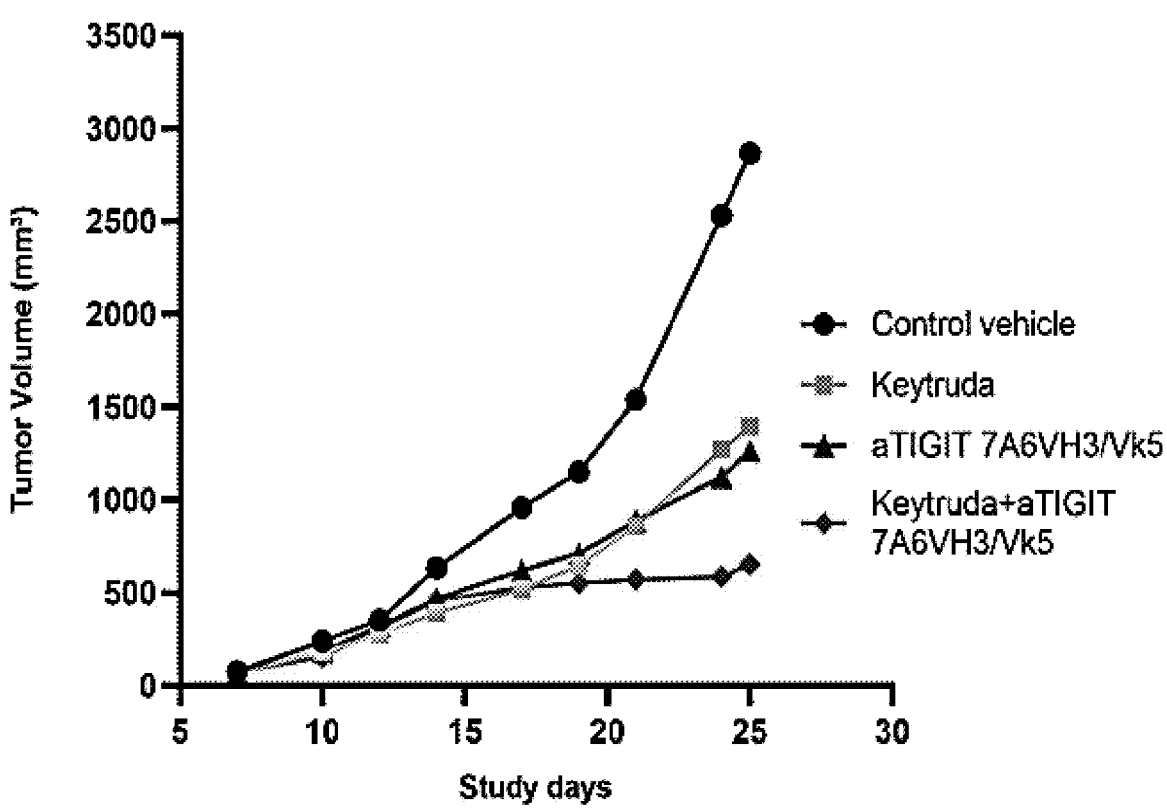
Mean Tumor Volume ± SEM

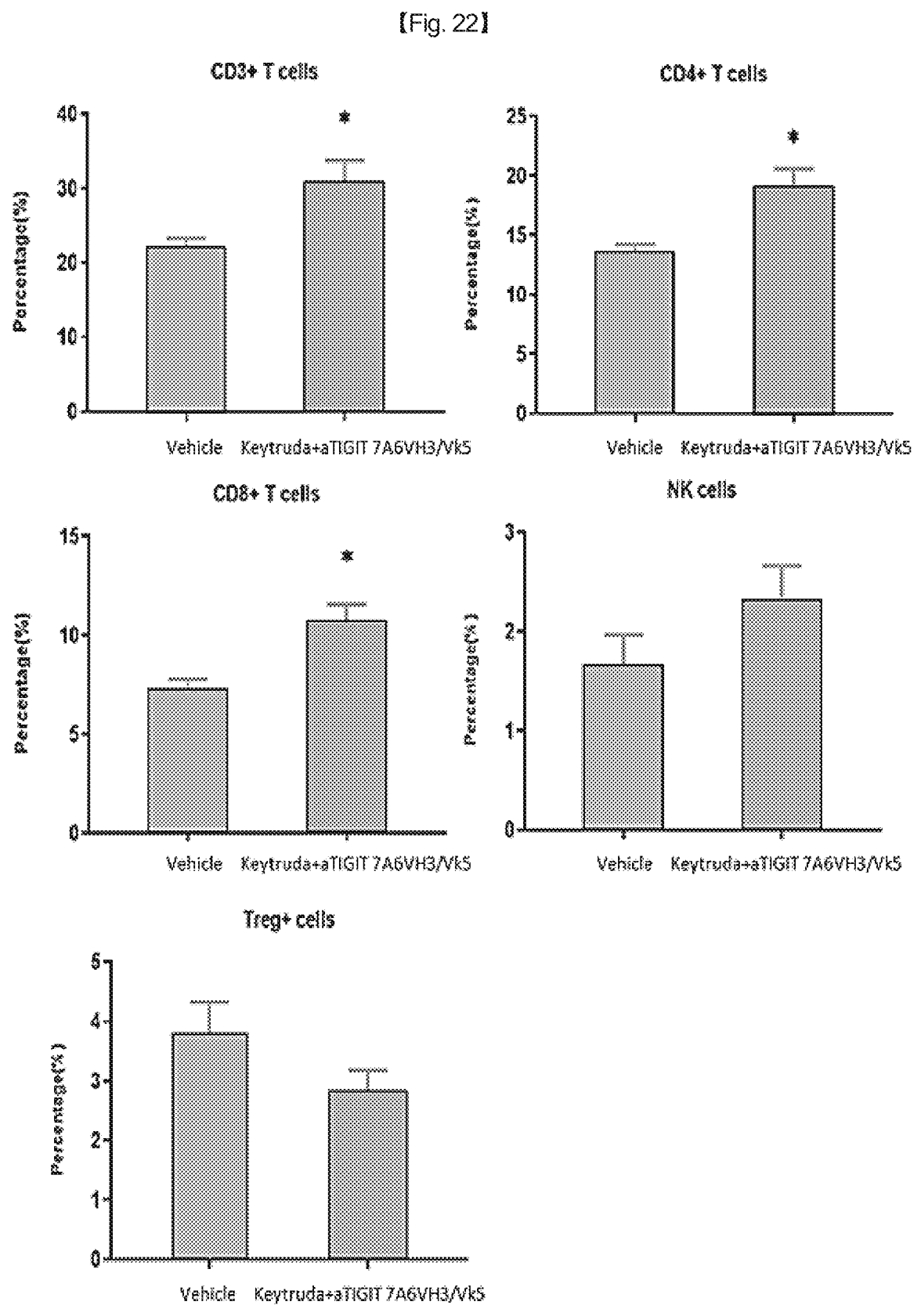

【Fig. 22】

CD3+ T cells

CD4+ T cells

CD8+ T cells

NK cells

Treg+ cells

【Fig. 23】
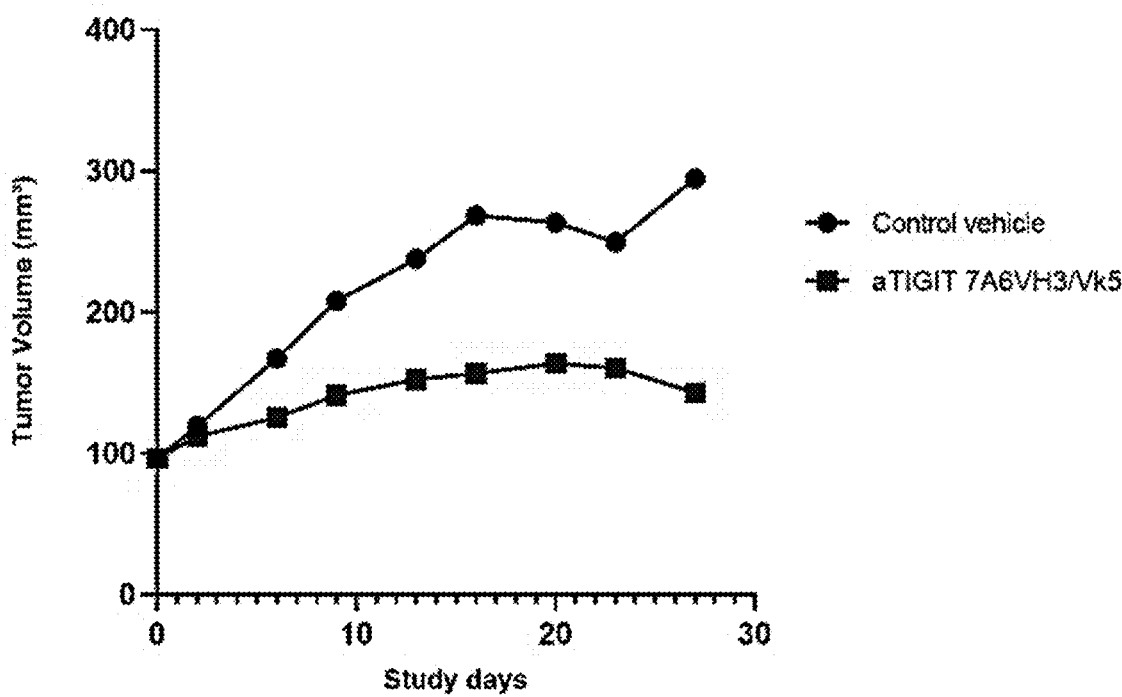
【Fig. 24】
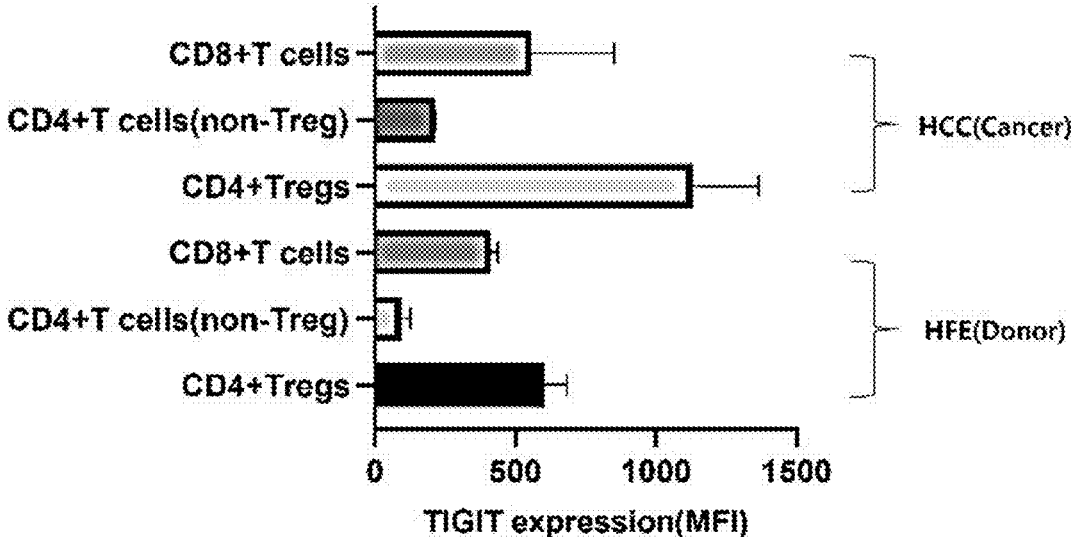

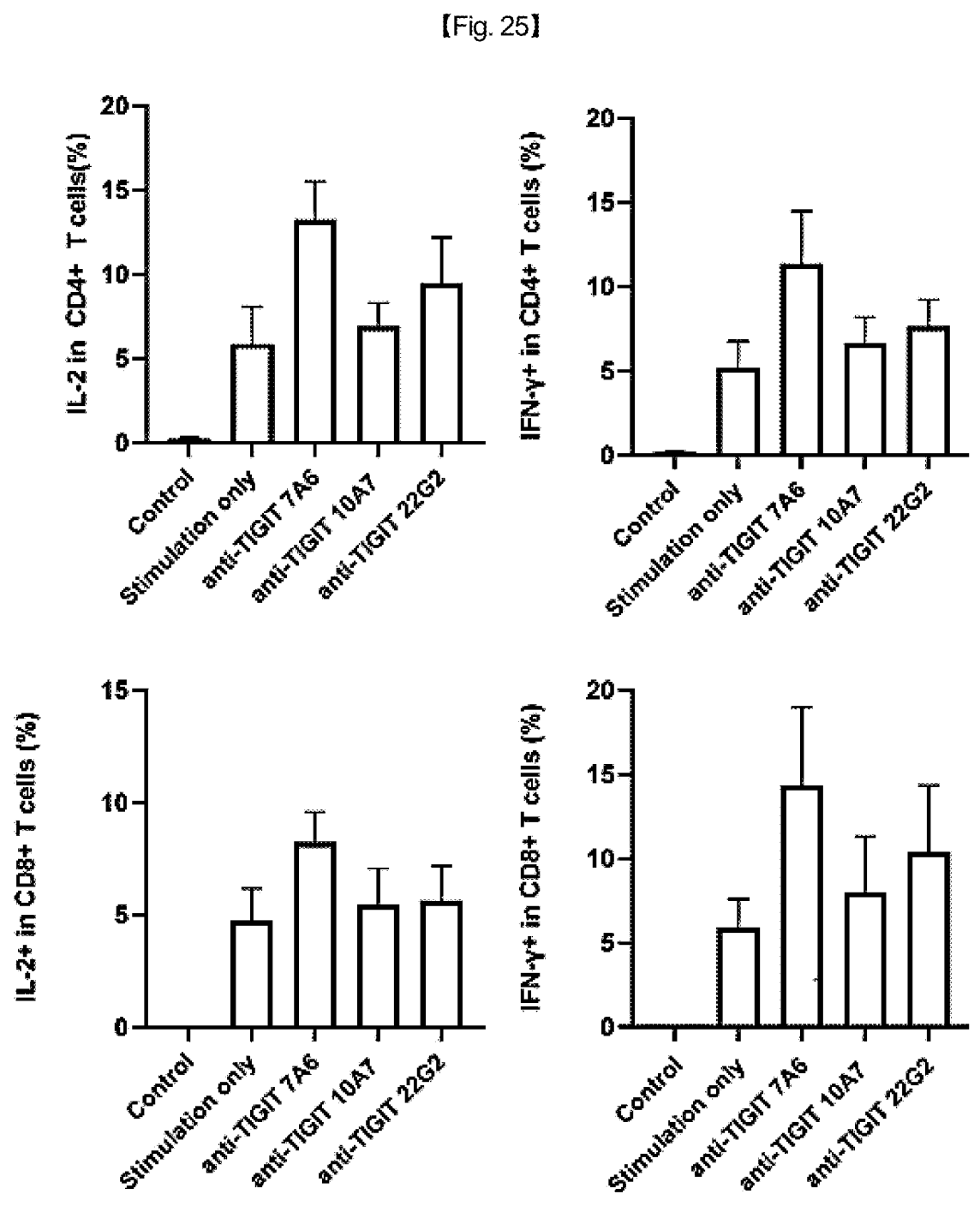

【Fig. 25】

【Fig. 26】
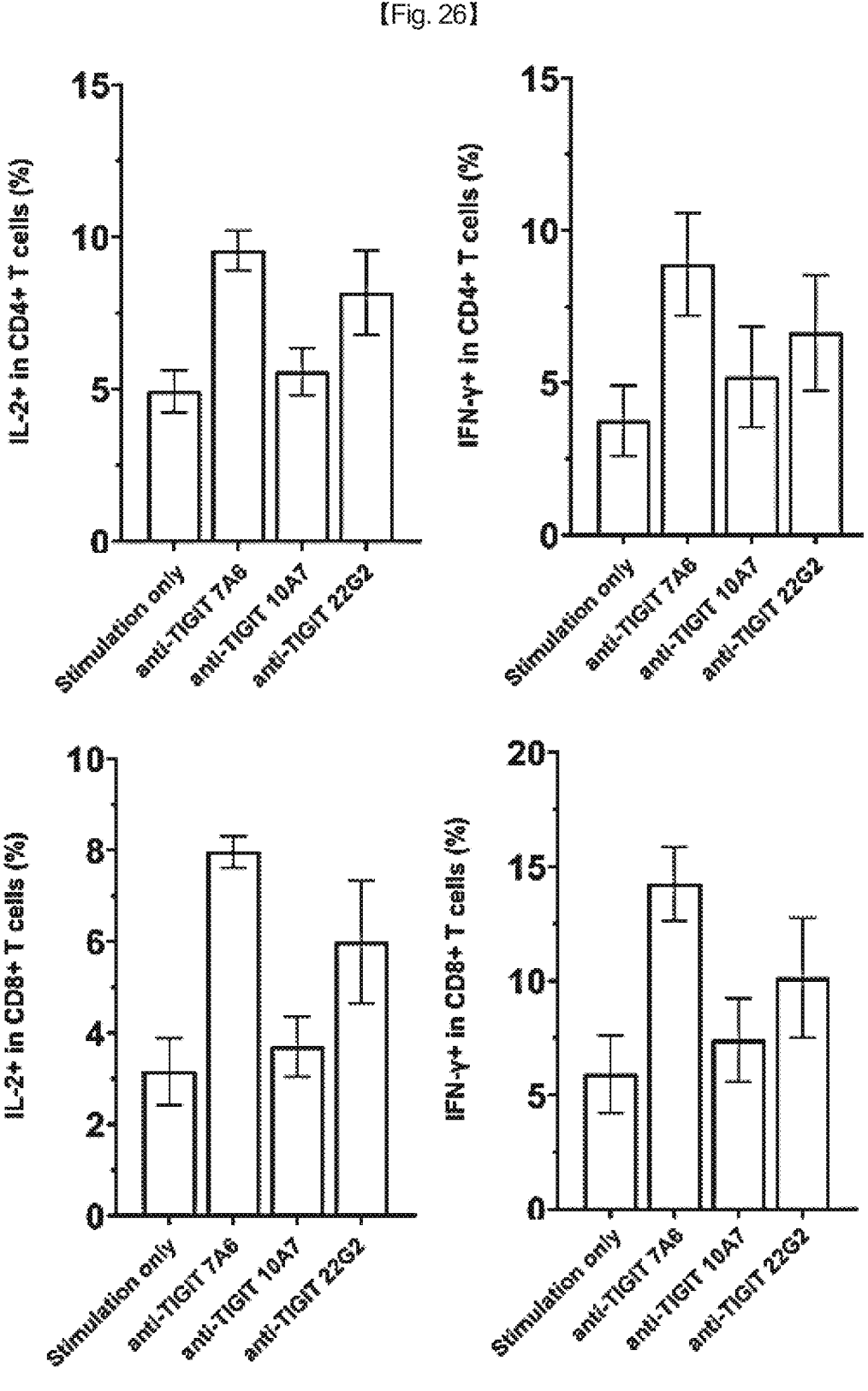

【Fig. 27】
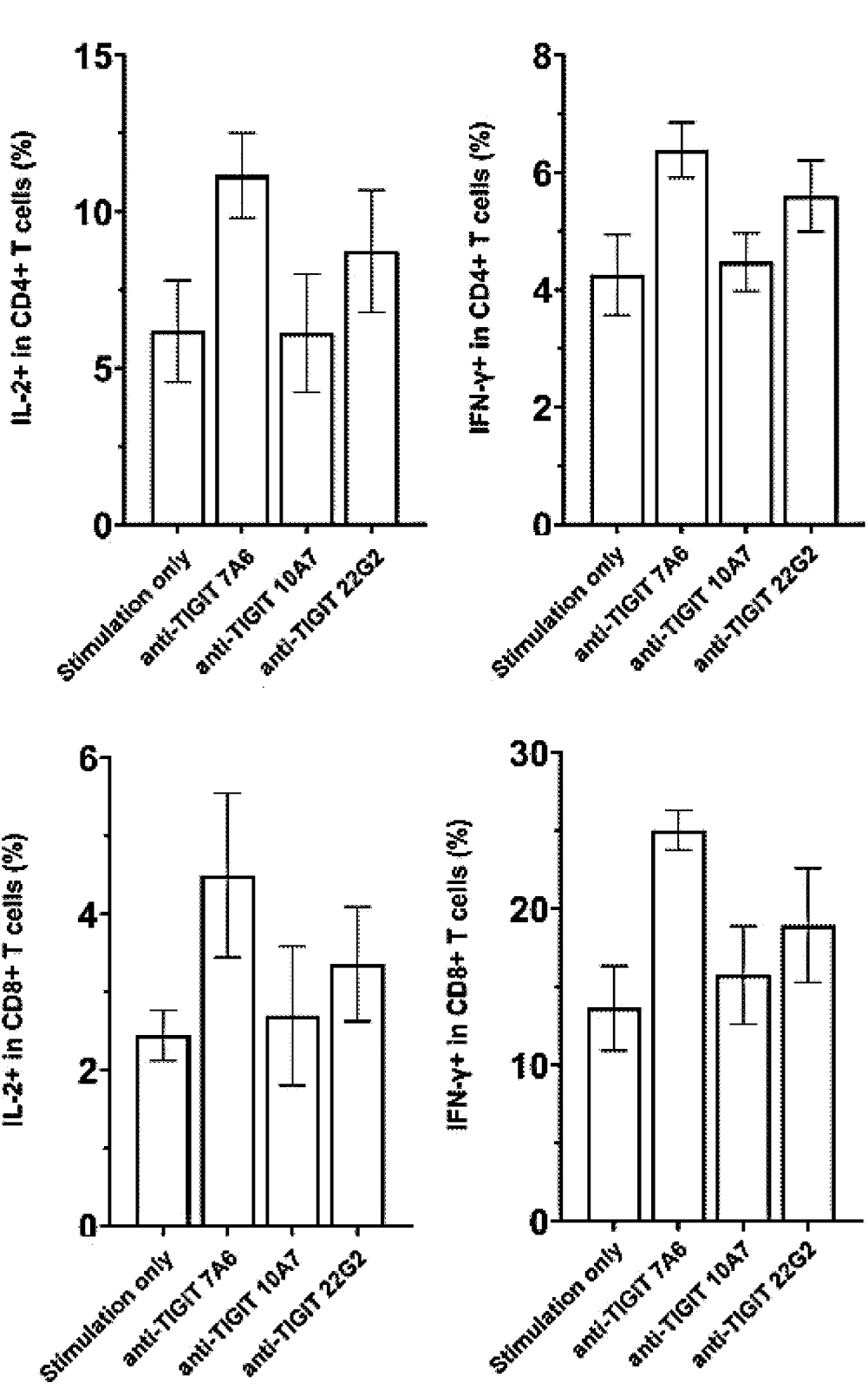

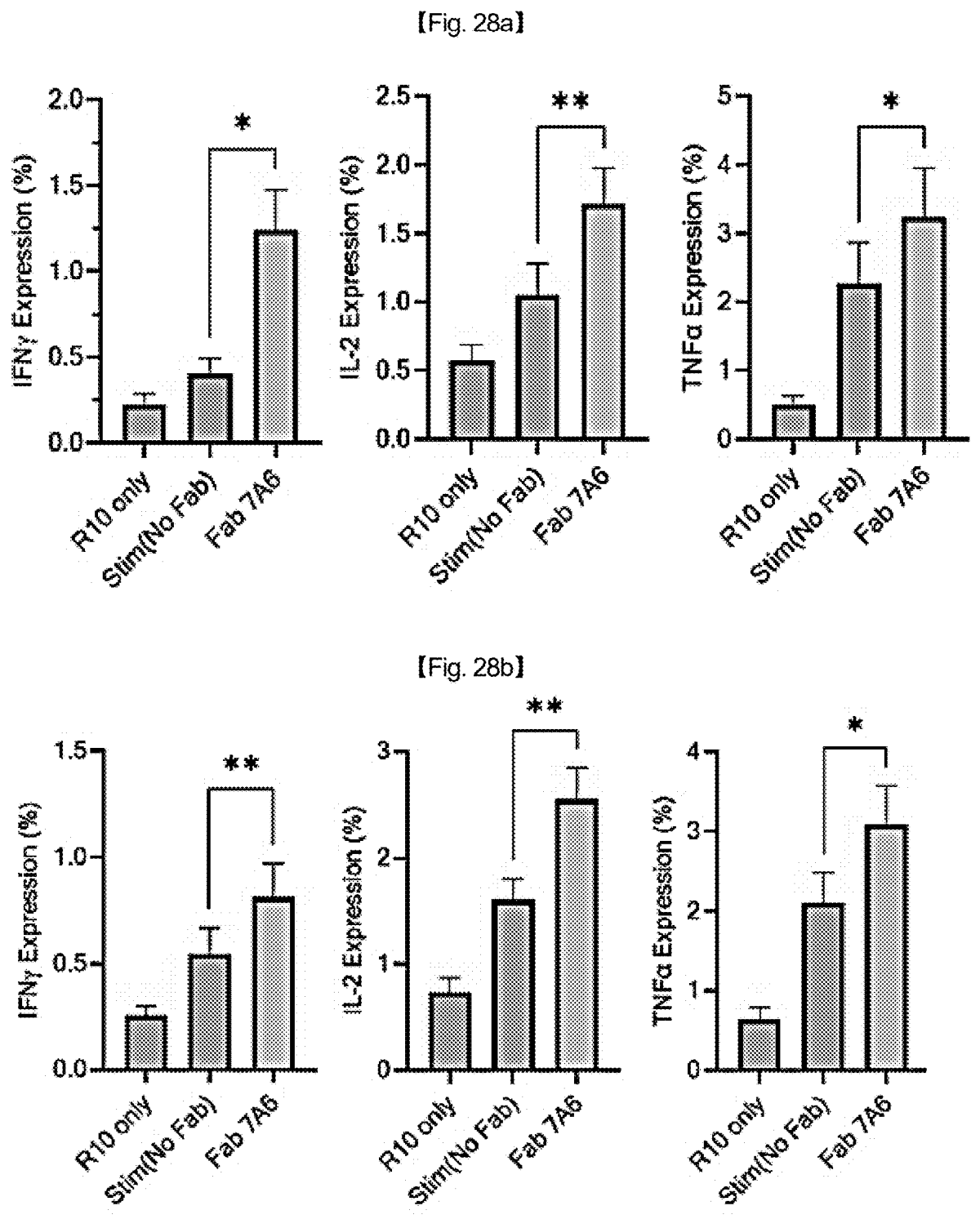

【Fig. 29】
Anti-TIGIT Fab fragments
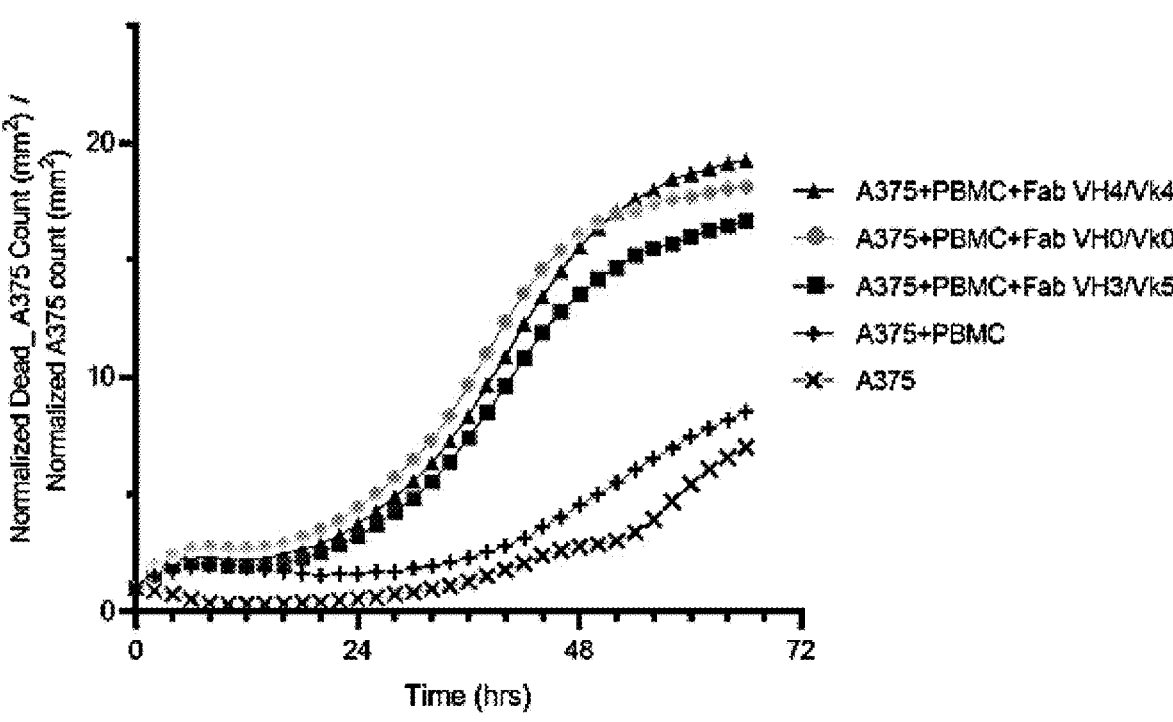
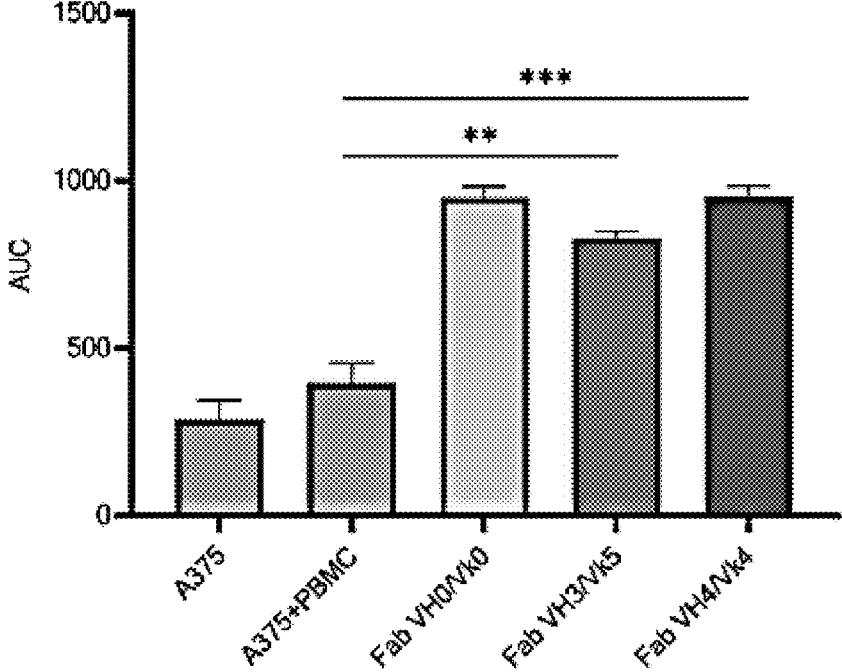

【Fig. 30】
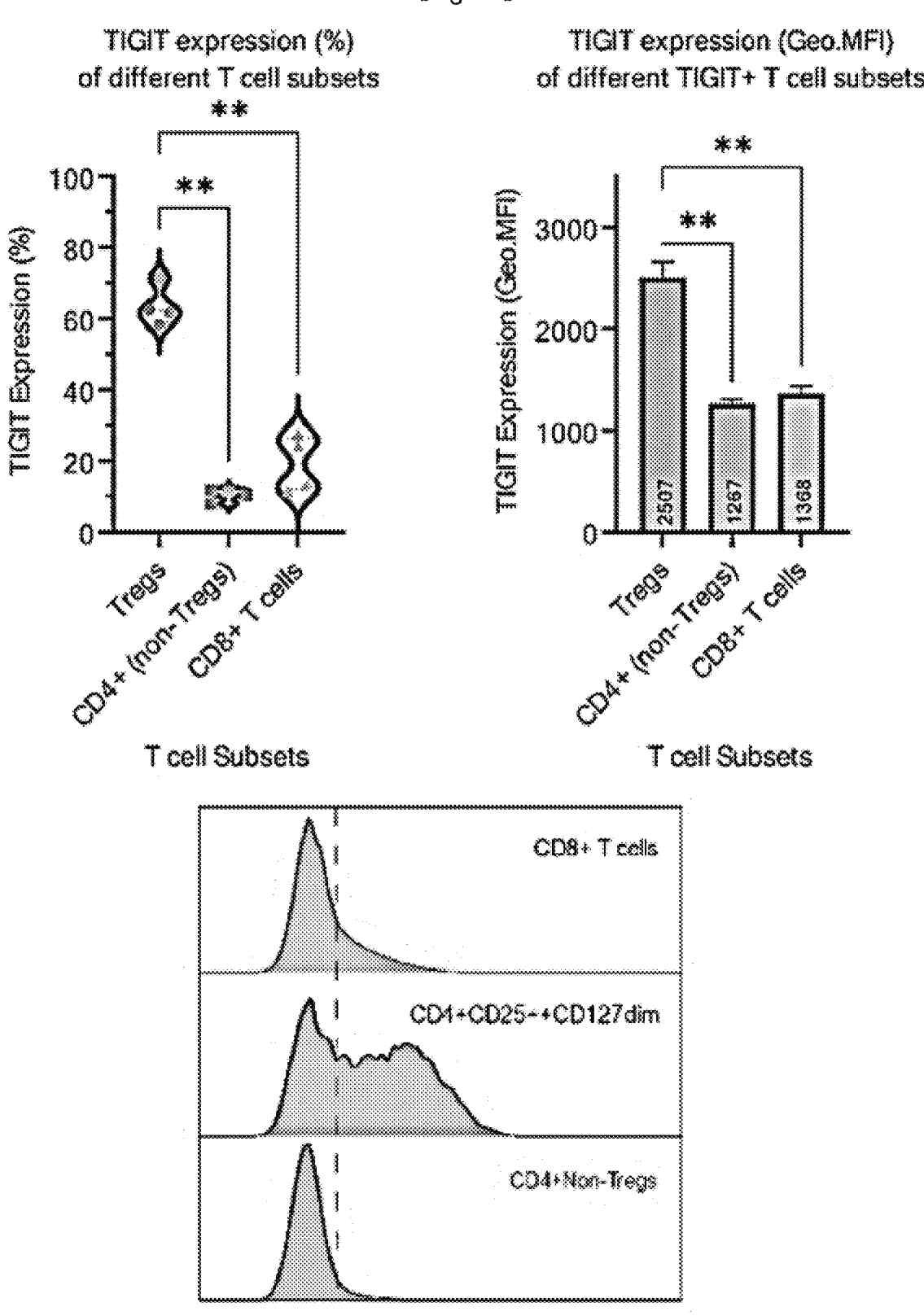

【Fig. 31a】
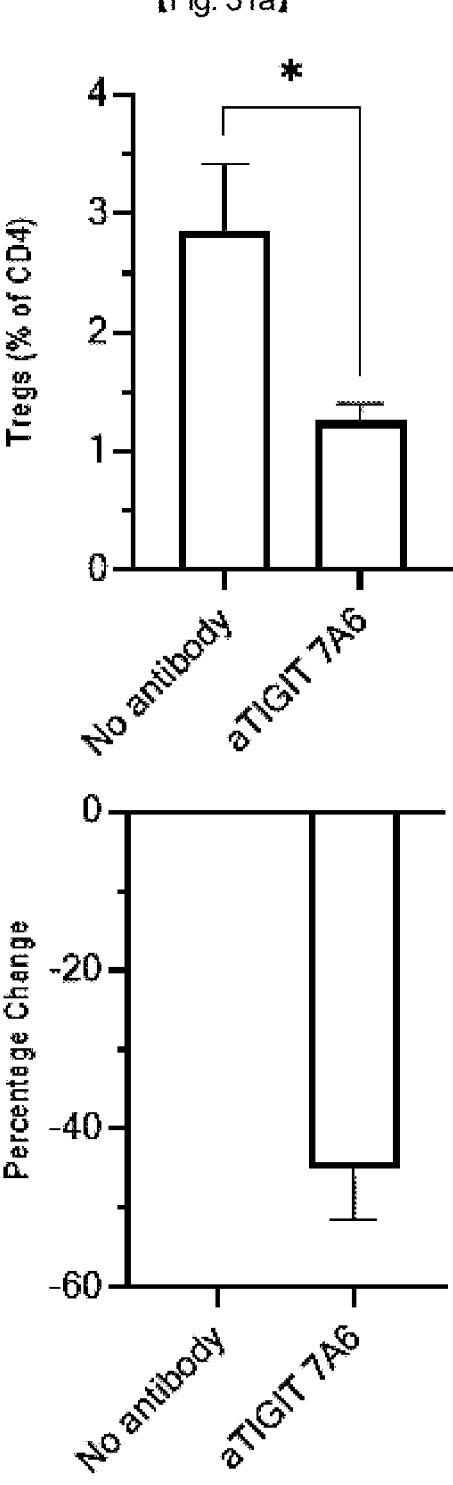

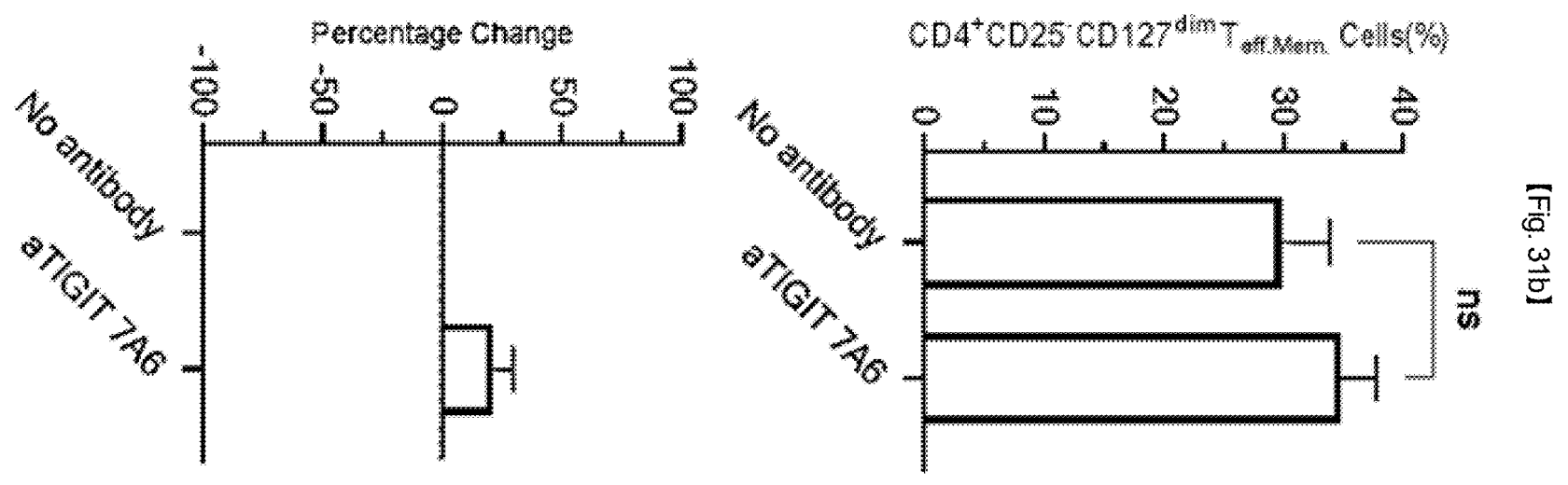

【Fig. 31b】

【Fig. 31c】
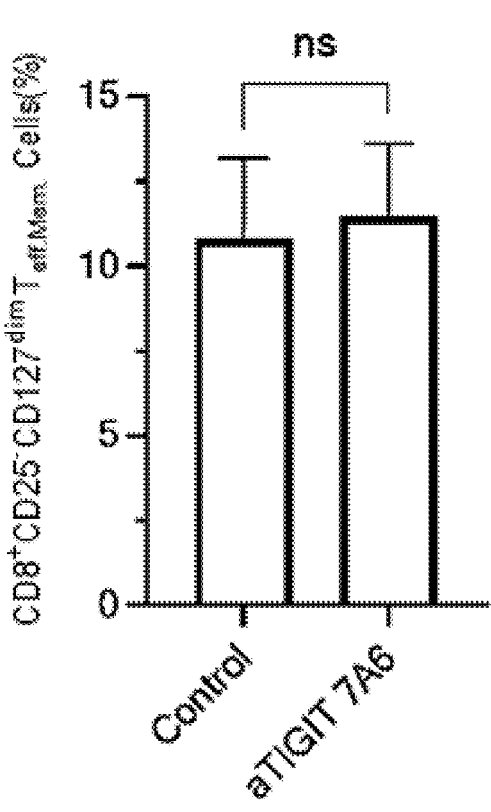
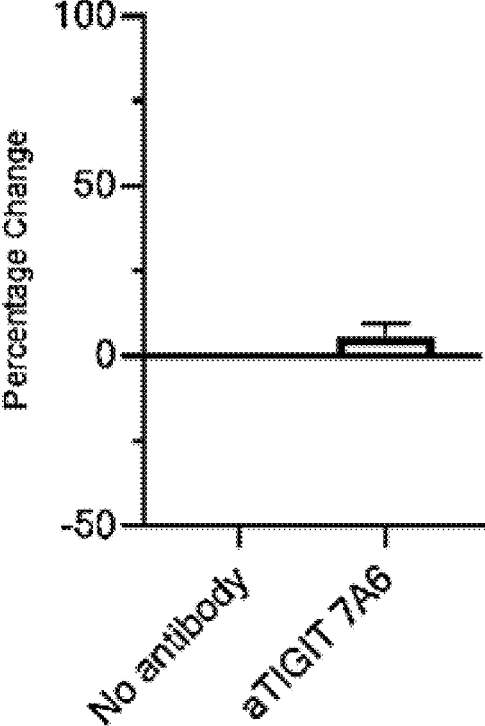

【Fig. 31d】
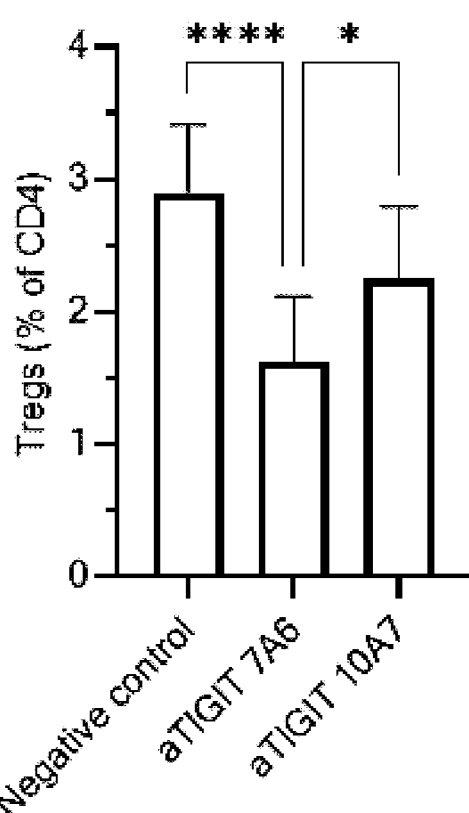

【Fig. 32】
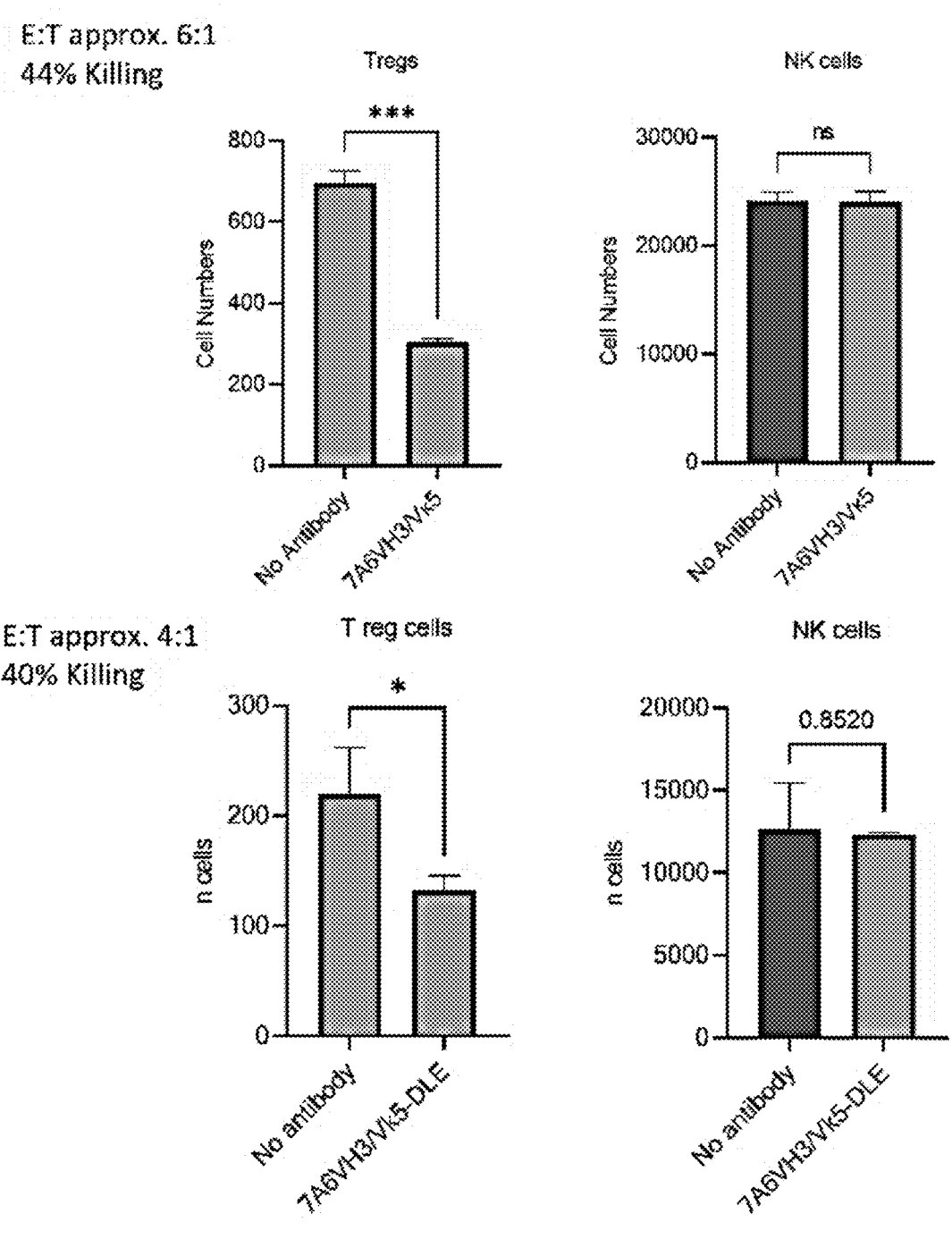

【Fig. 33】
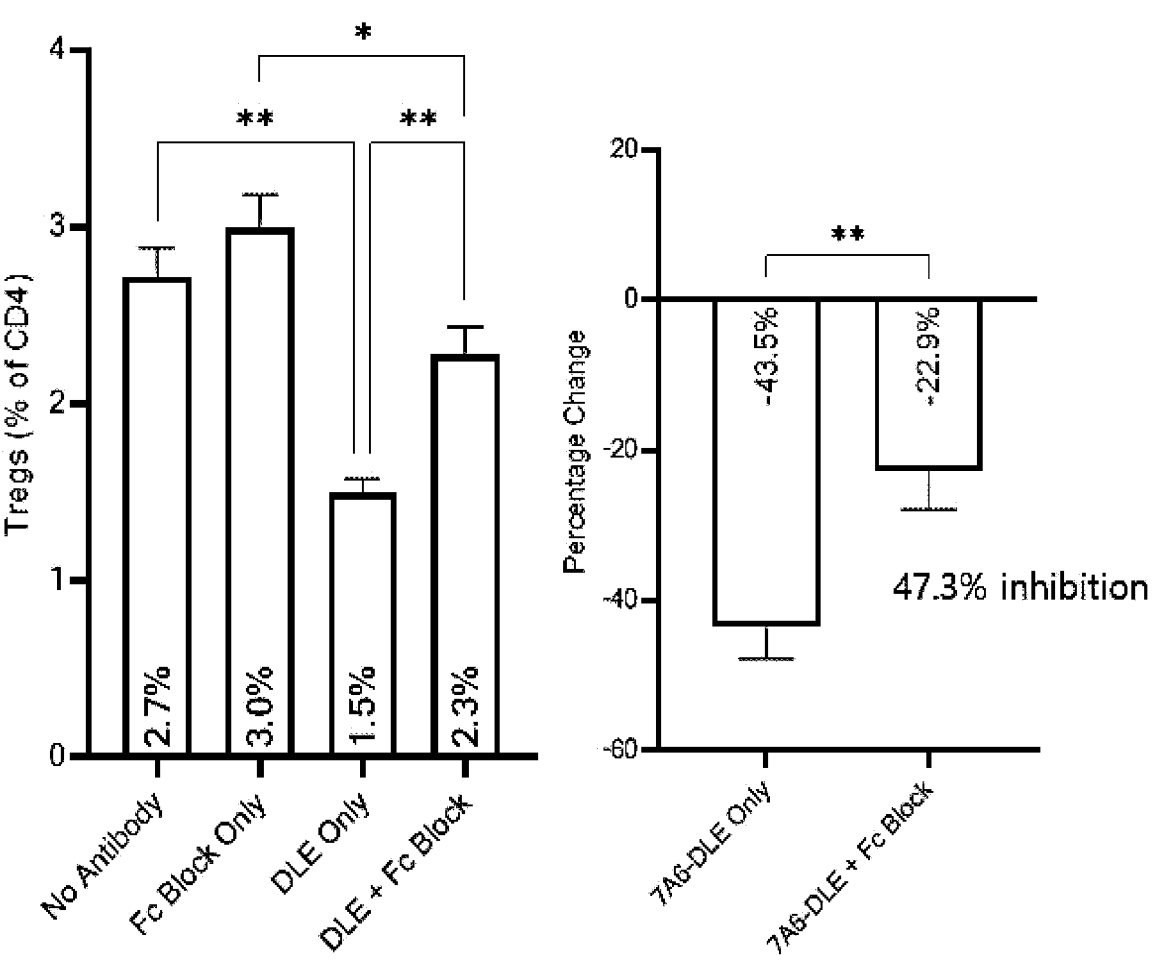
Fc Blockade of VH3/Vκ5-DLE mediated T$_{reg}$ cell depletion
47.3% inhibition 【Fig. 34a】
CD4+T cells
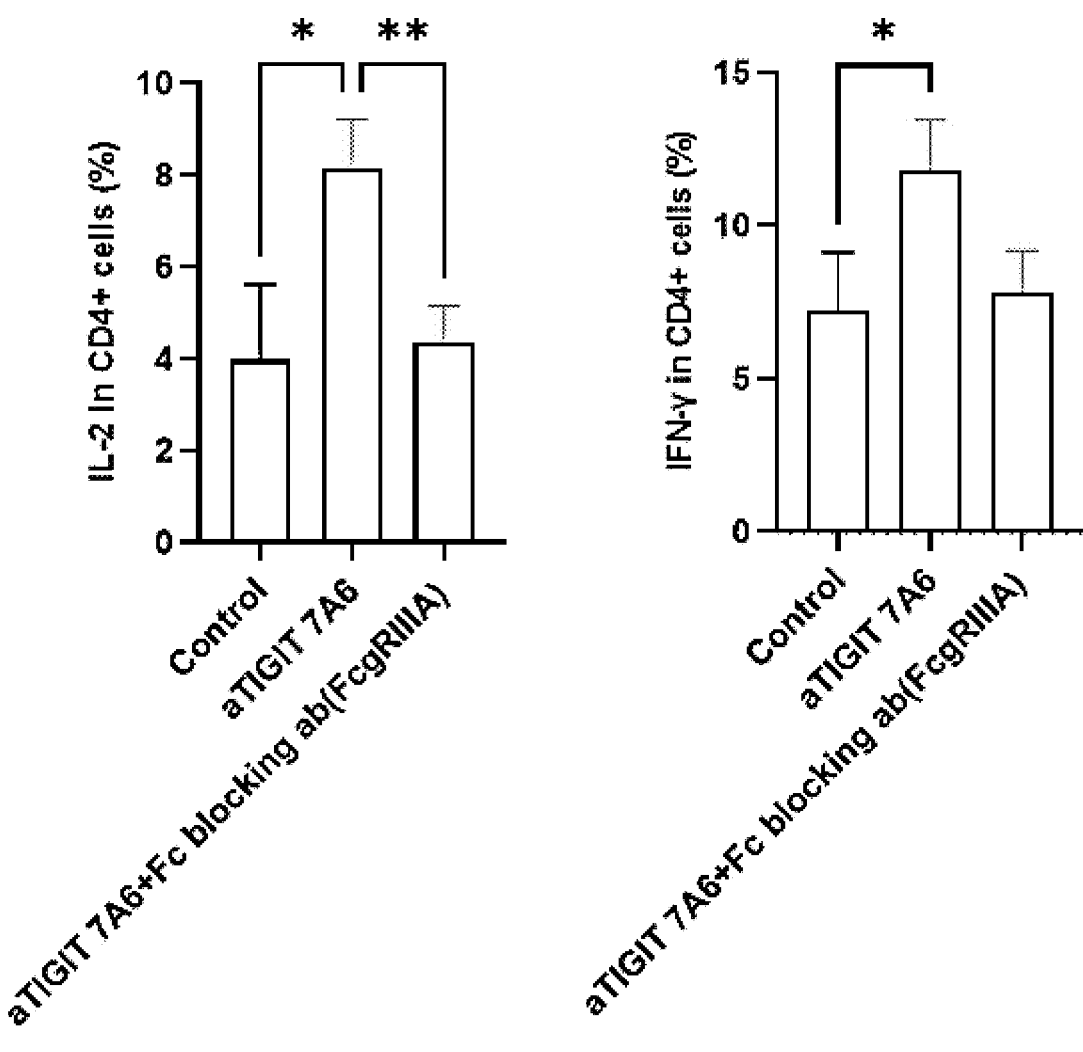

[Fig. 34b]
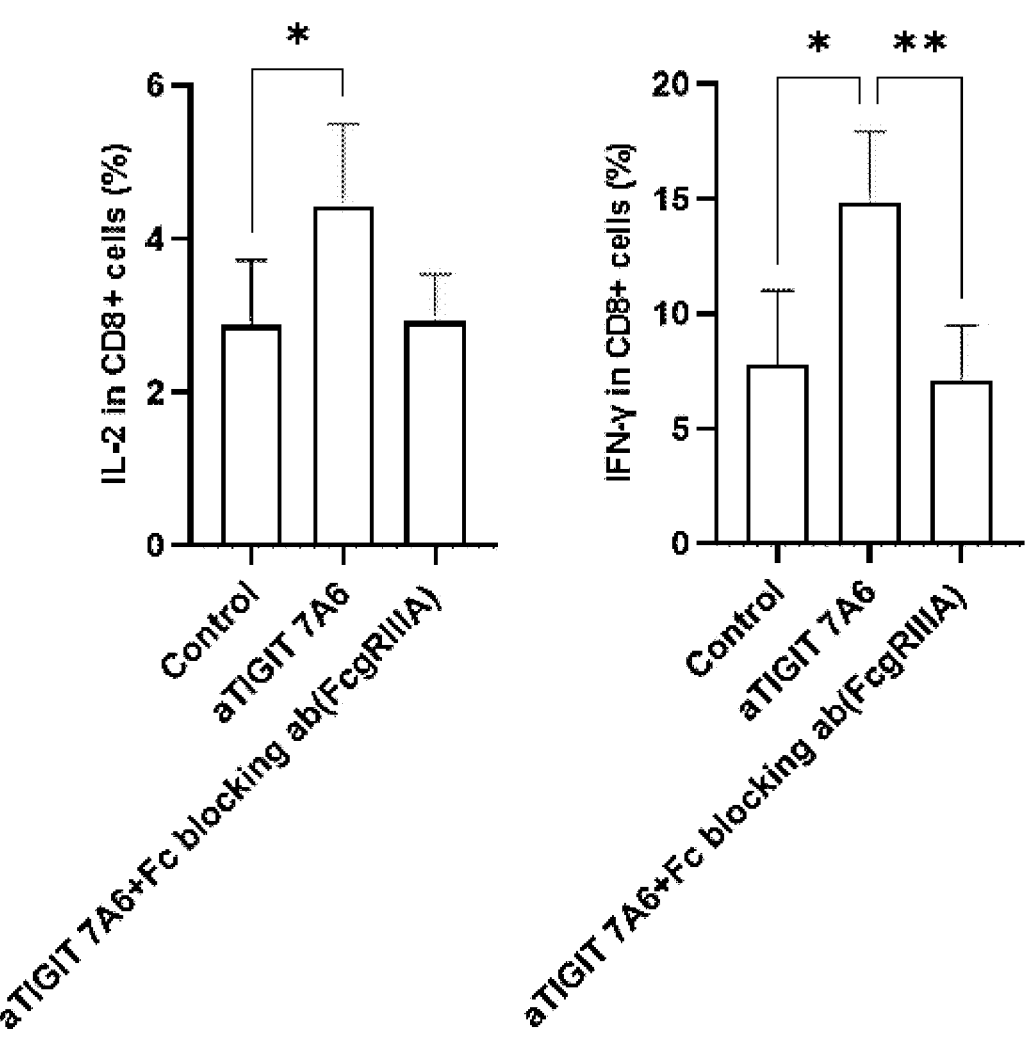
CD8+T cells

SEQUENCE LISTING

<160> NUMBER OF SEQ ID NOS: 31

<210> SEQ ID NO 1
<211> LENGTH: 6
<212> TYPE: PRT
<213> ORGANISM: Artificial Sequence
<220> FEATURE:
<223> OTHER INFORMATION: Synthetic_CDR-H1

<400> SEQUENCE: 1

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic_CDR-H2

<400> SEQUENCE: 2

Tyr Ile Ser Tyr Ser Gly Ser Ala Arg Tyr Asn Pro Ser Leu Lys Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic_CDR-H3

<400> SEQUENCE: 3

Lys Gly Tyr Pro Ala Tyr Phe Ala Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic_CDR-L1, wherein X is K or R
<220> FEATURE:
<221> NAME/KEY: MOD_RES
<222> LOCATION: (1)
<223> OTHER INFORMATION: Xaa is Lys or Arg

<400> SEQUENCE: 4

Xaa Ala Ser Gln Asp Val Ser Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic_CDR-L2

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic_CDR-L3

-continued

```
<400> SEQUENCE: 6

Gln His His Tyr Ser Thr Pro Tyr Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic_CDR-L1

<400> SEQUENCE: 7

Lys Ala Ser Gln Asp Val Ser Thr Ala Val Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic_CDR-L1

<400> SEQUENCE: 8

Arg Ala Ser Gln Asp Val Ser Thr Ala Val Ala
1               5                   10

<210> SEQ ID NO 9
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Ala Arg Tyr Asn Pro Ser Leu
    50                  55                  60

Lys Ser Arg Ile Ser Ile Thr Arg Asp Thr Ser Met Asn Gln Phe Phe
65                  70                  75                  80

Leu Gln Leu Asn Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser
        115

<210> SEQ ID NO 10
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 10

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
```

-continued

```
                20              25                  30
Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Ile Thr Ile Ser Arg Asp Thr Ser Met Asn Gln Phe Ser
65                  70                  75                  80

Leu Lys Leu Asn Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
                100             105                 110

Leu Val Thr Val Ser Ser
            115

<210> SEQ ID NO 11
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 11

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
                20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
                100             105                 110

Leu Val Thr Val Ser Ser
            115

<210> SEQ ID NO 12
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
                20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Val Thr Ile Ser Arg Asp Thr Ser Lys Asn Gln Phe Ser
65                  70                  75                  80
```

-continued

```
Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Synthetic_Heavy chain variable region

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser
        115

<210> SEQ ID NO 15
```

```
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 15

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ser Thr Ala
            20                  25                  30

Val Ala Trp Tyr Gln Gln Lys Pro Gly Gln Ser Pro Glu Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln His His Tyr Ser Thr Pro Tyr
                85                  90                  95

Thr Phe Gly Gly Gly Thr Lys Leu Glu Met Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 16

Asp Ile Val Met Thr Gln Ser His Ser Phe Leu Ser Ala Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ala Pro Glu Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln His His Tyr Ser Thr Pro Tyr
                85                  90                  95

Thr Phe Gly Gln Gly Thr Lys Leu Glu Met Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 17

Asp Ile Val Met Thr Gln Ser Pro Ser Ser Leu Ser Ala Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45
```

```
Tyr Ser Ala Ser Tyr Arg Tyr Thr Gly Val Pro Asp Arg Phe Thr Gly
    50                  55                  60
```

```
Ser Gly Ser Gly Thr Asp Phe Thr Leu Thr Ile Ser Ser Leu Gln Ala
65                  70                  75                  80
```

```
Glu Asp Val Ala Val Tyr Tyr Cys Gln His His Tyr Ser Thr Pro Tyr
                85                  90                  95
```

```
Thr Phe Gly Gln Gly Thr Lys Leu Glu Ile Lys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 18

```
Asp Ile Gln Met Thr Gln Ser Pro Ser Ser Leu Ser Ala Ser Val Gly
1               5                   10                  15
```

```
Asp Arg Val Ser Ile Thr Cys Lys Ala Ser Gln Asp Val Ser Thr Ala
                20                  25                  30
```

```
Val Ala Trp Tyr Gln Gln Lys Pro Gly Gln Ala Pro Arg Leu Leu Ile
            35                  40                  45
```

```
Tyr Ser Ala Ser Tyr Arg Tyr Thr Gly Val Pro Asp Arg Phe Ser Gly
    50                  55                  60
```

```
Ser Gly Ser Gly Thr Asp Phe Thr Leu Thr Ile Ser Ser Leu Gln Ala
65                  70                  75                  80
```

```
Glu Asp Val Ala Val Tyr Tyr Cys Gln His His Tyr Ser Thr Pro Tyr
                85                  90                  95
```

```
Thr Phe Gly Gln Gly Thr Lys Leu Glu Ile Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 19

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Ser Thr Ala
                20                  25                  30
```

```
Val Ala Trp Tyr Gln Gln Lys Pro Gly Gln Ala Pro Arg Leu Leu Ile
            35                  40                  45
```

```
Tyr Ser Ala Ser Tyr Arg Tyr Thr Gly Val Pro Asp Arg Phe Ser Gly
    50                  55                  60
```

```
Ser Gly Ser Gly Thr Asp Phe Thr Leu Thr Ile Ser Ser Leu Gln Ala
65                  70                  75                  80
```

```
Glu Asp Val Ala Val Tyr Tyr Cys Gln His His Tyr Ser Thr Pro Tyr
                85                  90                  95
```

```
Thr Phe Gly Gln Gly Thr Lys Leu Glu Ile Lys
            100                 105
```

<210> SEQ ID NO 20
<211> LENGTH: 107
<212> TYPE: PRT
<213> ORGANISM: Artificial Sequence -continued
<220> FEATURE:
<223> OTHER INFORMATION: Synthetic_Light chain variable region

<400> SEQUENCE: 20

```
Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Thr Pro Tyr
                85                  90                  95

Thr Phe Gly Gln Gly Thr Lys Leu Glu Ile Lys
            100                 105
```

<210> SEQ ID NO 21
<211> LENGTH: 330
<212> TYPE: PRT
<213> ORGANISM: Artificial Sequence
<220> FEATURE:
<223> OTHER INFORMATION: Synthetic_Heavy chain constant region

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
225              230              235              240

Met Thr Lys Asn Gln Val Ser Leu Thr Cys Leu Val Lys Gly Phe Tyr
                 245              250              255

Pro Ser Asp Ile Ala Val Glu Trp Glu Ser Asn Gly Gln Pro Glu Asn
                 260              265              270

Asn Tyr Lys Thr Thr Pro Pro Val Leu Asp Ser Asp Gly Ser Phe Phe
                 275              280              285

Leu Tyr Ser Lys Leu Thr Val Asp Lys Ser Arg Trp Gln Gln Gly Asn
         290              295              300

Val Phe Ser Cys Ser Val Met His Glu Ala Leu His Asn His Tyr Thr
305              310              315              320

Gln Lys Ser Leu Ser Leu Ser Pro Gly Lys
                 325              330
```

<210> SEQ ID NO 22
<211> LENGTH: 107
<212> TYPE: PRT
<213> ORGANISM: Artificial Sequence
<220> FEATURE:
<223> OTHER INFORMATION: Synthetic_Light chain constant region

<400> SEQUENCE: 22

```
Arg Thr Val Ala Ala Pro Ser Val Phe Ile Phe Pro Pro Ser Asp Glu
1                5                10               15

Gln Leu Lys Ser Gly Thr Ala Ser Val Val Cys Leu Leu Asn Asn Phe
         20               25               30

Tyr Pro Arg Glu Ala Lys Val Gln Trp Lys Val Asp Asn Ala Leu Gln
         35               40               45

Ser Gly Asn Ser Gln Glu Ser Val Thr Glu Gln Asp Ser Lys Asp Ser
     50               55               60

Thr Tyr Ser Leu Ser Ser Thr Leu Thr Leu Ser Lys Ala Asp Tyr Glu
65               70               75               80

Lys His Lys Val Tyr Ala Cys Glu Val Thr His Gln Gly Leu Ser Ser
                 85               90               95

Pro Val Thr Lys Ser Phe Asn Arg Gly Glu Cys
                 100              105
```

<210> SEQ ID NO 23
<211> LENGTH: 354
<212> TYPE: DNA
<213> ORGANISM: Artificial Sequence
<220> FEATURE:
<223> OTHER INFORMATION: Synthetic_7A6 heavy chain variable region
    coding DNA

<400> SEQUENCE: 23

```
gatgtgcagc ttcaggagtc gggacctggc ctggtgaaac cttctcagtc tctgtccctc    60
acctgcactg tcactggcta ctcaatcacc agtgattatg cctggaactg gatccggcag   120
tttccaggaa acaaactgga gtggatgggc tacataagct acagtggtag cgctcgctac   180
aacccatctc tcaaaagtcg aatctctatc actcgagaca catccatgaa ccagttcttc   240
ctgcagttga attctgtgac tgctgaggac acagccacat attactgtgc aagaaagggg   300
taccctgcct actttgctta ctggggccaa gggactctgg tcactgtctc tgca          354
```

<210> SEQ ID NO 24
<211> LENGTH: 321
<212> TYPE: DNA
<213> ORGANISM: Artificial Sequence -continued

```
<220> FEATURE:
<223> OTHER INFORMATION: Synthetic_7A6 light chain variable region
      coding DNA

<400> SEQUENCE: 24
gacattgtga tgacccagtc tcacaaattc atgtccacat cagtaggaga cagggtcagc      60
atctcctgca aggccagtca ggatgtgagt actgctgtag cctggtatca acagaaacca     120
ggacaatctc ctgaactact gatttactcg gcatcctacc ggtacactgg agtccctgat     180
cgcttcactg gcagtggatc tgggacggat ttcactttca ccatcagcag tgtgcaggct     240
gaagacctgg cagtttatta ctgtcagcat cattatagta ctccgtacac gttcggaggg     300
gggaccaagc tggaaatgaa a                                               321

<210> SEQ ID NO 25
<211> LENGTH: 447
<212> TYPE: PRT
<213> ORGANISM: Artificial Sequence
<220> FEATURE:
<223> OTHER INFORMATION: Synthetic_7A6 VH3/Vk5-DLE heavy chain

<400> SEQUENCE: 25

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
                20                  25                  30

Tyr Ala Trp Asn Trp Ile Arg Gln Pro Pro Gly Lys Gly Leu Glu Trp
            35                  40                  45

Met Gly Tyr Ile Ser Tyr Ser Gly Ser Ala Arg Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
        435                 440                 445
```

<210> SEQ ID NO 26
<211> LENGTH: 448
<212> TYPE: PRT
<213> ORGANISM: Artificial Sequence
<220> FEATURE:
<223> OTHER INFORMATION: Synthetic_VH3/Vk5 N298A heavy chain

<400> SEQUENCE: 26

```
Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
                20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190
```

-continued

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 27
<211> LENGTH: 448
<212> TYPE: PRT
<213> ORGANISM: Artificial Sequence
<220> FEATURE:
<223> OTHER INFORMATION: Synthetic_7A6 VH3/Vk5 AAA heavy chain

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
        20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
                100                 105                 110

-continued

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ala Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Ala Ala Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 28
<211> LENGTH: 448
<212> TYPE: PRT
<213> ORGANISM: Artificial Sequence
<220> FEATURE:
<223> OTHER INFORMATION: Synthetic_7A6 VH3/Vk5 LALAPG heavy chain

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30
```

```
Tyr Ala Trp Asn Trp Ile Arg Gln Pro Pro Gly Lys Gly Leu Glu Trp
        35                  40                  45

Met Gly Tyr Ile Ser Tyr Ser Gly Ser Ala Arg Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Glu Asp Thr Ala Thr Tyr Tyr Cys
                85                  90                  95

Ala Arg Lys Gly Tyr Pro Ala Tyr Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 29
<211> LENGTH: 214
<212> TYPE: PRT
<213> ORGANISM: Artificial Sequence
<220> FEATURE:
<223> OTHER INFORMATION: Synthetic_Light chain of 7A6 VH3/Vk5 mutants

<400> SEQUENCE: 29

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Thr Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 30
<211> LENGTH: 244
<212> TYPE: PRT
<213> ORGANISM: Artificial Sequence
<220> FEATURE:
<223> OTHER INFORMATION: Synthetic_human TIGIT

<400> SEQUENCE: 30

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
                20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
        50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

-continued

```
Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly
```

```
<210> SEQ ID NO 31
<211> LENGTH: 20
<212> TYPE: PRT
<213> ORGANISM: Artificial Sequence
<220> FEATURE:
<223> OTHER INFORMATION: Synthetic_Epitope region on human TIGIT

<400> SEQUENCE: 31

Thr Ala Gln Val Thr Gln Val Asn Trp Glu Gln Gln Asp Gln Leu Leu
1               5                   10                  15

Ala Ile Cys Asn
            20
```

ANTI-TIGIT ANTIBODIES AND USE THEREOF

CROSS-REFERENCE TO RELATED APPLICATION(S)

This application claims the benefits of KR 10-2021-0060014 filed on May 10, 2021 with the Korean Intellectual Property Office, the entire disclosure of which is herein incorporated by reference.

Technical Field

Disclosed are a novel anti-TIGIT antibody and uses thereof for immunopotentiation and for preventing and/or treating cancer and immune-related diseases.

SEQUENCE LISTING

This application contains a Sequence Listing which has been submitted electronically and incorporated by reference in its entirety. The sequence listing, submitted Jun. 24, 2024, is named "18290171 2 1.txt" and is 38, 209 bytes in size.

Background Art

Cancer immunotherapy is a method of treating cancer using the body's immune response, and is referred to as the fourth treatment for cancer, following chemotherapy, surgical therapy, and radiotherapy. Cancer immunotherapy requires a mechanism that activates the immune system to increase recognition and response to tumor cells. Activation of the immune system involves a complex mechanism that includes the function of various cells such as antigen-presenting cells, which are crucial for initiating antigen-specific responses, and effector cells responsible for the destruction of tumor cells.

Representative of the effector cells are cytotoxic T cells.

Meanwhile, T cell immunoglobulin and ITIM (immuno-receptor tyrosine-based inhibition motif) domain (TIGIT), also referred to as WUCAM, VSIG9, or Vstm3, is a co-inhibitory receptor preferentially expressed not only on NK, CD8+, and CD4+ T cells but also on regulatory T cells (Treg). TIGIT is a transmembrane protein that encompasses an intracellular ITIM domain, a transmembrane domain, and an immunoglobulin variable domain.

TIGIT expression is elevated in tumor infiltrating lymphocytes (TIL) and in disease conditions such as infections. TIGIT expression can be a marker for exhausted T cells with lower effector functions compared to TIGIT-negative cells. Furthermore, Treg cells expressing TIGIT show enhanced immunosuppressive activity compared to TIGIT negative Treg populations.

Based on these findings, drugs that counteract TIGIT (e.g., antagonistic anti-TIGIT antibodies) are anticipated to induce immune system activation and enhance immune responses in disease conditions like cancer, thereby presenting favorable therapeutic effects.

DISCLOSURE

Technical Problem

Provided are an anti-TIGIT antibody binding to TIGIT and a pharmaceutical use thereof.

An aspect provides an anti-TIGIT antibody binding to TIGIT or an antigen-binding fragment thereof.

The anti-TIGIT antibody or antigen-binding fragment thereof may include:

a heavy chain complementarity determining region (CDR) composed of a polypeptide including the amino acid sequence of SEQ ID NO: 1 (CDR-H1), a polypeptide including the amino acid sequence of SEQ ID NO: 2 (CDR-H2), and a polypeptide including the amino acid sequence of SEQ ID NO: 3 (CDR-H3), or a heavy chain variable region including the heavy chain complementarity determining region; and a light chain complementarity determining region (CDR) composed of a polypeptide including the amino acid sequence of SEQ ID NO: 4 (CDR-L1), a polypeptide including the amino acid sequence of SEQ ID NO: 5 (CDR-L2), and a polypeptide including the amino acid sequence of SEQ ID NO: 6 (CDR-L3), or a light chain variable region including the light chain complementarity determining region In an embodiment, the anti-TIGIT antibody or the antigen-binding fragment thereof may include:

a heavy variable region including the amino acid sequence of SEQ ID NO: 9, 10, 11, 12, 13, or 14; and a light chain variable region including the amino acid sequence of SEQ ID NO: 15, 16, 17, 18, 19, or 20.

Another aspect provides an immunopotentiator or an immunopotent pharmaceutical composition, each including the anti-TIGIT antibody or antigen-binding fragment thereof as an active ingredient.

Another aspect provides a pharmaceutical composition including the anti-TIGIT antibody or antigen-binding fragment thereof as an active ingredient for prevention and/or treatment of an immune-related disease.

Another aspect provides an anticancer agent or a pharmaceutical composition for prevention and/or treatment of cancer, each including the anti-TIGIT antibody or antigen-binding fragment thereof as an active ingredient.

Another aspect provides an immunopotentiating method including a step of administering a pharmaceutically effective amount of the anti-TIGIT antibody or antigen-binding fragment thereof to a subject in need of immunopotentiation.

Another aspect provides a method for preventing and/or treating an immune-related disease, the method including a step of administering a pharmaceutically effective amount of the anti-TIGIT antibody or antigen-binding fragment thereof to a subject in need of immune-related disease prevention and/or treatment.

Another aspect provides a method for preventing and/or treating cancer, the method including a step of administering a pharmaceutically effective amount of the anti-TIGIT antibody or antigen-binding fragment thereof to a subject in need of cancer prevention and/or treatment.

Another aspect provides a use of the anti-TIGIT antibody or antigen-binding fragment thereof for immunopotentiation or for preparing an immunopotentiator.

Another aspect provides a use of the anti-TIGIT antibody or antigen-binding fragment thereof for preventing and/or treating an immune-related disease or for preparing a drug for prevention and/or treatment of an immune-related disease.

Another aspect provides a use of the anti-TIGIT antibody or antigen-binding fragment thereof for preventing and/or treating cancer or for preparing a drug for prevention and/or treatment of cancer.

According to an embodiment, in the pharmaceutical compositions, methods, and uses provided herein, the anti-TIGIT antibody or antigen-binding fragment thereof may be used in combination of an immune checkpoint protein, for example, a drug (antagonist) targeting either or both of PD-1 and PD-L1. The drug administrable in combination may be an anti PD-1 antibody, an anti-PD-L1 antibody, or both of them, but is not limited thereto.

Another aspect provides a nucleic acid molecule encoding the heavy chain complementarity determining region, heavy chain variable region, or heavy chain of the anti-TIGIT antibody.

Another aspect provides a nucleic acid molecule encoding the light chain complementarity determining region, light chain variable region, or light chain of the anti-TIGIT antibody.

Another aspect provides a recombinant vector carrying a nucleic acid molecule coding for the heavy chain complementarity determining region, heavy chain variable region, or heavy chain of the anti-TIGIT antibody and a nucleic acid molecule coding for the light chain complementarity determining region, light chain variable region, or light chain of the anti-TIGIT antibody in combination, or separate recombinant vectors carrying a nucleic acid molecule coding for the heavy chain complementarity determining region, heavy chain variable region, or heavy chain of the anti-TIGIT antibody and a nucleic acid molecule coding for the light chain complementarity determining region, light chain variable region, or light chain of the anti-TIGIT antibody, respectively. The recombinant vectors may be expression vectors for expressing the nucleic acid molecules.

Another aspect provides a recombinant cell anchoring the recombinant vector thereat.

Another aspect provides a method for producing the anti-TIGIT antibody or antigen-binding fragment thereof, the method including a step of expressing the nucleic acid molecules in a host cell. The step of expressing the nucleic acid molecule may be a step in which a cell anchoring the nucleic acid molecules or a recombinant vector carrying same is cultured. The method may further include a step of separating and/or purifying an antibody from the medium after the expressing step.

Technical Solution

Provided herein an anti-TIGIT antibody binding to TIGIT or an antigen-binding fragment, and medicinal uses thereof. The anti-TIGIT antibody or the antigen-binding fragment thereof functions to activate immunity (e.g., enhancement of effector T cell function, regulation of Treg activity, increased cytokine secretion, etc.) by blocking the action of TIGIT, thus finding applications as various immune activators and/or immunotherapeutics.

Below, a detailed description will be given of the present disclosure.

Antibody or Antigen-Binding Fragment

An aspect provides an anti-TIGIT antibody binding to TIGIT or an antigen-binding fragment thereof.

The anti-TIGIT antibody or antigen-binding fragment thereof may include:

a polypeptide including the amino acid sequence of SEQ ID NO: 1 (CDR-H1), a polypeptide including the amino acid sequence of SEQ ID NO: 2 (CDR-H2), a polypeptide including the amino acid sequence of SEQ ID NO: 3 (CDR-H3), a polypeptide including the amino acid sequence of SEQ ID NO: 4 (CDR-L1), a polypeptide including the amino acid sequence of SEQ ID NO: 5 (CDR-L2), and

4 a polypeptide including the amino acid sequence of SEQ ID NO: 6 (CDR-L3).

The polypeptide including the amino acid sequence of SEQ ID NO: 4 (CDR-L1) may include the amino acid sequence of SEQ ID NO: 7 or SEQ ID NO: 8.

Herein, the complementarity determining region (CDR) is generally determined as defined according to the kabat system.

In an embodiment, the six CDRs (CDR-L1, CDR-L2, CDR-L3, CDR-H1, CDR-H2, and CDR-H3) that may be included in the anti-TIGIT antibody or antigen-binding fragment thereof provided herein are summarized in Table 1, below.

TABLE 1

| | Sequence | SEQ ID NO: |
|---|---|---|
| CDR-H1 | SDYAWN | 1 |
| CDR-H2 | YISYSGSARYNPSLKS | 2 |
| CDR-H3 | KGYPAYFAY | 3 |
| CDR-L1 | XASQDVSTAVA (X = K or R) | 4 |
| CDR-L1 | KASQDVSTAVA | 7 |
| CDR-L1 | RASQDVSTAVA | 8 |
| CDR-L2 | SASYRYT | 5 |
| CDR-L3 | QHHYSTPYT | 6 |

(In Table 1, CDR-H1, CDR-H2, and CDR-H3 each stand for a heavy chain complementarity determining region and CDR-L1, CDR-L2, and CDR-L3 each stand for a light chain complementarity determining region)

In an embodiment, the anti-TIGIT antibody or antigen-binding fragment thereof may include:

a heavy chain variable region including CDR-H1 of SEQ ID NO: 1, CDR-H2 of SEQ ID NO: 2, and CDR-H3 of SEQ ID NO:3, and a light chain variable region including CDR-L1 of SEQ ID NO: 4 (i.e., SEQ ID NO: 7 or SEQ ID NO: 8), CDR-L2 of SEQ ID NO: 5, and CDR-L3 of SEQ ID NO: 6.

More specifically, the anti-TIGIT antibody or the antigen-binding fragment thereof may include:

a heavy chain variable region including the amino acid sequence of SEQ ID NO: 9, 10, 11, 12, 13, or 14; and a light chain variable region including the amino acid sequence of SEQ ID NO: 15, 16, 17, 18, 19, or 20.

In an embodiment, the anti-TIGIT antibody or the antigen-binding fragment thereof may include:

a heavy chain variable region including the amino acid sequence of SEQ ID NO: 9, and a light chain variable region including the amino acid sequence of SEQ ID NO: 15;

a heavy chain variable region including the amino acid sequence of SEQ ID NO: 10, and a light chain variable region including the amino acid sequence of SEQ ID NO: 16;

a heavy chain variable region including the amino acid sequence of SEQ ID NO: 11, and a light chain variable region including the amino acid sequence of SEQ ID NO: 17;

a heavy chain variable region including the amino acid sequence of SEQ ID NO: 12, and a light chain variable region including the amino acid sequence of SEQ ID NO: 18;

a heavy chain variable region including the amino acid sequence of SEQ ID NO: 13, and a light chain variable region including the amino acid sequence of SEQ ID NO: 19; or a heavy chain variable region including the amino acid sequence of SEQ ID NO: 14, and a light chain variable region including the amino acid sequence of SEQ ID NO: 20.

Depending on the situation (for example, when produced recombinantly), the heavy chain variable region and/or light chain variable region may further include an appropriate signal sequence at the N-terminus.

Amino acid sequences of the heavy chain variable region and light chain variable region that may be included in the anti-TIGIT antibody or antigen-binding fragment thereof provided herein are given in Table 2, below:

consecutively positioned) selected from among the region of amino acid residues 51-70 (TAQVTQVNWEQQDQLLA-ICN; SEQ ID NO: 31) in human TIGIT protein (NCBI Reference Sequence NP_776160.2; UniProtKB/SwissProt Q495A1-1), but with no limitations thereto.

```
        [Human TIGIT protein (SEQ ID NO: 30)]
  1 MRWCLLLIWA QGLRQAPLAS GMMTGTIETT

GNISAEKGGS IILQCHLSST TAQVTQVNWE

61 QQDQLLAICN ADLGWHISPS FKDRVAPGPG

LGLTLQSLTV NDTGEYFCIY HTYPDGTYTG
```

TABLE 2

| Variable region | Amino acid sequence (N→C) | SEQ ID NO: |
|---|---|---|
| Heavy chain variable region | DVQLQESGPGLVKPSQSLSLTCTVTGYSITSDYAWNWIRQFPGNK LEWMGYISYSGSARYNPSLKSRISITRDTSMNQFFLQLNSVTAED TATYYCARKGYPAYFAYWGQGTLVTVSS | 9 |
| Heavy chain variable region | DVQLQESGPGLVKPSQTLSLTCTVTGYSITSDYAWNWIRQPPGKG LEWMGYISYSGSARYNPSLKSRITISRDTSMNQFSLKLNSVTAED TATYYCARKGYPAYFAYWGQGTLVTVSS | 10 |
| Heavy chain variable region | DVQLQESGPGLVKPSQTLSLTCTVTGYSITSDYAWNWIRQPPGKG LEWMGYISYSGSARYNPSLKSRITISRDTSKNQFSLKLSSVTAED TATYYCARKGYPAYFAYWGQGTLVTVSS | 11 |
| Heavy chain variable region | QVQLQESGPGLVKPSQTLSLTCTVTGYSITSDYAWNWIRQPPGKG LEWMGYISYSGSARYNPSLKSRVTISRDTSKNQFSLKLSSVTAED TATYYCARKGYPAYFAYWGQGTLVTVSS | 12 |
| Heavy chain variable region | QVQLQESGPGLVKPSQTLSLTCTVTGYSITSDYAWNWIRQPPGKG LEWMGYISYSGSARYNPSLKSRVTISRDTSKNQFSLKLSSVTAAD TAVYYCARKGYPAYFAYWGQGTLVTVSS | 13 |
| Heavy chain variable region | QVQLQESGPGLVKPSQTLSLTCTVTGYSITSDYAWNWIRQPPGKG LEWMGYISYSGSARYNPSLKSRVTISVDTSKNQFSLKLSSVTAAD TAVYYCARKGYPAYFAYWGQGTLVTVSS | 14 |
| Light chain variable region | DIVMTQSHKFMSTSVGDRVSISCKASQDVSTAVAWYQQKPGQSP ELLIYSASYRYTGVPDRFTGSGSGTDFTFTISSVQAEDLAVYYC QHHYSTPYTFGGGTKLEMK | 15 |
| Light chain variable region | DIVMTQSHSFLSASVGDRVSITCKASQDVSTAVAWYQQKPGQAPE LLIYSASYRYTGVPDRFTGSGSGTDFTLTISSLQAEDVAVYYCQH HYSTPYTFGQGTKLEMK | 16 |
| Light chain variable region | DIVMTQSPSSLSASVGDRVSITCKASQDVSTAVAWYQQKPGQAPR LLIYSASYRYTGVPDRFTGSGSGTDFTLTISSLQAEDVAVYYCQH HYSTPYTFGQGTKLEIK | 17 |
| Light chain variable region | DIQMTQSPSSLSASVGDRVSITCKASQDVSTAVAWYQQKPGQAP RLLIYSASYRYTGVPDRFSGSGSGTDFTLTISSLQAEDVAVYYC QHHYSTPYTFGQGTKLEIK | 18 |
| Light chain variable region | DIQMTQSPSSLSASVGDRVTITCRASQDVSTAVAWYQQKPGQAPR LLIYSASYRYTGVPDRFSGSGSGTDFTLTISSLQAEDVAVYYCQH HYSTPYTFGQGTKLEIK | 19 |
| Light chain variable region | DIQMTQSPSSLSASVGDRVSITCKASQDVSTAVAWYQQKPGQAP RLLIYSASYRYTGVPDRFSGSGSGTDFTLTISSLQPEDFATYYC QHHYSTPYTFGQGTKLEIK | 20 |

(In Table 2, the underlined regions represent CDR1, CDR2, and CDR3 in heavy and light chains, sequentially)

In an embodiment, the anti-TIGIT antibody or antigen-binding fragment thereof provided herein is bonded to TIGIT protein, for example, one or more amino acids (e.g.,

```
        -continued
121 RIFLEVLESS VAEHGARFQI PLLGAMAATL

VVICTAVIVV VALTRKKKAL RIHSVEGDLR
```

-continued

```
181 RKSAGQEEWS PSAPSPPGSC VQAEAAPAGL

CGEQRGEDCA ELHDYFNVLS YRSLGNCSFF

241 TETG
```

As described herein, the term "antibody" may refer to a protein that specifically binds to a specific antigen, and may be a protein produced by stimulation of an antigen in the immune system, or a protein produced by chemical synthesis or recombinant production, with no specific limitation. The antibody may be non-naturally occurring, for example, produced by recombinant or synthetic production. The antibody may be an animal antibody (e.g., a mouse antibody, etc.), a chimeric antibody, a humanized antibody, or a human antibody. The antibody may be a monoclonal or polyclonal antibody.

In the anti-TIGIT antibody or antigen-binding fragment thereof provided herein, the portion, except for the heavy-chain CDR and light-chain CDR portions or the heavy-chain variable and light-chain variable regions as defined above, may be derived from any subtype of immunoglobulin (e.g., IgA, IgD, IgE, IgG (IgG1, IgG2, IgG3, IgG4), IgM, and the like), and, for example, derived from the framework portions, and/or light-chain constant region and/or heavy-chain constant region. In an embodiment, the anti-TIGIT antibody provided herein may be an antibody in a form of human IgG, for example, IgG1, IgG2, IgG3, or IgG4, but not be limited thereto.

An intact antibody (e.g., IgG type) has a structure with two full-length light chains and two full-length heavy chains, in which each light chain is linked to a corresponding heavy chain via a disulfide bond. The constant region of an antibody is divided into a heavy-chain constant region and a light-chain constant region. The heavy-chain constant region is of a gamma ($\gamma$), mu ($\mu$), alpha ($\alpha$), delta ($\delta$), or epsilon ($\varepsilon$) type, and has gamma1 ($\gamma$1), gamma2 ($\gamma$2), gamma3 ($\gamma$3), gamma4 ($\gamma$4), alpha1 ($\alpha$1) or alpha2 ($\alpha$2) as its subclass. The light chain constant region is of either a kappa ($\kappa$) or lambda ($\lambda$) type.

In an embodiment, the anti-TIGIT antibody provided herein may include a constant region of IgG as the heavy chain constant region and a kappa constant region as the light chain constant region, but with no limitations thereto.

In an embodiment, the constant region of IgG (e.g., human IgG1) may be a wild type. In another embodiment, the constant region of IgG may be a variant that has at least one mutation, on human IgG1, selected from the group consisting of S240D (S at position 240 substituted by D, hereinafter, amino acid mutations are expressed in the same manner), A331L, I333E, N298A, S299A, E334A, K335A, L235A, L236A, and P330G. For example, the constant region may be a variant with the following mutation:

(1) S240D, A331L, and I333E;
(2) N298A;
(3) S299A, E334A, and K335A; or
(4) L235A, L236A, and P330G.

As used herein, the term "heavy chain" may be intended to encompass a full-length heavy chains and fragments thereof, wherein the full-length heavy chain includes a variable region $V_H$ including amino acid sequences sufficient to provide specificity to antigens, three constant regions $C_{H1}$, $C_{H2}$, and $C_{H3}$, and a hinge. The term "light chain" is intended to encompass full-length light chains and fragments thereof, wherein the full-length light chain includes a variable region $V_L$ including amino acid sequences sufficient to provide specificity to antigens, and a constant region $C_L$.

The term "complementarity determining region" (CDR) refers to a portion that confers antigen-binding specificity in a variable region of an antibody and refer to an amino acid sequence found in a hypervariable region of a heavy chain or a light chain of immunoglobulin. The heavy and light chains may each include three CDRs (CDRH1, CDRH2, and CDRH3; and CDRL1, CDRL2, and CDRL3). The CDR may provide contacting residues that play an important role in the binding of an antibody to its antigen or an epitope of the antigen. As used herein, the terms "specifically binding" and "specifically recognizing" may have the same general meaning as known to one of ordinary skill in the art, and indicate that an antibody and an antigen specifically interact with each other to lead to an immunological reaction.

The complementarity determining region (CDR) described herein is determined as defined according to the kabat system.

In this disclosure, unless particularly stated, the term "antibody" may be understood to include an antigen-binding fragment of an antibody having antigen-binding ability.

The term "antigen-binding fragment" used herein may refer to a polypeptide in any type, which includes a portion (e.g., 6 CDRs as defined herein) capable of binding to an antigen, and, for example, may be scFv, scFv-Fc, (scFv)$_2$, Fab, Fab', or F(ab')$_2$, but is not limited thereto.

Among the antigen-binding fragments, Fab has a structure composed of variable regions of light and heavy chains, the constant region of a light chain, and the first constant region ($C_{H1}$) of a heavy chain, with one antigen-binding site retained.

Fab' is different from Fab in that Fab' includes a hinge region having at least one cysteine residue at the C-terminal of the heavy chain $C_{H1}$ domain.

F(ab')$_2$ antibody is formed through disulfide bridging of the cysteine residues in the hinge region of Fab'. Fv is a minimal antibody fragment composed of only a heavy chain variable region and a light chain variable region. Recombination techniques of generating an Fv fragment are widely known in the art.

Two-chain Fv includes a heavy chain variable region and a light chain variable region which are linked to each other by a non-covalent bond. Single-chain Fv generally includes a heavy-chain variable region and a light-chain variable region which are linked to each other by a covalent bond via a peptide linker or directly linked at the C-terminals to have a dimer structure like two-chain Fv.

The antigen-binding fragments may be obtained using protease (for example, Fab may be obtained by restrictively cleaving a whole antibody with papain, and an F(ab')$_2$ fragment may be obtained by cleaving with pepsin), or may be prepared by using a genetic recombination technique.

The term "hinge region" refers to a region between $C_{H1}$ and $C_{H2}$ domains within heavy chain of an antibody, which functions to provide flexibility for the antigen-binding site in the antibody.

The antibody provided herein may be a monoclonal antibody. A monoclonal antibody can be prepared using a method widely known in the art, for example, using a phage display technique. Alternatively, the antibody may be constructed in the form of an animal (e.g., mouse)-derived monoclonal antibody by a conventional method.

Meanwhile, individual monoclonal antibodies can be screened using a typical ELISA (Enzyme-Linked ImmunoSorbent Assay) format, based on the binding potential against the receptor binding domain of TIGIT. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to the receptor binding domain of TIGIT may be each verified.

The finally selected antibodies can be prepared and used as humanized antibodies as well as human immunoglobulin antibodies in which the remaining parts except for the antigen-binding portion are humanized. Methods for producing humanized antibodies are well known in the art.

An antigen-binding fragment of the anti-TIGIT antibody provided herein may refer to a fragment which is derived from an anti-TIGIT antibody and retain antigen (TIGIT) binding affinity of the anti-TIGIT antibody. In an embodiment, the antigen-binding fragment may be a polypeptide including the 6 CDRs of an anti-TIGIT antibody as described above, and, for example, may be scFv, scFv-Fc, scFv-Ck (kappa constant region), scFv-CA (lambda constant region), (scFv)$_2$, Fab, Fab', or a F(ab')$_2$, but not be limited thereto. In an embodiment, the antigen-binding fragment may be a fusion polypeptide in which scFv or scFv is fused to the Fc region of an immunoglobulin (e.g., IgG1, IgG2, IgG3, IgG4, etc.) (scFv-Fc) or to a light chain constant region (e.g., kappa or lambda) (scFv-Ck or scFv-CA), but with no limitations thereto.

In this disclosure, an antibody (for example, CDR, variable region, or heavy chain/light chain, antigen-binding fragment etc.) "including (comprising) a specific amino acid sequence or consisting of a specific amino acid sequence" refers to all cases which the amino acid sequence is essentially included, and/or an insignificant mutation (for example, substitution, deletion, and/or addition of amino acid residue(s)) that does not affect antibody activity (for example, antigen binding affinity, pharmacological activity) is introduced into the amino acid sequence.

The anti-TIGIT antibody or antigen-binding fragment thereof provided herein may have a binding affinity (K$_D$) to TIGIT (for example, human TIGIT) of 10 mM or less, 5 mM or less, 1 mM or less, 0.5 mM or less, 0.2 mM or less, 0.1 mM or less, 0.05 mM or less, 0.01 mM or less, 0.005 mM or less, or 0.001 mM or less, for example, 0.0001 nM to 10 mM, 0.0005 nM to 10 mM, 0.001 nM to 10 mM, 0.005 nM to 10 mM, 0.01 nM to 10 mM, 0.05 nM to 10 mM, 0.1 nM to 10 mM, 0.5 nM to 10 mM, 1 nM to 10 mM, 0.0001 nM to 5 mM, 0.0005 nM to 5 mM, 0.001 nM to 5 mM, 0.005 nM to 5 mM, 0.01 nM to 5 mM, 0.05 nM to 5 mM, 0.1 nM to 5 mM, 0.5 nM to 5 mM, 1 nM to 5 mM, 0.0001 nM to 1 mM, 0.0005 nM to 1 mM, 0.001 nM to 1 mM, 0.005 nM to 1 mM, 0.01 nM to 1 mM, 0.05 nM to 1 mM, 0.1 nM to 1 mM, 0.5 nM to 1 mM, 1 nM to 1 mM, 0.0001 nM to 0.5 mM, 5 nM to 0.5 mM, 0.001 nM to 0.5 mM, 0.005 nM to 0.5 mM, 0.01 nM to 0.5 mM, 0.05 nM to 0.5 mM, 0.1 nM to 0.5 mM, 0.5 nM to 0.5 mM, 1 nM to 0.5 mM, 0.0001 nM to 0.2 mM, 5 nM to 0.2 mM, 0.001 nM to 0.2 mM, 0.005 nM to 0.2 mM, 0.01 nM to 0.2 mM, 0.05 nM to 0.2 mM, 0.1 nM to 0.2 mM, 0.5 nM to 0.2 mM, 1 nM to 0.2 mM, 0.0001 nM to 0.1 mM, 5 nM to 0.1 mM, 0.001 nM to 0.1 mM, 0.005 nM to 0.1 mM, 0.01 nM to 0.1 mM, 0.05 nM to 0.1 mM, 0.1 nM to 0.1 mM, 0.5 nM to 0.1 mM, 1 nM to 0.1 mM, 0.0001 nM to 0.05 mM, 5 nM to 0.05 mM, 0.001 nM to 0.05 mM, 0.005 nM to 0.05 mM, 0.01 nM to 0.05 mM, 0.05 nM to 0.05 mM, 0.1 nM to 0.05 mM, 0.5 nM to 0.05 mM, 1 nM to 0.05 mM, 0.0001 nM to 0.01 mM, 5 nM to 0.01 mM, 0.001 nM to 0.01 mM, 0.005 nM to 0.01 mM, 0.01 nM to 0.01 mM, 0.05 nM to 0.01 mM, 0.1 nM to 0.01 mM, 0.5 nM to 0.01 mM, or 1 nM to 0.01 mM, as measured by surface plasmon resonance (SPR), but with no limitations thereto.

Another aspect provides a polypeptide molecule including a heavy chain complementarity determining region (CDR-H1, CDR-H2, CDR-H3, or a combination thereof), a light chain complementarity determining region (CDR-L1, CDR-L2, CDR-L3, or a combination thereof), a combination thereof; or heavy chain variable region, light chain variable region, or a combination thereof in the anti-TIGIT antibody described in the foregoing.

The polypeptide molecule may be used in preparing an antibody as a precursor of antibody, or comprised in a protein scaffold having an antibody-like structure (e.g., peptibody, nanobody), a bispecific antibody, or a multispecific antibody, as a component thereof (e.g., CDR or variable region).

As used herein, the term "peptibody" (peptide+antibody) refers to a fusion protein having similar framework and functions to an antibody, wherein a peptide is fused with the whole or a part of a constant region of an antibody, such as Fc region, and serves as an antigen binding site (heavy chain and/or light chain CDR or variable regions).

The term "nanobody", as used herein, is called a single-domain antibody, refers to an antibody fragment including a single variable domain of an antibody in a monomer form, which exhibits characteristics of selectively binding to a specific antigen similarly to an antibody having an intact structure. The molecular weight of the nanobody is generally about 12 kDa to about 15 kDa, which is very little when compared to the normal molecular weight (about 150 kDa or about 160 kDa) of an intact antibody (including two heavy chains and two light chains) and in some cases it is smaller than an Fab fragment or scFv fragment.

The term "multi-specific antibody" (including bispecific antibody), as used herein, refers to an antibody recognizing and/or binding to two or more different antigens, or recognizing and/or binding to different sites of the same antigen, and one antigen binding site of the multi-specific antibody may include the polypeptide, antibody, or antigen-binding fragment described above to bind to TIGIT.

The polypeptide, antibody, or antigen-binding fragment provided herein, which binds to TIGIT, may be used in the form of a conjugate with at least one selected from among a useful polymer, a label, and the like.

The useful polymer may be, for example, a non-protein polymer that increases the in vivo half-life of a polypeptide, antibody, and/or antigen-binding fragment, and may be at least one hydrophilic polymer selected from the group among polyethylene glycol (PEG) (e.g., 2 kDa, 5 kDa, 10 kDa, 12 kDa, 20 kDa, 30 kDa or 40 kDa PEG), dextran, monomethoxypolyethylene glycol (mPEG), and the like, but with no limitations thereto.

The label may be at least one radionuclide or fluorescent or chemilluminescent small chemical selected from among rare earth chelates, fluorescein and its derivatives, rhodamine and its derivatives, isothiocyanate, phycoerythrin, phycocyanin, allophycocyanin, o-phthaladehyde, fluorescamine, 152Eu, dansyl, umbelliferone, luciferin, a luminal label, an isoluminal label, an aromatic acridinium ester label, an imidazole label, an acridimium salt label, an oxalate ester label, an aequorin label, 2,3-dihydrophthalazinediones, biotin/avidin, spin labels, and stable free radicals, but with no limitations thereto.

Medicinal Use

The anti-TIGIT antibody or antigen-binding fragment thereof provided herein functions to activate immunity (e.g., enhancement of effector T cell function, regulation of Treg activity, increased cytokine secretion, etc.) by blocking the action of TIGIT (e.g. interaction between TIGIT and its ligand, CD155 (PVR)). Thus, the anti-TIGIT antibody or antigen-binding fragment thereof can be applied to immunopotentiation and can find advantageous applications in the prevention and/or treatment of immune-related diseases, particularly cancer.

Another aspect provides an immunopotentiator or an immunopotent pharmaceutical composition, each including the anti-TIGIT antibody or antigen-binding fragment thereof as an active ingredient.

Another aspect provides a pharmaceutical composition including the anti-TIGIT antibody or antigen-binding fragment thereof as an active ingredient for prevention and/ or treatment of an immune-related disease.

Another aspect provides an anticancer agent or a pharmaceutical composition for the prevention and/or treatment of cancer, each including the anti-TIGIT antibody or antigen-binding fragment thereof as an active ingredient.

Another aspect provides an immunopotentiation method including a step of administering a pharmaceutically effective amount of the anti-TIGIT antibody or antigen-binding fragment thereof to a subject in need of immunopotentiation. The immunopotentiation method may further include a step of identifying a subject in need of immunopotentiation before the administering step.

Another aspect provides a method for preventing and/or treating an immune-related disease, the method including a step of administering a pharmaceutically effective amount of the anti-TIGIT antibody or antigen-binding fragment thereof to a subject in need of immune-related disease prevention and/or treatment. The method for preventing and/or treating an immune-related disease may further include a step of identifying a subject in need of immune-related disease prevention and/or treatment before the administering step.

Another aspect provides a method for preventing and/or treating cancer, the method including a step of administering a pharmaceutically effective amount of the anti-TIGIT antibody or antigen-binding fragment thereof to a subject in need of cancer prevention and/or treatment. The method for preventing and/or treating cancer may further include a step of identifying a subject in need of cancer prevention and/or treatment before the administering step.

Another aspect provides a use of the anti-TIGIT antibody or antigen-binding fragment thereof for immunopotentiation or for preparing an immunopotentiator.

Another aspect provides a use of the anti-TIGIT antibody or antigen-binding fragment thereof for preventing and/or treating an immune-related disease or for preparing a drug for the prevention and/or treatment of an immune-related disease.

Another aspect provides a use of the anti-TIGIT antibody or antigen-binding fragment thereof for preventing and/or treating cancer or for preparing a drug for the prevention and/or treatment of cancer.

In the pharmaceutical compositions, methods, and uses provided herein, the anti-TIGIT antibody or antigen-binding fragment thereof may be used in combination of an immune checkpoint protein, for example, a drug (antagonist) targeting either or both of PD-1 and PD-L1. Specifically, the pharmaceutical composition may further include a drug targeting either or both of PD-1 and PD-L1 in addition to the anti-TIGIT antibody or antigen-binding fragment thereof. The method may further include a step of administering a drug targeting either or both of PD-1 and PD-L1 in addition to the anti-TIGIT antibody or antigen-binding fragment.

The drug administrable in combination may be an anti PD-1 antibody, an anti-PD-L1 antibody, or both of them, but is not limited thereto. In an embodiment, the anti-PD-1 antibody may be at least one selected from the group consisting of Pembrolizumab and Nivolumab, but is not limited thereto.

As used herein, the term "immunopotentiation" (or immunoenhancement) means inducing an initial immune response to an antigen or increasing an existing immune response and can be interchangeably used with the terms immunostimulation, immunoaugmentation, immunoactivation, and the like. In an embodiment, immunopotentiation may be performed by at least one selected from among functional enhancement (activation) and/or proliferation of immune cells (effector T cells such as cytotoxic T cells; CD3+ T cells, CD4+ T cells, CD8+ T cells, etc.), inactivation and/or depletion of regulatory T (Treg) cells, increased production and/or secretion of immune proteins (e.g., cytokines, etc.), but with no limitations thereto.

As used herein, the term "immune-related disease" encompasses all diseases caused by impairment and/or insufficient activity of the immune system. Examples of the immune-related disease includes cancer, infectious diseases, autoimmune diseases, inflammatory diseases, and the like, but are not limited thereto.

The cancer may be solid cancer or hematologic cancer, but is not limited thereto, and may be at least one selected from the group consisting of squamous cell carcinoma, lung cancer (e.g., small cell lung cancer, non-small cell lung cancer, adenocarcinoma of the lung, squamous cell carcinoma of the lung, etc.), peritoneal cancer, skin cancer, melanoma (e.g., skin or intraocular melanoma, etc.), rectal cancer, esophageal cancer, small intestine cancer, endocrine cancer, thyroid cancer, parathyroid cancer, adrenal cancer, soft tissue sarcoma, urethral cancer, chronic or acute leukemia, lymphocytic lymphoma, liver cancer, cholangiocarcinoma, gastric cancer, pancreatic cancer, glioblastoma, cervical cancer, ovarian cancer, bladder cancer, breast cancer, colon cancer (e.g., colon cancer, rectal cancer, colorectal cancer, etc.), endometrial or uterine cancer, salivary gland cancer, kidney cancer, prostate cancer, vulvar cancer, head and neck cancer, brain cancer, and osteosarcoma.

The prophylactic and/or therapeutic effects on cancer include all effects of removing (killing) cancer cells, inhibiting the generation and/or growth of cancer cells, and suppressing the aggravation of cancer due to migration, invasion, metastasis, etc.

The infectious diseases, autoimmune diseases, and inflammatory diseases may be selected from all infectious diseases, autoimmune diseases, and inflammatory diseases that can be treated, alleviated, and/or prevented by the immunopotentiation described in the foregoing (e.g., functional potentiation (activation) and/or proliferation of immune cells (effector T cells, such as cytotoxic T cells; CD3+ T cells, CD4+ T cells, CD8+ T cells, etc.), activity inhibition and/or depletion of regulatory T (Treg) cells, increased production and/or secretion of immune proteins (e.g., cytokines (IL-2, IFN-gamma and the like), etc.). For instance, infectious disease is a generic term for diseases that arise when pathogens, such as viruses, bacteria, fungi, and parasites, spread and invade into a living organism (e.g., animals including humans). They may be infections or diseases caused by one or more pathogens selected from group consisting of viruses, bacteria, fungi, parasites, etc. The autoimmune disease may be selected from a group consisting of rheumatoid arthritis, type 1 diabetes, Crohn's disease, ulcerative colitis, Behcet's syndrome, lupus, Sjogren's syndrome, myasthenia gravis, scleroderma, hypothyroidism, hyperthyroidism, psoriasis, vitiligo, multiple sclerosis, autoimmune hepatitis, autoimmune nephritis, autoimmune pancreatitis, autoimmune encephalitis, cytokine storm, etc., but are not limited thereto. The term "inflammatory disease" refers to inflammation (e.g., chronic inflammation or acute inflammation) or a disease caused by inflammation. Examples of the inflammatory disease include heart inflammation (e.g., coronary artery disease, angina, myocardial infarction, pericarditis, myocarditis, etc.), vascular inflammation (e.g., atherosclerosis, vasculitis, disseminated intravascular coagulation (DIC), immune thrombocytopenia purpura (ITP), thrombotic thrombocytopenia purpura (TTP), anemia, etc.), upper respiratory tract inflammation (e.g. acute nasopharyngitis, allergic rhinitis, sinusitis, pharyngitis, tonsillitis, laryngitis, etc.), lower respiratory tract and/or lung inflammation (e.g. bronchitis, bronchiectasis, asthma, chronic pulmonary active pulmonary disease (COPD), pneumonia, interstitial lung disease, tuberculosis, etc.), upper gastrointestinal tract inflammation (e.g. gastritis, esophagitis, etc.), lower gastrointestinal tract (e.g., enteritis, ulcerative colitis, Crohn's disease, celiac disease, diverticulitis, irritable bowel syndrome, appendicitis, perianal fistula, etc.), inflammation of the liver, biliary tract and/or pancreas (e.g., hepatitis, fatty liver, cholangitis, cholecystitis, pancreatitis, type 1 diabetes, etc.), kidney (upper urinary tract) inflammation (e.g., pyelonephritis, glomerulonephritis, urinary tract infections, etc.), lower urinary tract inflammation (e.g., urinary tract infections, ureteritis, urethritis, cystitis, prostatitis/chronic pelvic pain syndrome, etc.), thyroid and/or parathyroid inflammation (e.g., thyroiditis, parathyroiditis, etc.), adrenal inflammation (e.g., adrenalitis, etc.), genital inflammation (e.g., pelvic inflammatory diseases, oophoritis, orchitis, epididymitis, etc.), bone and/or joint inflammation (e.g., osteoarthritis, rheumatoid arthritis, osteomyelitis, synovitis, etc.), skin inflammation (e.g., skin: cellulitis, erysipelas, tinea versicolor, athlete's foot, acne etc.), muscle inflammation (e.g., myositis, etc.), brain inflammation (e.g., encephalitis, major depressive disorder, etc.), nerve inflammation (e.g., neuritis in various parts such as eyes, ears, etc., complex regional pain syndrome, Guillain-Barre syndrome, etc.), eye inflammation (e.g., stye, uveitis, conjunctivitis, etc.), ear inflammation (e.g., otitis media, mastoiditis, etc.), oral inflammation (e.g., stomatitis, periodontitis, gingivitis, etc.), systemic inflammation (e.g., systemic inflammatory response syndrome (sepsis), metabolic syndrome-related diseases, etc.), peritonitis, reperfusion injury, transplant rejection response, and hypersensitivity, but are not limited thereto.

The anti-TIGIT antibody, antigen-binding fragment thereof, and/or pharmaceutical composition including same provided herein may be administered to any animal or cell, for example, animals selected from mammals including primates such as humans and monkeys, rodents such as rats, mice, and the like., or cells, tissues, body fluids (e.g., sera) derived (isolated) from the animals, or cultures thereof, e.g., cells, tissues, body fluid (sera) isolated from humans.

The pharmaceutical composition may include a pharmaceutically acceptable carrier in addition to the anti-TIGIT antibody or antigen-binding fragment thereof as an active ingredient. The pharmaceutically acceptable carrier is commonly used in the formulation of protein drugs, and may be at least one selected from the group consisting of lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, but with no limitations thereto. The pharmaceutical composition may further include at least one selected from the group consisting of diluents, excipients, lubricants, wetting agents, sweeteners, flavoring agents, emulsifiers, suspending agents, preservatives, and the like, which are commonly used in the preparation of pharmaceutical compositions.

The anti-TIGIT antibody, antigen-binding fragment thereof and/or pharmaceutical composition can be administered via an oral or parenteral route. For parenteral administration, intravenous injection, subcutaneous injection, intramuscular injection, intraperitoneal injection, intradermal administration, topical administration, intranasal administration, intrapulmonary administration, intrarectal administration, etc. may be taken. Since proteins or peptides are digested when administered orally, the active ingredient in the compositions for oral administration may be coated or formulated to prevent digestion in stomach.

In addition, the anti-TIGIT antibody, antigen-binding fragment thereof, and/or pharmaceutical composition may be in the form of a solution, suspension, syrup or emulsion in an oil or aqueous medium, or may be formulated into extracts, pulvis, powders, granules, tablets or capsules, injections, etc. The composition may additionally include a dispersing agent or a stabilizer for formulation.

The content of the anti-TIGIT antibody or antigen-binding fragment thereof or the dosage thereof in the pharmaceutical composition may be determined, depending on various factors, such as the formulation method, administration method, patient's age, weight, sex, pathology, meals, and administration time, administration interval, administration route, excretion rate, response sensitivity, etc. The pharmaceutical composition may be administered at a daily dose, based on the active ingredient (the anti-TIGIT antibody or antigen-binding fragment), of 0.00001 to 1000 mg/kg, 0.00001 to 500 mg/kg, 0.00001 to 100 mg/kg, 0.00001 to 50 mg/kg, 0.0001 to 1000 mg/kg, 0.0001 to 500 mg/kg, 0.0001 to 100 mg/kg, 0.0001 to 50 mg/kg, 0.001 to 1000 mg/kg, 0.001 to 500 mg/kg, 0.001 to 100 mg/kg, 0.001 to 50 mg/kg, 0.01 to 1000 mg/kg, 0.01 to 500 mg/kg, 0.01 to 100 mg/kg, 0.01 to 50 mg/kg, 0.1 to 1000 mg/kg, 0.1 to 500 mg/kg, 0.1 to 100 mg/kg, or 0.1 to 50 mg/kg, but with no limitations thereto. The daily dose may be formulated as one formulation in unit dose form, formulated in appropriate portions, or prepared by placing it in a multi-dose container. In addition, in the present specification, a pharmaceutically effective amount refers to an amount of an active ingredient that can exhibit a desired pharmacological activity of an active ingredient, and may be within the above-described dosage range.

Construction of Polynucleotide and Expression Vector and Production of Antibody

Another aspect provides a nucleic acid molecule encoding the heavy chain complementarity determining region, heavy chain variable region, or heavy chain of the anti-TIGIT antibody.

Another aspect provides a nucleic acid encoding the light chain complementarity determining region, light chain variable region, or light chain of the anti-TIGIT antibody.

Another aspect provides a recombinant vector provides a recombinant vector carrying a nucleic acid molecule coding for the heavy chain complementarity determining region, heavy chain variable region, or heavy chain of the anti-TIGIT antibody and a nucleic acid molecule coding for the light chain complementarity determining region, light chain variable region, or light chain of the anti-TIGIT antibody in combination, or separate recombinant vectors carrying a nucleic acid molecule coding for the heavy chain complementarity determining region, heavy chain variable region, or heavy chain of the anti-TIGIT antibody and a nucleic acid molecule coding for the light chain complementarity determining region, light chain variable region, or light chain of the anti-TIGIT antibody, respectively. The recombinant vectors may be expression vectors for expressing the nucleic acid molecules.

Another aspect provides a recombinant cell anchoring the recombinant vector thereat.

As used herein, the term "vector" refers to a means for expressing a target gene in a host cell, as exemplified by a plasmid vector, a cosmid vector, and a viral vector such as a bacteriophage vector, a lentivirus vector, an adenovirus vector, a retrovirus vector, and an adeno-associated virus vector. The recombinant vector may be constructed by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), a phage (for example, λgt4λB, λ-Charon, λΔz1, M13, etc.), or a virus vector (for example, SV40, etc.), which is commonly used in the art.

In the recombinant vector, the nucleic acid molecule may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of a polynucleotide of interest.

The recombinant vector may be constructed typically as a cloning vector or an expression vector. For recombinant expression vectors, a vector generally available in the relevant art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pL^λ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, tk promoter of HSV, etc.), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure may be selected from *E. coli* such as *E. coli* JM109, *E. coli* BL21, *E. coli* RR1, *E. coli* LE392, *E. coli* B. *E. coli* X 1776, *E. coli* W3110, *Bacillus* spp. such as *Bacillus subtilis* and

*Bacillus thuringiensis*, and enterobacteriaceae strains such as *Salmonella typhimurium, Serratia marcescens* and various *Pseudomonas* species. Eukaryotic host cells that may be used for transformation may selected from, but are not limited to, *Saccharomyces cerevisiae*, insect cells, plant cells and animal cells, such as Sp2/0, CHO (Chinese hamster ovary) K1, CHO DG44, CHO S, CHO DXB11, CHO GS-KO, PER.C6, W138, BHK, COS-7, 293, HepG2, Huh7, 3T3, RIN, MDCK, etc.

The nucleic acid molecule or a recombinant vector carrying same may be delivered (introduced) into a host cell using a method well known in the relevant art. For example, this delivery may be carried out using a $CaCl_2$ or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another aspect provides a method for producing the anti-TIGIT antibody or antigen-binding fragment thereof, the method including a step of expressing the nucleic acid molecules in a host cell. The step of expressing the nucleic acid molecule in a host cell may be a step in which a cell anchoring the nucleic acid molecules or a recombinant vector carrying same is cultured. The method may further include a step of separating and/or purifying an antibody or antigen-binding fragment from the medium after the culture step.

Advantageous Effects

The anti-TIGIT antibody or antigen-binding fragment thereof provided herein has the function of blocking the action of TIGIT to activate immunity (e.g., enhancing effector T cell functions, regulating Treg activity, increasing cytokine secretion, etc.) and thus can find advantageous applications as various immune activators and/or immune therapeutics.

DESCRIPTION OF DRAWINGS

FIG. 1 is a graph showing flow cytometry results of the anti-TIGIT antibody (7A6) according to an embodiment.

FIG. 2 shows sequence alignments of the chimeric and humanized antibodies according to an embodiment.

FIG. 3*a* shows epitope mapping results of the anti-TIGIT antibody according to an embodiment and FIG. 3*b* shows the epitope location on the tertiary structure of the TIGIT protein.

FIG. 4 is a graph showing the binding affinity of the anti-TIGIT antibody according to an embodiment for TIGIT in human primary T cells.

FIG. 5 is a graph showing the TIGIT-PVR blocking effect of the anti-TIGIT antibody according to an embodiment.

FIG. 6 is a graph showing the effect of the anti-TIGIT antibody according to an embodiment on cytokine (IL-2 and IFN-gamma) production/secretion in human peripheral blood mononuclear cells (PBMCs).

FIGS. 7*a* and 7*b* are graphs showing the cytokine production/secretion effect of the anti-TIGIT antibody according to an embodiment in T cells, as analyzed for CD4+ T cells (7a) and for CD8+ T cells (7b).

FIGS. 8a to 8d are graphs showing the cytokine production/secretion effect of the anti-TIGIT antibody according to an embodiment in T cells, as analyzed for the IL-2 concentration in CD4+ T cells (8a), the IFN-gamma concentration in CD4+ T cells (8b), the IL-2 concentration in CD8+ T cells (8c), and the IFN-gamma concentration in CD8+ T cells (8d).

FIGS. 9a to 9d are graphs showing the cytokine production/secretion effect of the anti-TIGIT antibody according to an embodiment in T cells depending on its concentration, as analyzed for the IL-2 concentration in CD4+ T cells (9a), the IFN-gamma concentration in CD4+ T cells (9b), the IL-2 concentration in CD8+ T cells (9c), and the IFN-gamma concentration in CD8+ T cells (9d).

FIGS. 10a and 10b are graphs showing the effect of the anti-TIGIT antibody according to an embodiment on T cell proliferation in human PBMCs, as analyzed by the CFSE assay (10a) and by the Ki67 assay (10b).

FIG. 11 is a graph showing the effect of the anti-TIGIT antibody according to an embodiment on T cell proliferation in the presence of Treg cells.

FIG. 12 is a graph showing the complex blocking effect of a combination of the anti-TIGIT antibody and anti-PD1 antibody according to an embodiment on TIGIT-PVR/PD-1-PD-L1, as analyzed by a cell-based NFAT reporter response bioassay.

FIGS. 13a and 13b are graphs showing comparison of blocking effects against TIGIT-PVR/PD-1-PD-L1 between the anti-TIGIT antibody according to an embodiment and the reference antibodies upon use in combination with the anti-PD1 antibodies pembrolizumab (13a) and nivolumab (13b).

FIGS. 14a and 14b are graphs showing the cytokine production results of human T cells when the anti-TIGIT antibody according to an embodiment is used alone or in combination with the anti-PD1 antibody, as analyzed for CD4+ cells (14a) and for CD8+ cells (14b).

FIG. 15 is a graph showing the expression levels of the TIGIT ligand CD155 in A375 and SK-OV3 tumor cell lines.

FIG. 16 is a graph showing the cytotoxicity (cell death rate) of the anti-TIGIT antibody according to an embodiment against the A375 tumor (melanoma) cell line.

FIGS. 17a and 17b are graphs showing the cytotoxicity (cell death rate) of the anti-TIGIT antibody according to an embodiment against the SKOV-3 tumor (ovarian cancer) cell line.

FIG. 18 is a graph showing the cytotoxicity (cell death rate) of the anti-TIGIT antibody according to an embodiment against the SKOV-3 tumor (ovarian cancer) cell line.

FIG. 19 is a plot showing the cytotoxicity (cell death rate) of the anti-TIGIT antibody according to an embodiment against the SKOV-3 tumor (ovarian cancer) cell line when co-cultured with NK cells.

FIG. 20 is a graph showing the in vivo antitumor effect of the anti-TIGIT antibody according to an embodiment against colon cancer.

FIG. 21 is a plot showing in vivo antitumor effects on colon cancer when the anti-TIGIT antibody according to an embodiment was used alone and in combination with the anti-PD1 antibody.

FIG. 22 shows the results of assaying the effects on immune cells in the tumor microenvironment (TME) when the anti-TIGIT antibody according to an embodiment was used in combination with anti-PD1 antibody.

FIG. 23 is a plot showing in vivo antitumor effects of the anti-TIGIT antibody according to an embodiment on a heterograft tumor derived from liver cancer patients.

FIG. 24 is a graph showing the expression levels of TIGIT on T cell subsets in the tumor microenvironment (TME).

FIG. 25 presents graphs of the effects of the anti-TIGIT antibody according to an embodiment on cytokine production in T cells derived from liver cancer patients.

FIG. 26 presents graphs of the effects of the anti-TIGIT antibody according to an embodiment on cytokine production in T cells derived from lung cancer patients.

FIG. 27 presents graphs of the effects of the anti-TIGIT antibody according to an embodiment on cytokine production in T cells derived from colon cancer patients.

FIGS. 28a and 28b are graphs showing the activation (cytokine production) effects in central memory T cells (28a) and effector memory T cells (28b) by the anti-TIGIT-Fab fragment according to an embodiment.

FIG. 29 presents graphs of the cytotoxicity (cell death rate) of the anti-TIGIT-Fab fragment according to an embodiment against A375 tumor cells.

FIG. 30 presents graphs indicating the expression levels of TIGIT in T cell subsets.

FIGS. 31a to 31d are graphs showing the residual cell counts of Tregs, CD4+ T cells, and CD8+ T cells following treatment with the anti-TIGIT antibody according to an embodiment.

FIG. 32 presents graphs of the cell counts of Tregs and NK cells following treatment with the anti-TIGIT antibody according to an embodiment.

FIG. 33 displays a graph showing the residual cell counts of Treg cells following treatment with the anti-TIGIT antibody according to an embodiment in the presence of NK.

FIGS. 34a and 34b are graphs illustrating the cytokine production effects in T cells, depending on whether or not the anti-TIGIT antibody according to an embodiment blocks FcgRIIIA (34a: CD4+ T cells, 34b: CD8+ T cells).

MODE FOR INVENTION

A better understanding of the present disclosure may be obtained via the following Examples, which are set forth to illustrate, but are not to be construed to limit, the present disclosure. It is obvious to those skilled in the art the following Examples could be modified without departing the gist of the present invention.

Example 1: Construction of Anti-TIGIT Antibody 1.1. Production of Anti-TIGIT Monoclonal Antibody Five BALB/c mice were immunized by cross-injecting the MMB-designed immunogen (Ag1585_IMM) and human TIGIT protein (aa22-138; Sino Biologics, UniProtKB/SwissProt Q495A1-1) by sequential cross-injection five times during 19 days. Lymphocytes were collected from the five mice, pooled, purified, and then fused with SP2/0 myeloma cells. The fused cells were propagated in HAT selective single-step cloning media, and the resultant 1,896 hybridoma clones were transferred and cultured in 96-well plates.

The peptide Ag1585_IMM used as the immunogen was modeled to reflect the folding and proximity-based relationships within the parent protein, and it is expected to be useful in generating antibodies with full activity against corresponding epitopes within the entire protein, by maximizing the potential of the immunogenic protein. The peptide Ag1585_IMM was synthesized to include 20 amino acids from the 51$^{st}$ amino acid residue (T) to the 70$^{th}$ amino acid residue (N) of human TIGIT. The information about the peptide Ag1585_IMM is summarized in Table 3 below:

TABLE 3

| Peptide ID | Location in Consensus sequence | Sequence | Secondary Structure | RMSD score (Å) |
|---|---|---|---|---|
| Ag1585_ IMM | 51-70 | TAQVTQVN WEQQDQLL AICN (SEQ ID NO: 31) | β-sheet, turn | 0.006 |

Table 3 above illustrates the structural features of the modeled Ag1585_IMM and its alignment with the TIGIT structure (PDB: 5V52). A low RMSD score indicates a good alignment. The peptide was synthesized based on the corresponding immunogen sequence.

Using indirect ELISA, the supernatants of hybridoma tissue culture were screened for their effects on the immunizing antigen Ag1585_IMM and recombinant human TIGIT (His) (Sino biologics). For the effective clones (positive clones), further indirect ELISA tests were conducted on the screening antigen (recombinant human TIGIT Fc chimera protein (R&D systems, 9464-TG)) and cells to confirm Ig secretion and specificity. The CHO-K1 (ATCC, CCL-61) cell line was used as a negative control.

ELISA was performed under the following conditions:

ELISA plates were coated with 100 μL/well of Carbonate Coating Buffer (pH 9.6) O/N containing recombinant human TIGIT (mTIGIT) protein at a concentration of 0.1 μg/well at 4° C.

Plates were blocked with 3% skim milk powder in PBS for 1 hour at room temperature.

Secondary antibody goat anti-mouse IgG/M (H+L)-HRP in PBS-Tween (1:10000) was incubated for 1 hour at 37° C. with shaking (100 μL/well).

All wash steps were performed with PBS-Tween for 3 minutes.

TMB substrate was added at a concentration of 50 μL/well and incubated in the dark for 5-10 minutes before stopping the reaction with an equal volume of 1M HCl.

By isotyping, clones expressing IgM were identified and removed, and clones expressing IgG were collected.

The collected positive clones were subcloned to identify stable expression clones. The culture supernatants containing the selected clones were passed through a Protein A column for elution and the buffer was exchanged to PBS. The purified antibodies were tested by indirect ELISA against the screening antigen (Recombinant Human TIGIT (T103) Fc Chimera Protein; R&D systems) and a negative control antigen (His peptide).

The binding of the selected lead antibody clone (7A6) was measured by flow cytometry analysis. CHO-K1 (ATCC, CCL-61) and human TIGIT-expressing CHO-K1 (CHO-K1 TIGIT) (Genscript, M00542) cells were trypsinized, counted, resuspended at a concentration of 2×10$^6$ cells/ml, and cultured with Fc block (BD Bioscience 564220) for 30 minutes. After cultivation, the cells were added to 96-well plates, and the added antibody (single point) was serially diluted (eight points, starting from 5 μg/mL and diluted 3-fold). For CHO-K1 cells (negative control), they were tested at a single concentration of 5 μg/mL, equivalent to the highest concentration in the titration performed on CHO-K1 TIGIT cells. After 30 minutes of cultivation, antibody binding was measured using the anti-mouse IgG (H+L) Alexa Fluor 647 antibody (Sigma A21236) at 4 μg/mL (protected from light). Flow cytometry was conducted using the AccuriC6 Flow Cytometer, and the data was analyzed with FlowJo. The obtained results are depicted in FIG. 1.

The hybridoma cell pellet corresponding to the stable expression clone was lysed, mRNA was extracted, and the variable region DNA of the heavy and light chains was cloned into a sequencing vector. The DNA sequences of the heavy and light chains were analyzed. The sequence analysis results of the mouse anti-TIGIT clone (7A6) are listed in Table 4 below.

TABLE 4

| Variable region | Amino acid sequence (N→C) or nucleotide sequence (5'→3') | SEQ ID NO: |
|---|---|---|
| Heavy chain variable region | DVQLQESGPGLVKPSQSLSLTCTVTGYSITSDYAWNWIRQFPG NKLEWMGYISYSGSARYNPSLKSRISITRDTSMNQFFLQLNSV TAEDTATYYCARKGYPAYFAYWGQGTLVTVSS | 9 |
| | GATGTGCAGC TTCAGGAGTC GGGACCTGGC CTGGTGAAAC CTTCTCAGTC TCTGTCCCTC ACCTGCACTG TCACTGGCTA CTCAATCACC AGTGATTATG CCTGGAACTG GATCCGGCAG TTTCCAGGAA ACAAACTGGA GTGGATGGGC TACATAAGCT ACAGTGGTAG CGCTCGCTAC AACCCATCTC TCAAAAGTCG AATCTCTATC ACTCGAGACA CATCCATGAA CCAGTTCTTC CTGCAGTTGA ATTCTGTGAC TGCTGAGGAC ACAGCCACAT ATTACTGTGC AAGAAAGGGG TACCCTGCCT ACTTTGCTTA CTGGGGCCAA GGGACTCTGG TCACTGTCTC TGCA | 23 |
| Light chain variable region | DIVMTQSHKFMSTSVGDRVSISCKASQDVSTAVAWYQQKPG QSPELLIYSASYRYTGVPDRFTGSGSGTDFTFTISSVQAED LAVYYCQHHYSTPYTFGGGTKLEMK | 15 |
| | GACATTGTGA TGACCCAGTC TCACAAATTC ATGTCCACAT CAGTAGGAGA CAGGGTCAGC ATCTCCTGCA AGGCCAGTCA GGATGTGAGT ACTGCTGTAG CCTGGTATCA ACAGAAACCA GGACAATCTC CTGAACTACT GATTTACTCG GCATCCTACC GGTACACTGG AGTCCCTGAT CGCTTCACTG GCAGTGGATC TGGGACGGAT TTCACTTTCA CCATCAGCAG | 24 |

TABLE 4-continued

| Variable region | Amino acid sequence (N→C) or nucleotide sequence (5'→3') | SEQ ID NO: |
|---|---|---|
| | TGTGCAGGCT GAAGACCTGG CAGTTTATTA CTGTCAGCAT CATTATAGTA CTCCGTACAC GTTCGGAGGG GGGACCAAGC TGGAAATGAA A | |

(In Table 4, the underlined regions represent CDR1, CDR2, and CDR3 of the heavy chain and light chain, in that order)

1.2. Humanization of Mouse Anti-TIGIT Clone

To confirm the amino acid residues critical for antibody structure and binding, the protein structure model of the monoclonal antibody variable regions (mAb V regions) was analyzed. This information was utilized in conjunction with in silico design of human antibody structures. Extensive preliminary sequence fragments potentially usable for humanizing the 7A6 were screened and their peptide binding to human MHC class II alleles was examined. Where possible, sequence fragments identified as significant non-human germline binders to human MHC class II were discarded. This reduced the fragment set, and these combinations were re-analyzed using the above method to ensure that the junctions between fragments did not include potential T cell epitopes. To generate a complete variable region (V region) containing without or reduced significant T cell epitopes, sequence fragments were assembled to design a human variable region that evades potential T cell epitope recognition or contains minimized T cell epitopes (deimmunization).

For gene synthesis and expression in mammalian cells, five heavy chain (VH1 to VH5) and five light chain (Vκ1 to Vκ5) sequences were selected.

The summary of stable IgG antibodies produced by transient transfection, which includes one chimera (VH0/Vκ0) and 25 humanized variants (marked with 'o'), is presented in Table 5, below:

TABLE 5

| | % | | 75.5 VH0 | 83.7 VH1 | 85.7 VH2 | 86.9 VH3 | 88.9 VH4 | 89.9 VH5 |
|---|---|---|---|---|---|---|---|---|
| | | | | | Heavy Chain | | | |
| Light chain | 66.3 | Vκ0 | o | | | | | |
| | 73.7 | Vκ1 | | o | o | o | o | o |
| | 75.8 | Vκ2 | | o | o | o | o | o |
| | 77.9 | Vκ3 | | o | o | o | o | o |
| | 80.0 | Vκ4 | | o | o | o | o | o |
| | 81.1 | Vκ5 | | o | o | o | o | o |

(In Table 5, the given values (%) indicate percentage humanness (determined as percent homology to the closest matching human germline)).

The chimeric antibody (VH0XVκ0) and humanized antibody sequences derived by applying the combination of the 7A6 clone in Table 4 to the combination in Table 5 are presented in Tables 6 and 7 and FIG. 2. In Tables 6 and 7 and FIG. 2, amino acid sequence numbering and CDR regions were determined according to Kabat definitions, and amino acid residues that changed from the CDR and parent sequence (VH0 or Vκ0) determined above were shaded in FIG. 2.

TABLE 6

Heavy Chain (constant region: human IgG1)

| | Amino acid sequence (N→C) | SEQ ID NO: |
|---|---|---|
| 7A6_VH0 variable region | DVQLQESGPGLVKPSQSLSLTCTVTGYSITSDYAWNWIRQFPG NKLEWMGYISYSGSARYNPSLKSRISITRDTSMNQFFLQLNSV TAEDTATYYCARKGYPAYFAYWGQGTLVTVSS | 9 |
| 7A6_VH1 variable region | DVQLQESGPGLVKPSQTLSLTCTVTGYSITSDYAWNWIRQPPGK GLEWMGYISYSGSARYNPSLKSRITISRDTSMNQFSLKLNSVTA EDTATYYCARKGYPAYFAYWGQGTLVTVSS | 10 |
| 7A6_VH2 variable region | DVQLQESGPGLVKPSQTLSLTCTVTGYSITSDYAWNWIRQPPGK GLEWMGYISYSGSARYNPSLKSRITISRDTSKNQFSLKLSSVTA EDTATYYCARKGYPAYFAYWGQGTLVTVSS | 11 |
| 7A6_VH3 variable region | QVQLQESGPGLVKPSQTLSLTCTVTGYSITSDYAWNWIRQPPG KGLEWMGYISYSGSARYNPSLKSRVTISRDTSKNQFSLKLSSV TAEDTATYYCARKGYPAYFAYWGQGTLVTVSS | 12 |
| 7A6_VH4 variable region | QVQLQESGPGLVKPSQTLSLTCTVTGYSITSDYAWNWIRQPPG KGLEWMGYISYSGSARYNPSLKSRVTISRDTSKNQFSLKLSSV TAADTAVYYCARKGYPAYFAYWGQGTLVTVSS | 13 |
| 7A6_VH5 variable region | QVQLQESGPGLVKPSQTLSLTCTVTGYSITSDYAWNWIRQPPG KGLEWMGYISYSGSARYNPSLKSRVTISVDTSKNQFSLKLSSV TAADTAVYYCARKGYPAYFAYWGQGTLVTVSS | 14 |
| Constant region (common) | ASTKGPSVFPLAPSSKSTSGGTAALGCLVKDYFPEPVTVSWNS GALTSGVHTFPAVLQSSGLYSLSSWTVPSSSLGTQTYICNVNH KPSNTKVDKRVEPKSCDKTHTCPPCPAPELLGGPSVFLFPPKP KDTLMISRTPEVTCVVVDVSHEDPEVKFNWYVDGVEVHNAKTK | 21 |

TABLE 6-continued

| Heavy Chain (constant region: human IgG1) | |
| --- | --- |
| Amino acid sequence (N→C) | SEQ ID NO: |
| PREEQYNSTYRWSVLTVLHQDWLNGKEYKCKVSNKALPAPIEK TISKAKGQPREPQVYTLPPSREEMTKNQVSLTCLVKGFYPSDI AVEWESNGQPENNYKTTPPVLDSDGSFFLYSKLTVDKSRWQQG NVFSCSVMHEALHNHYTQKSLSLSPGK | |

TABLE 7

| Light Chain (constant region: kappa (expressed as K, k, or κ)) | | |
| --- | --- | --- |
| | Amino acid sequence (N→C) | SEQ ID NO: |
| 7A6_VK0 variable region | DIVMTQSHKFMSTSVGDRVSISCKASQDVSTAVAWYQQKPGQSP ELLIYSASYRYTGVPDRFTGSGSGTDFTFTISSVQAEDLAVYYC QHHYSTPYTFGGGTKLEMK | 15 |
| 7A6_VK1 variable region | DIVMTQSHSFLSASVGDRVSITCKASQDVSTAVAWYQQKPGQAP ELLIYSASYRYTGVPDRFTGSGSGTDFTLTISSLQAEDVAVYYC QHHYSTPYTFGQGTKLEMK | 16 |
| 7A6_VK2 variable region | DIVMTQSPSSLSASVGDRVSITCKASQDVSTAVAWYQQKPGQAP RLLIYSASYRYTGVPDRFTGSGSGTDFTLTISSLQAEDVAVYYC QHHYSTPYTFGQGTKLEIK | 17 |
| 7A6_VK3 variable region | DIQMTQSPSSLSASVGDRVSITCKASQDVSTAVAWYQQKPGQAP RLLIYSASYRYTGVPDRFSGSGSGTDFTLTISSLQAEDVAVYYC QHHYSTPYTFGQGTKLEIK | 18 |
| 7A6_VK4 variable region | DIQMTQSPSSLSASVGDRVTITCRASQDVSTAVAWYQQKPGQAP RLLIYSASYRYTGVPDRFSGSGSGTDFTLTISSLQAEDVAVYYC QHHYSTPYTFGQGTKLEIK | 19 |
| 7A6_VK5 variable region | DIQMTQSPSSLSASVGDRVSITCKASQDVSTAVAWYQQKPGQAP RLLIYSASYRYTGVPDRFSGSGSGTDFTLTISSLQPEDFATYYC QHHYSTPYTFGQGTKLEIK | 20 |
| Constant region (common) | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC | 22 |

Of the antibodies produced, the 7A6 VH3/Vk5 hIgG1 antibody was let to undergo the following point mutations on the Fc region of the heavy chain thereof to produce Fc-engineered variants:

(1) S240D, A331L, and I333E (DLE variant): 7A6 VH3/Vk5-DLE;

(2) N298A: 7A6 VH3/Vk5 N298A;

(3) S299A, E3334A, and K335A (AAA variant): 7A6 VH3/k5 AAA; or (4) L235A, L236A, and P330G (LALAPG variant): 7A6 VH3/Vk5 LALAPG The sequences of the heavy and light chains of antibodies containing the above Fc-engineered variants are listed in Table 8.

TABLE 8

| | Amino acid sequence (N→C) | SEQ ID NO: |
| --- | --- | --- |
| 7A6 VH3/Vk5- DLE heavy chain | QVQLQESGPGLVKPSQTLSLTCTVTGYSITSDYAWNWIRQ PPGKGLEWMGYISYSGSARYNPSLKSRVTISRDTSKNQFS LKLSSVTAEDTATYYCARKGYPAYFAYWGQGTLVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKRVEPKSCDKTHTCPPCPAPELLGGPD VFLFPPKPKDTLMISRTPEVTCWVDVSHEDPEVKFNWYV DGVEVHNAKTKPREEQYNSTYRVVSVLTVLHQDWLNGKE YKCKVSNKALPLPEEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHYT QKSLSLSPG | 25 |
| VH3/Vk5 N298A heavy chain | QVQLQESGPGLVKPSQTLSLTCTVTGYSITSDYAWNWIRQ PPGKGLEWMGYISYSGSARYNPSLKSRVTISRDTSKNQFS LKLSSVTAEDTATYYCARKGYPAYFAYWGQGTLVTVSSAS | 26 |

TABLE 8-continued

| | Amino acid sequence (N→C) | SEQ ID NO: |
|---|---|---|
| | TKGPSVFPLAPSSKSTSGGTAALGCLVKDYFPEPVTVSWN SGALTSGVHTFPAVLQSSGLYSLSSWTVPSSSLGTQTYIC NVNHKPSNTKVDKRVEPKSCDKTHTCPPCPAPELLGGPSV FLFPPKPKDTLMISRTPEVTCVVVDVSHEDPEVKFNWYVD GVEVHNAKTKPREEQYASTYRWSVLTVLHQDWLNGKEYK CKVSNKALPAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQK SLSLSPGK | |
| 7A6 VH3/Vk5 AAA heavy chain | <u>QVQLQESGPGLVKPSQTLSLTCTVTGYSITSDYAWNWIRQ PPGKGLEWMGYISYSGSARYNPSLKSRVTISRDTSKNQFS LKLSSVTAEDTATYYCARKGYPAYFAYWGQGTLVTVSSAS</u> TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKRVEPKSCDKTHTCPPCPAPELLGGPS VFLFPPKPKDTLMISRTPEVTCVVDVSHEDPEVKFNWYVD GVEVHNAKTKPREEQYNATYRVVSVLTVLHQDWLNGKEYK CKVSNKALPAPIAATISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQK SLSLSPGK | 27 |
| 7A6 VH3/Vk5 LALAPG heavy chain | <u>QVQLQESGPGLVKPSQTLSLTCTVTGYSITSDYAWNWIRQ PPGKGLEWMGYISYSGSARYNPSLKSRVTISRDTSKNQFS LKLSSVTAEDTATYYCARKGYPAYFAYWGQGTLVTVSSAS</u> TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKRVEPKSCDKTHTCPPCPAPEAAGGPS VFLFPPKPKDTLMISRTPEVTCWVDVSHEDPEVKFNWYVD GVEVHNAKTKPREEQYNSTYRVVSVLTVLHQDWLNGKEYK CKVSNKALGAPIEKTISKAKGQPREPQVYTLPPSREEMTK NQVSLTCLVKGFYPSDIAVEWESNGQPENNYKTTPPVLDS DGSFFLYSKLTVDKSRWQQGNVFSCSVMHEALHNHYTQ KSLSLSPGK | 28 |
| 7A6 VH3/Vk5 mutant light chain (common) | <u>DIQMTQSPSSLSASVGDRVSITCKASQDVSTAVAWYQQKP GQAPRLLIYSASYRYTGVPDRFSGSGSGTDFTLTISSLQP EDFATYYCQHHYSTPYTFGQGTKLEIKRTVAAPSVFIFPP</u> SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 29 |

(In Table 8, variable regions are underlined and mutated amino acid residues in Fc regions are bolded)

1.3. Transient Expression of Chimeric and Humanized IgG1 Antibodies

The coding DNA for the VH0/Vκ0 chimeric antibody and the coding DNAs for combinations of humanized heavy chain and light chain (a total of 25 humanized pairings) were transiently transfected into HEK293 EBNA adherent cells (LGC Standards, Teddington, UK) in 6-well plates using the PEI transfection method. After transfection, the cells were cultured for 7 days. Samples were collected, and antibody concentrations were measured on the Octet QK384 using Protein A biosensors (Molecular Devices, Wokingham, Berkshire, UK), based on human IgG1 antibody standards.

The results obtained are presented in Table 9, below:

TABLE 9

| | | Heavy Chain | | | | | |
|---|---|---|---|---|---|---|---|
| | | VH0 | VH1 | VH2 | VH3 | VH4 | VH5 |
| Light chain | Vκ0 | 16.6 | | | | | |
| | Vκ1 | | 15.4 | 21.3 | 20.8 | 23.5 | 7.1 |
| | Vκ2 | | 18.2 | 26.1 | 29.2 | 32.2 | 17.9 |
| | Vκ3 | | 20.7 | 27.4 | 27.1 | 28.9 | 16.0 |
| | Vκ4 | | 28.4 | 34.3 | 35.6 | 33.3 | 17.6 |
| | Vκ5 | | 18.8 | 22.8 | 25.0 | 25.9 | 9.9 |

Table 9 shows the IgG concentrations (µg/mL) in the supernatants after the expression of the chimeric antibody (VH0/Vκ0) and various combinations of humanized antibodies in HEK cells.

As shown in Table 9, all the tested antibodies were well-expressed, and in particular, all humanized variants, except for VH5Vκ1 and VH5Vκ5, were better expressed than the VH0/Vk0 chimeric antibody.

1.4. Single Cycle Kinetic Analysis of Chimeric and Humanized Variants

To evaluate the binding of all variants to the human TIGIT antigen and select humanized IgG antibodies with an affinity closest to the chimeric antibody (VH0Vκ0), a single cycle kinetic analysis (cartoon) was performed in the supernatant from the transfected cell culture. The kinetic test was conducted at 25° C. using the Biacore T200 running Biacore T200 Control software V2.0.1 and Evaluation software V3.0 (GE Healthcare, Uppsala, Sweden).

To reduce non-specific binding to the reference surface, HBS-P+ (GE Healthcare, Uppsala, Sweden) supplemented with 1% BSA w/v (Sigma, Dorset, UK) was used as the running buffer and was also used for dilution of ligand and analyte. The supernatant containing IgG was diluted in the running buffer to 1 µg/mL. At the beginning of each cycle, the antibody was loaded onto Fc2, Fc3, and Fc4 on the anti-human sensor chip (GE Healthcare, Little Chalfont, UK). The IgG antibody was captured at a flow rate of 10 μl/min to achieve an immobilization level (RL) of ~208 RU. Then, the surface was allowed to stabilize.

To minimize potential mass transfer effects, recombinant human TIGIT (from Sino Biological) was used as the analyte and injected at a flow rate of 40 μl/min to obtain Single cycle kinetic data. The antigen was diluted in the running buffer in a concentration range of 1.25 nM to 10 nM, with a 2-fold dilution (at four points), and used without regeneration between individual concentrations. For each of the four increasing antigen concentrations, the association phases were monitored for 210 seconds, and after the last antigen injection, a single dissociation phase was measured for 900 seconds. The sensor chip surface was regenerated by a single injection of 3 M $MgCl_2$.

Double referenced sensorgrams were fitted with the Langmuir (1:1) binding model, and the fit of the data to the model was evaluated using the Chi square value, which describes the deviation between the experimentally obtained curve and the fitted curve (observed vs. predicted). The fitting algorithm aims to minimize the Chi square value. The kinetic constants determined from the 1:1 model fitted curves are shown in Table 10.

TABLE 10

| Antibody | $k_a$(1/Ms) | $k_d$(1/s) | $K_D$(M)* | Relative $K_D$ | $R_{MAX}$ | Chi$^2$(RU$^2$) |
|---|---|---|---|---|---|---|
| VH0Vκ0 | 2.46E+06 | 1.60E−03 | 6.52E−10 | 1.00 | 32.4 | 0.0604 |
| VH1Vκ1 | 2.33E+06 | 1.29E−03 | 5.54E−10 | 0.85 | 25.2 | 0.012 |
| VH1Vκ2 | 1.80E+06 | 1.46E−03 | 8.11E−10 | 1.24 | 28.8 | 0.0374 |
| VH1Vκ3 | 1.89E+06 | 1.82E−03 | 9.63E−10 | 1.48 | 27.2 | 0.0306 |
| VH1Vκ4 | 1.91E+06 | 1.67E−03 | 8.76E−10 | 1.34 | 25.4 | 0.0175 |
| VH1Vκ5 | 1.80E+06 | 1.29E−03 | 7.17E−10 | 1.10 | 33.9 | 0.0428 |
| VH2Vκ1 | 2.36E+06 | 1.68E−03 | 7.15E−10 | 1.10 | 25.5 | 0.0234 |
| VH2Vκ2 | 1.65E+06 | 1.58E−03 | 9.61E−10 | 1.47 | 28.4 | 0.0214 |
| VH2Vκ3 | 1.49E+06 | 1.34E−03 | 8.97E−10 | 1.38 | 31.2 | 0.0198 |
| VH2Vκ4 | 1.75E+06 | 1.81E−03 | 1.03E−09 | 1.58 | 31.9 | 0.0333 |
| VH2Vκ5 | 1.72E+06 | 1.30E−03 | 7.54E−10 | 1.16 | 27 | 0.00959 |
| VH3Vκ1 | 2.17E+06 | 1.55E−03 | 7.15E−10 | 1.10 | 24.6 | 0.0188 |
| VH3Vκ2 | 1.80E+06 | 1.73E−03 | 9.63E−10 | 1.48 | 25.1 | 0.00968 |
| VH3Vκ3 | 1.66E+06 | 1.50E−03 | 9.03E−10 | 1.38 | 26.4 | 0.0168 |
| VH3Vκ4 | 1.63E+06 | 1.96E−03 | 1.20E−09 | 1.84 | 29.8 | 0.0317 |
| VH3Vκ5 | 1.85E+06 | 1.61E−03 | 8.71E−10 | 1.34 | 25.1 | 0.0123 |
| VH4Vκ1 | 1.73E+06 | 1.07E−03 | 6.16E−10 | 0.94 | 27.4 | 0.0479 |
| VH4Vκ2 | 1.75E+06 | 1.85E−03 | 1.06E−09 | 1.63 | 29.4 | 0.025 |
| VH4Vκ3 | 1.85E+06 | 1.75E−03 | 9.44E−10 | 1.45 | 27.2 | 0.0644 |
| VH4Vκ4 | 1.49E+06 | 1.92E−03 | 1.29E−09 | 1.98 | 30.1 | 0.0209 |
| VH4Vκ5 | 1.76E+06 | 1.62E−03 | 9.22E−10 | 1.41 | 24.5 | 0.0117 |
| VH5Vκ1 | 1.45E+06 | 1.24E−03 | 8.58E−10 | 1.32 | 30.5 | 0.008 |
| VH5Vκ2 | 1.23E+06 | 2.04E−03 | 1.66E−09 | 2.55 | 28.2 | 0.026 |
| VH5Vκ3 | 1.25E+06 | 1.89E−03 | 1.51E−09 | 2.32 | 34.1 | 0.0257 |
| VH5Vκ4 | 1.19E+06 | 1.81E−03 | 1.52E−09 | 2.33 | 29.3 | 0.022 |
| VH5Vκ5 | 1.36E+06 | 1.70E−03 | 1.25E−09 | 1.92 | 33 | 0.007 |

Table 10 displays the single cycle kinetic parameters for the binding of the chimeric antibody (VH0/Vκ0) and humanized variants to the human TIGIT antigen, as measured using Biacore T200. The relative $K_D$ was calculated by dividing the $K_D$ of the humanized variants by the KD of the VH0/Vκ0 chimeric antibody, analyzed in the same experiment.

As shown in Table 10, the $K_D$ values related to the binding of all tested humanized variants (antibodies) to human TIGIT were found to be up to 2.55 times higher than that of VH0/Vk0. Considering the relative expression level, humanness percentages, and the relative $K_D$ values (obtained from Biacore single cycle kinetics analysis on supernatants), six humanized variants (VH2/Vκ5, VH3/Vκ4, VH3/Vκ5, VH4/Vκ4, VH4/Vκ5, and VH5/Vκ5) were selected for subsequent thermal stability analysis.
1.5. Thermal Stability Assessment To obtain information on the thermal stability of the antibody from the temperature at which it transitions from its native state to a denatured state (unfolding), a thermal ramp stability experiment (Tm and Tagg) was performed. Such unfolding processes occur over a narrow temperature range, and the midpoint of such a transition is called the "melting temperature" or "Tm". Since the protein undergoes a conformational change at this point, the fluorescence of Sypro Range (which binds to the exposed hydrophobic regions of the protein) was measured to determine the protein's melting temperature.

The samples were diluted in PBS to a final test concentration of 0.5 mg/ml, and Sypro™ Orange (160× Stock solution; Sigma-Aldrich) was added to a final concentration of 20× solution. Each sample mixture was loaded twice into UNi microcuvettes, 9 μL each. A thermal ramp from 15° C. to 95° C. was applied to the samples (with a ramp rate of 0.3° C./minute and excitation at 473 nm). The complete emission spectrum was measured from 250 to 720 nm, and the area under the curve between 510-680 nm was used to calculate the inflection points of the transition curve (Tonset and Tm). Static light scattering (SLS) at 473 nm was monitored to detect protein aggregation, and the Tagg (aggregation onset) was calculated from the resulting SLS profile. Data analysis was performed using UNcle™ software version 4.0 (ABZENA).

The results obtained are summarized in Table 11 below:

TABLE 11

| Antibody | $T_m$1(° C.) Average | SD | $T_{onset}$1(° C.) Average | SD | $T_{agg}$1(° C.)(473 nm) Average | SD |
|---|---|---|---|---|---|---|
| VH0Vκ0 | 70.0 | 0.59 | 61.9 | 0.01 | 80.2 | 0.43 |
| VH2Vκ5 | 68.8 | 0.32 | 60.8 | 0.89 | 79.6 | 0.34 |
| VH3Vκ4 | 68.3 | 0.21 | 60.5 | 0.35 | 79.6 | 0.20 |
| VH3Vκ5 | 67.4 | 0.22 | 60.0 | 0.07 | 76.4 | 0.16 |
| VH4Vκ4 | 67.6 | 0.11 | 60.2 | 0.15 | 78.8 | 0.15 |
| VH4Vκ5 | 67.7* | N/A | 60.2* | N/A | 76.3 | 0.08 |
| VH5Vκ5 | 67.8 | 0.21 | 60.6 | 0.3 | 77.6 | 0.18 |

Table 11 shows thermal stability values obtained using the UNcle biostability platform. As shown in Table 11, all the humanized antibodies tested exhibited similar levels of thermal stability as the chimeric antibody.
1.6. Affinity Measurement of Humanized Variants Using Multi-Cycle Kinetic Analysis To measure the binding affinity of the chimeric antibody and the six leading humanized variants (VH2/Vκ5, VH3/Vκ4, VH3/Vκ5, VH4/Vκ4, VH4/Vκ5, and VH5/Vκ5) for the human TIGIT antigen, multi-cycle kinetic analysis was conducted on the purified proteins (antibodies). Kinetic experiments were performed at 25° C. using a Biacore T200 operated with Control software V2.0.1 and Evaluation software V3.0 (GE Healthcare, Uppsala, Sweden).

HBS-P+ (GE Healthcare, Uppsala, Sweden) supplemented with 1% BSA w/v (Sigma, Dorset, UK) was used as the running buffer and was also used for dilution of ligands and analytes. The purified leading antibodies were diluted in the running buffer to a final concentration of 1 μg/mL, and at the initiation of each cycle, were loaded onto Fc2, Fc3, and Fc4 sites on the anti-human IgG CM5 sensor chip (GE Healthcare, Little Chalfont, UK). The antibodies were captured at a flow rate of 10 µl/min until a response level (RL) of ~150 RU was achieved, followed by a stabilization period.

To minimize potential mass transfer effects, recombinant human TIGIT (Acrobiosystems, China) was introduced as the analyte at a flow rate of 50 µl/min to obtain multi-cycle kinetic data. The antigen (TIGIT) was two-fold diluted in running buffer from 0.406 nM to 30 nM (7 points), and each concentration was applied without regeneration between cycles. For each concentration, association phases were monitored for 240 seconds, followed by 900 seconds of monitoring the dissociation phase. The sensor chip surface was regenerated between kinetic cycles by injecting 3M $MgCl_2$ twice. To ensure the stability of both the surface and the analyte across kinetic cycles, repetitive injections of blank and a single concentration of the analyte were programmed into the kinetic run.

Results obtained from the above experiment, specifically for the chimeric antibody (VH0/Vκ0) and the VH3/Vκ5 antibody, are summarized and presented in Table 12:

TABLE 12

| Antibody | Analyte | ka(1/Ms) | Kd(1/s) | KD(M) | RMAX | Chi2 (RU2) |
|---|---|---|---|---|---|---|
| VH0/Vk0 | hTIGIT | 2.28E+06 | 1.76E−04 | 7.70E−11 | 28.2 | 0.425 |
| VH3/Vk5 | hTIGIT | 2.04E+06 | 1.77E−04 | 8.67E−11 | 26 | 0.246 |

Table 12 shows kinetic constants determined from 1:1 model fitted curves. As shown in Table 12, the binding affinity (KD) for the human TIGIT protein was 77 PM for antibody 7A6 VH0Vk0 and 86.7 PM for antibody VH3/Vk5, which are similar to each other.

1.7. Epitope Mapping

The antibody's epitope was identified through peptide mass fingerprint (PMF) and H/D exchange (hydrogen/deuterium exchange).

To detect the incorporation of deuterium atoms in TIGIT and the mixture of TIGIT and antibody 7A6 Vh3/Vk5, the peptide mass fingerprint (PMF) of the samples was optimized. Proteolytic digestion of protein samples was performed under quenched conditions to limit the reverse exchange of deuterium atoms that might occur during protein digestion and chromatography.

Solutions of TIGIT (SEQ ID NO: 30; NCBI Reference Sequence NP_776160.2; UniProtKB/SwissProt Q495A1-1) (15 µM, 150 µl) and a mixture of TIGIT and Vh3Vk5 with a ratio of TIGIT: Vh3Vk5=(15 µM: 30 µM, 150 µl) were prepared. Four µl of the above protein sample was mixed with 56 µl of labeling buffer (5 mM $K_2HPO_4$; 5 mM $KH_2PO_4$, $D_2O$ pH 6.6) for the exchange experiment and with 56 µl of equilibration buffer (5 mM $K_2HPO_4$; 5 mM $KH_2PO_4$, pH7.0) for the control experiment. A 15× diluted solution (60 µl, TIGIT: Vh3Vk5; 1 µM: 2 µM) was incubated for 15 seconds, 60 seconds, 180 seconds, 600 seconds, 1800 seconds, and 7200 seconds, respectively, after which 50 µl of quench solution (50 mM $K_2HPO_4$; 50 mM $KH_2PO_4$; GuCl 2.0 M, TCEP 200 mM, pH 2.3, 0° C.) was added to the protein sample and incubated for an additional 20 seconds. After incubation, 80 µl of the quenched protein solution was immediately injected into a proteolytic pepsin column and kept at 15° C. for 5 minutes. Following protein digestion, the generated pepsin peptides were analyzed using liquid chromatography with C18 chromatography (HDX Manager Waters) before the MSe Xevo-G2-XS analysis. These tests were conducted three times.

H/D exchange peptides were analyzed using the DynamX3.0 software. Deuterium levels were determined by considering the average of all results with high and medium confidence. Deuteration levels were calculated based on the centroid of the experimental isotope cluster.

From the HDX-MS analysis results, significant differences in deuterium incorporation within TIGIT were observed when incubated either alone or with 7A6 VH3/Vk5. The primary difference in deuterium incorporation was observed in the amino acid residues 51-70 (TAQVTQVNWEQQDQLLAICN; SEQ ID NO: 31), which are responsible for the epitope region of 7A6 Vh3Vk5.

The results were presented in FIGS. 3a and 3b. FIG. 3a shows the HDX-MS 20) analysis results (with high levels of deuterium incorporation at the site 51-70 (TAQVTQVNWEQQDQLLAICN; SEQ ID NO: 31) of TIGIT). FIG. 3b schematically represents the ribbon structure of TIGIT; the upper being a top view, the lower a side view, with the epitope site indicated by arrows.

1.8. Temporary Antibody Expression and Purification of Leading Humanized Antibody The heavy chain and light chain variable region sequences of 7A6 VH3/Vk5 were synthesized together with the restriction enzyme sites for cloning vector construction. The synthesized sequences of the heavy chain and light chain were treated with the appropriate restriction enzymes (heavy chain: Mlu I and Sal I (New England Biolabs); light chain: BssH II and BamH I (New England Biolabs)), and ligated into the expression vector containing the human IgG1 constant region treated with the same restriction enzymes. Both the heavy chain and light chain cDNA constructs were sequenced. Giga prep was performed to prepare DNA for transient transfection in CHO cells. The Giga prep was conducted using the PureLink™ HiPure Expi Plasmid Gigaprep Kit (Thermo Fisher Scientific, K210009XP). This Gigaprep kit is designed to amplify plasmid DNA in E. coli and then purify it using anion exchange chromatography. CHO cells (Evitria) were cultured using an animal component-free and serum-free medium (CD CHO Medium, Thermofisher). The produced antibody was purified from the culture supernatant by the Protein A purification method using the MabSelect™SuRe™. Sequential purification was performed using size exclusion chromatography (SEC) to achieve a purity of more than 95%. The purified antibody was characterized by measuring absorbance at 280 nm and through SDS-PAGE.

1.9. Specificity and Binding Affinity for TIGIT in Human Primary T Cells

The anti-TIGIT 7A6 VH3/Vk5 antibody was conjugated with Alexa Fluor®488 (AF488) using the APEX™ antibody labeling kit (Invitrogen) according to the manufacturer's instructions. T cells were isolated from human PBMCs using magnetic beads (EasySep™) and were cultured with various concentrations of the labeled anti-TIGI antibody (anti-TIGIT 7A6 VH3/Vk5 antibody; 50, 250, 750, 1250, and 2500 ng/ml). The binding was measured using a flow cytometer (CytoFLEX, Beckman Coulter), and the obtained data were analyzed using FlowJo software (TreeStar, Inc).

The binding of the anti-TIGIT antibody was confirmed on $CD3^+$, $CD4^+$, and $CD8^+$ T cells.

The obtained results are depicted in FIG. 4. As shown in FIG. 4, the tested anti-TIGIT antibody bound to primary T cells, and the binding to TIGIT molecules (per cell) increased as the concentration of the anti-TIGIT antibody increased.

Reference Example: Preparation of Reference Antibodies

Reference antibodies used as references in the following Examples were constructed on the basis of the sequence information disclosed in corresponding patents or purchased from the manufacturers. The corresponding patents or manufacturers of each antibody are summarized below:

22G2 (BMS): US2016/0176963 A1,
31C6 (Merck): WO2016/028656 A1,
4.1D3 (Genentech): WO2017/053748 A2,
TIG1 (Arcus): WO2017/152088 A1,
313M32 (Mereo): US2016/0376365 A1,
Tiragolumab (Roche): purchased from CrownBio,
10A7 (Genentech): purchased from Creative Biolabs,
MBSA43: purchased from eBioscience,
Pembrolizumab and Nivolumab: purchased from Invivo-
Gen.

Example 2. Measurement of Biological Activity of Anti-Tigit Antibody by Cell-Based Reporter Assay The blocking effect of the anti-TIGIT antibody on the interaction between TIGIT and its receptor, that is, poliovirus receptor (PVR) (TIGIT-PVR blocking effect), was analyzed using a cell-based NFAT reporter response bioassay (Promega). TIGIT effector cells (Promega) were added to the cell assay buffer (90% RPMI 1640/10% FBS) and the cell suspension containing the TIGIT effector cells was incubated at 37° C. for 16 hours. The anti-TIGIT antibody (7A6 VH3/Vk5) or a reference antibody was prepared in PBS buffer and added to the pre-incubated cell suspension. CD155 aAPC/CHO-K1 cells (Promega) were added to the mixture containing the cells and antibody and cultured at 37° C. for 6 hours. The luminescence was measured using the Promega™ GloMax® Plate Reader. The $EC_{50}$ value of the antibody response was measured using curve fitting software (GraphPad Prism® software).

The obtained results are depicted in FIG. 5. As indicated in FIG. 5, the activation signal of T cells increased due to the TIGIT-PVR blocking by the anti-TIGIT 7A6 VH3/Vk5 antibody. The anti-TIGIT 7A6 VH3/Vk5 antibody of the present application showed a considerably higher effect (significantly lower $EC_{50}$ value) compared to the reference antibodies such as BMS (22G2), Arcus (TIG1), Genentech (4.1D3), and Mereo (313M32).

Example 3: Cytokine Production Effect of Anti-Tigit Antibody

3.1. Preparation of Human PBMCs and Tumor Infiltrating Lymphocytes

Peripheral blood mononuclear cells (PBMC) were obtained from adults (whole blood leukocyte cones, NHS Blood and Transplant, UK) or purchased from STEMCELL Technologies. Trials for this working example were conducted on hepatocellular carcinoma (HCC) patients and healthy normal donors after appropriate ethical review and prior consent from the "Centre for Liver and Gastrointestinal Research, University of Birmingham, UK". PBMCs and liver-derived lymphocytes were prepared from liver tissue obtained from HCC patients. Liver-infiltrating lymphocytes were isolated from a 0.5-1 cm hepatic needle biopsy. Subsequently, the tissue was homogenized in 2-3 ml of Dulbecco's Phosphate-Buffered Saline (GIBCO) using a Dounce tissue grinder. PBMCs from patients with melanoma, ovarian cancer, CRC (Colorectal cancer), HCC, NSCLC (non-small cell lung cancer), and pancreatic cancer were acquired from Cureline, Inc. The obtained liver-infiltrating lymphocytes and PBMCs from cancer patients were then analyzed as follows.

3.2. Measurement of Cytokine Production in Human PBMCs 3.2.1. Increased Cytokine Secretion in Human PBMCs by Anti-TIGIT Antibody PBMCs were cultured with the anti-CD3 antibody in the presence of the anti-TIGIT 7A6 VH3/Vk5 antibody (2 ug/ml and 10 ug/ml). A group untreated with the anti-TIGIT antibody was used as a control. After culturing, the samples were centrifuged at 400×g for 10 minutes, and the supernatant was used for the multiplex immunoassay. Cytokine concentrations were measured using the Bio-Plex cytokine assay (Human cytokine Assay including IFN-gamma, IL-2). All analyses were performed according to the manufacturer's instructions, and the results were read on the Bio-Plex 200 array reader (Bio-Rad).

The obtained results (IFN-gamma and IL-2 concentrations) are shown in FIG. 6. As depicted in FIG. 6, the anti-TIGIT 7A6 VH3/Vk5 antibody significantly induced Th1/Tc1 cytokine secretion in human PBMCs. Unless otherwise specified in the description and drawings, the anti-TIGIT 7A6 VH3/Vk5-IgG1 is denoted as the anti-TIGIT 7A6 antibody or the anti-TIGIT 7A6 VH3/Vk5 antibody.

3.2.2. Increased Cytokine Production in Human T Cells by Anti-TIGIT Antibody

Cytokine production was measured in human T cells (CD4+ T cells and CD8+ T cells). Cells (500,000 cells/ reaction) were cultured with anti-CD3 monoclonal antibody (BD Biosciences, cat no. 555336; 0.2 ug/ml) and anti-CD28 monoclonal antibody (BD Biosciences, cat no 555725; 1 ug/ml) in the presence of the anti-TIGIT 7A6VH3/Vk5 antibody. After cultivation, the cells were spun down at 400×g for 10 minutes at 4° C., and cytokine concentrations inside the T cells were measured. In this regard, intracellular cytokines were stained as follows: cells were stained with Zombie Aqua fixable dead cell dye solution (Biolegend), and labeled with fluorophore-conjugated antibodies for CD4+ and CD8+ T cell surface markers for 30 minutes on ice. The used anti-CD3, anti-CD4, and anti-CD8 antibodies (all used for staining CD4+ and CD8+ T cell surfaces), anti-IL-2, anti-IFNg, and anti-TNFa antibodies were all acquired from Biolegend.

Using the eBioscience™ Foxp3/Transcription Factor Fixation/Permeabilization Concentrate and Diluent kit (eBiosciences), cells were fixed and permeabilized according to the manufacturer's instructions. The cells were then stained with fluorophore-conjugated antibodies for intracellular IL-2, IFNγ, and TNFaα (Biolegend). The cells were analyzed with a flow cytometer (CytoFLEX, Beckman Coulter) and the data was analyzed using the FlowJo software (BD Biosciences).

The results were depicted in FIGS. 7*a* (CD4+ T cells) and 7*b* (CD8+ T cells). As depicted in FIGS. 7*a* and 7*b*, the anti-TIGIT 7A6 VH3/Vk5 antibody of this application increased the production of Th1/Tc1 cytokines (IL-2, IFN-gamma) inside the T cells, demonstrating its effect of enhancing the immune response. The obtained results suggest that the anti-TIGIT 7A6 VH3/Vk5 antibody has a potent effect of enhancing the function of effector T cells in a dose-dependent manner.

3.3. Comparison of Efficacy between Anti-TIGIT Antibody and Reference Antibodies
3.3.1. Enhanced Immunopotentiating Effect of Anti-TIGIT Antibody Compared to Anti-PD1 Drugs The immunological effect of the anti-TIGIT antibody on cytokine production was measured using the method described in Example 3.2.2. For comparison, anti-PD1 antibodies, pembrolizumab (indicated as 'Pem analog') and nivolumab (indicated as 'Niv analog'), were used as reference antibodies. The analysis was conducted by performing flow cytometry after treatment with either the anti-TIGIT antibody or the anti-PD1 antibody. Both the anti-PD-1 antibody and the anti-TIGIT antibody were used at 10 ug/ml each.

The results obtained are depicted in FIGS. 8a (IL-2 concentration in CD4+ T cells), 8b (IFN-gamma concentration in CD4+ T cells), 8c (IL-2 concentration in CD8+ T cells), and 8d (IFN-gamma concentration in CD8+ T cells). As indicated in FIGS. 8a-8d, the anti-TIGIT 7A6VH3/Vk5 antibody induced a higher level of CD4+ and CD8+ T cell activation, compared to pembrolizumab or nivolumab.
3.3.2. Enhanced Th1/Tc1 cytokine Production Effects of Anti-TIGIT 7A6 Antibody Compared to Reference Anti-TIGIT Antibodies After culturing T cells with various concentrations (2 ug/ml, 5 ug/ml, 10 ug/ml) of the anti-TIGIT antibody, cytokine production was measured using the method described in Example 3.2.2. The reference anti-TIGIT antibodies used for comparison were as described in the foregoing.

The results obtained are shown in FIGS. 9a (IL-2 concentration in CD4+ T cells), 9b (IFN-gamma concentration in CD4+ T cells), 9c (IL-2 concentration in CD8+ T cells), and 9d (IFN-gamma concentration in CD8+ T cells). As depicted in FIGS. 9a-9d, the anti-TIGIT 7A6V H3/Vk5 antibody was observed to enhance the immune response by increasing Th1/Tc1 IFN-gamma and IL-2 cytokine production. The anti-TIGIT 7A6 VH3/Vk5 antibody demonstrated a more potent increase in cytokine production, compared to the comparative anti-TIGIT antibodies.

Example 4. Effect of Anti-Tigit Antibody on T Cell Proliferation 4.1. Effect of Anti-TIGIT Antibody on T Cell Proliferation in Human PBMCs Anti-TIGIT antibody (7A6 VH3/Vk5-IgG1 or 7A6 VH3/Vk5-IgG4) at 10ug/ml was co-cultured with plate-bound anti-CD3 antibody (BD Biosciences) (0.2 ug/ml), PBMCs (500,000 cells/reaction), and Cytostim activator (Miltenyi Biotec). After culturing, measurement was made of CFSE (carboxyfluorescein succinimidyl ester) on the Incucyte® Live-Cell analysis system (Satorius) and of Ki67 on a flow cytometer.

The results obtained are shown in FIG. 10a (CFSE assay results) and FIG. 10b (Ki67 assay result) (No Stim: neither cytostim activator nor antibody treatment; Control: no antibody treatment). As shown in FIGS. 10a and 10b, the anti-TIGIT antibodies 7A6 VH3/Vk5-IgG1 and 7A6 VH3/Vk5-IgG4 of this application both induced T cell proliferation, suggesting that the immune response induced by the anti-TIGIT antibodies can persist for an extended period.
4.2. Blocking Effect of Anti-TIGIT Antibody on the Inhibition of T Regulatory Cells against CD8+ T Cell Proliferation CD8+ T cells and Tregs (T regulatory cells) were isolated using the human CD8+ T Cell Isolation Kit (Miltenyi Biotec 130-096-495) and the CD4+ CD25+ CD127-dim reg T cell isolation kit II (130-094-775). The separated CD8+ T cells were stained with the cell tracker violet proliferation kit (Thermo Fisher) and seeded so that the CD8:Treg ratio was 4:1. The cells were activated with CD3/CD28 Dynabeads (ThermoFisher) and anti-TIGIT 7A6 VH3/VK5 antibody at 10 ug/ml was added to the appropriate wells. On day 3, the beads were washed off, and IL-2 at 50 ng/ml was added. On day 7, cells were stained with surface marker antibodies for live/dead (ThermoFisher LIVE/DEAD™ Fixable Near-IR Dead Cell Stain Kit), CD3, CD8, and CD4 (all obtained from Biolegend) and analyzed on a flow cytometer (Cyto-Flex, Beckman Coulter).

The results obtained are shown in FIG. 11. As indicated in FIG. 11, the proliferation of CD8+ T cells decreased with the addition of Tregs, but this inhibition of CD8+ T cell proliferation was blocked by the anti-TIGIT antibody. This implies that the anti-TIGIT antibody blocks the Tregs-mediated inhibition of CD8+ T cell proliferation.

Example 5. Synergistic Effect of Combination of Anti-Tigit Antibody and Anti-PD1 Drug 5.1. Biological Characterization of Anti-TIGIT/anti-PD1 Antibodies via Cell-Based Reporter Assay The synergistic effect of a combination of the anti-TIGIT antibody and the anti-PD antibody (pembrolizumab or nivolumab) was tested. The combined blocking effect of the anti-TIGIT antibody and the anti-PD antibody on TIGIT-PVR and PD-1-PD-L1 was analyzed using a cell-based NFAT reporter response bioassay (Promega). PD-1+TIGIT+ effector cells (Promega; $1\times10^5$ cells/reaction) were added to cell assay buffer (90% RPMI 1640/10% FBS) and the resulting cell suspension containing PD-1+TIGIT+ effector cells was cultured at 37° C. for 16 hours. PD-L1+CD155 aAPC/CHO-K1 cells (Promega; $4\times10^4$ cells/reaction) were prepared in cell recovery medium (90% Ham's F-12, 10% FBS). A mixture of the anti-TIGIT TIGIT+VH3/Vk5 antibody and either pembrolizumab or nivolumab was added to the cell suspension containing the PD-1+TIGIT+ effector cells ($1\times10^5$/reaction) and PD-L1+CD155 aAPC/CHO-K1 ($4\times10^4$/reaction), and cultured at 37° C. for 6 hours. For a control, the anti-TIGIT antibody or the anti-PD1 antibody was applied alone. When used alone, the antibody was applied at a concentration of 0.02048, 0.512, 1.28, 3.2, 8, or 20 (ug/ml). For the combination treatments, the anti-TIGIT antibody was used at a concentration of 0.02048, 0.512, 1.28, 3.2, 8, or 20 (ug/ml) while the concentration of the anti-PD-1 antibody (Pembrolizumab or Nivolumab) was also 0.02048, 0.512, 1.28, 3.2, 8, or 20 (ug/ml).

After culturing, the Bio-Glo Reagent was added and incubated at ambient temperature for 10 minutes. Luminescence was measured with the Promega™ GloMax® Plate Reader. The $EC_{50}$ value of the antibody response was determined using curve fitting software (GraphPad Prism® software).

The results obtained are shown in FIG. 12. As shown in FIG. 12, a combination of the anti-TIGIT antibody with either pembrolizumab or nivolumab was observed to exhibit a synergistic effect.
5.2. Comparison of Biological Activity between Anti-PD1/Reference Antibody and Anti-TIGIT/Anti-PD1 Antibodies The combined effect of the anti-TIGIT antibody and anti-PD1 antibody for blocking TIGIT-PVR/PD-1-PD-L1 was analyzed using a cell-based NFAT reporter response bioassay (Promega). The anti-TIGIT antibody (7A6) or a reference anti-TIGIT antibody was co-cultured with pembrolizumab or nivolumab, referring to Example 5.1. For comparison, the reference antibody was cultured with the cell mixture and treated in the same manner.

When applied alone, the antibody was used at a concentration of 0.013, 0.032, 0.082, 0.204, 0.512, 1.28, 3.2, 8, or 20 (ug/ml). For combination treatments, the concentration of the anti-TIGIT antibody was 0.013, 0.032, 0.082, 0.204, 0.512, 1.28, 3.2, 8, 20 (ug/ml), and the concentration of the anti-PD-1 antibody (Pembrolizumab or Nivolumab) was also 0.013, 0.032, 0.082, 0.204, 0.512, 1.28, 3.2, 8, 20 (ug/ml).

The results obtained are shown in FIG. 13a (in combination with pembrolizumab) and 13b (in combination with nivolumab). As shown in FIGS. 13a and 13b, the anti-TIGIT antibody combined with pembrolizumab and nivolumab exhibited a higher enhancing effect compared to the combination of the anti-PD1 antibody and the reference anti-TIGIT antibody.

5.3. Immunological Effect of Anti-TIGIT/Anti-PD1 Antibodies on Immune T Cells

The cytokine production of human T cells during combination or single treatment with anti-TIGIT/anti-PD1 antibodies was measured. The anti-TIGIT antibody 7A6 VH3/Vk5 (2 ug/ml) was pre-mixed with pembrolizumab (2 ug/ml) or nivolumab (2 ug/ml) and added to the cell culture. Referring to Example 3.2.2, intracellular cytokines were stained.

The results obtained are shown in FIGS. 14a (CD4+ cells) and 14b (CD8+ cells). As seen from the results, the anti-tumor activity based on Tc1/Th1 cytokine production in human primary T cells was enhanced when the anti-TIGIT 7A6VH3/Vk5 antibody and the anti-PD1 antibody were used in combination.

Example 6: Assay for Cytotoxicity of Anti-Tigit Antibody Against Tumor Cells 6.1. Expression Level of TIGIT ligand PVR (CD155) in Tumor Cells The target tumor cells (A375 and SK-OV3 cells) (ATCC) were stained with a 1:25 diluted anti-CD155 PE-Cy7 (Biolegend) to evaluate the expression of CD155 (PVR) and analyzed using a flow cytometer.

The results obtained are presented in FIG. 15. As shown in FIG. 15, the A375 and SK-OV3 tumor cells exhibited a significant level of expression of the TIGIT ligand CD155.

6.2. Cytotoxicity of Anti-TIGIT Antibody against A375 Melanoma Cells

The anti-TIGIT antibody (7A6 VH3/Vk5 and 7A6 VH3/Vk5-DLE) at a concentration of 10 ug/ml was co-cultured with the A375 cell line (melanoma) ($2.5 \times^{10}$e4 cells/reaction) in the presence of PBMC (250,000 cells/reaction) and Cytostim (Milteni Biotec) for 72 hours to test the cytotoxicity against A375 tumor cells. For comparison, the anti-TIGIT10A7 reference antibody (Genentech) was used. Additionally, the cytotoxic capability to tumor cells of the modified anti-TIGIT antibody (7A6 VH3/Vk5-DLE) was also tested. The tumor cells were counted using the Incucyte® Live-Cell Analysis System (Satorius).

The results obtained are presented in FIG. 16. As shown in FIG. 16, the anti-TIGIT antibodies of the present application, 7A6 VH3/Vk5 and 7A6 VH3/VK5-DLE, both demonstrated enhanced tumor cell killing effects.

6.3. Cytotoxic Ability of Anti-TIGIT Antibody to Ovarian Cancer Cells 1

To verify the cytotoxic ability of the anti-TIGIT 7A6 VH3/Vk5 antibody against the SKOV-3 tumor (ovarian cancer) cell line, the SKOV-3 cells (35k cells/well) were co-cultured with PBMCs and CytoStim (1/50) in the presence or absence of the anti-TIGIT antibody (10 ug/ml) or the reference antibody (10 ug/ml). The ratio of effector cells to target cells (E:T) was set at 6:1. The reference antibodies used were anti-TIGIT antibody Mereo/313M32, BMS/22G2, Genentech/4.1D3, and Arcus/TIG1 (refer to the Reference Example). The data obtained was analyzed using the Incucyte® Live-Cell Analysis System (Sartorius) and IncuCyte native software.

The results are presented in FIGS. 17a (cell death rate over culturing time) and 17b (cell death rate after 84 days of culturing). As shown in FIGS. 17a and 17b, the anti-TIGIT 7A6VH3/Vk5 antibody was observed to have increased cytotoxicity against the tumor cells, and this cytotoxic ability was significantly higher compared to the reference antibodies.

6.4. Cytotoxic Ability of Anti-TIGIT Antibody to Ovarian Cancer Cells 2

To test the cytotoxicity of the anti-TIGIT antibody (anti-TIGIT 7A6VH3/Vk5 and 7A6VH4/Vk4, each at 10 ug/ml) against SKOV-3 ovarian cancer cells, SKOV-3 cells (35k cells/well) were co-cultured with isolated CD8+ T cells and Cytostim for 108 days in the presence or absence of the anti-TIGIT antibody. The ratio of effector cells to target cells (E:T) was set at 3:1. A group treated with pembrolizumab in the same way served as a control. The data was analyzed using IncuCyte native software.

The results are presented in FIG. 18. As is understood from the results, the anti-TIGIT 7A6VH3/Vk4 antibody was observed to exhibit increased cytotoxicity against the tumor cells, and this cytotoxic ability was significantly higher compared to pembrolizumab.

6.5. Enhanced Cytotoxicity of NK cells against SKOV3 Tumor Cells by TIGIT-CD155 (PVR) Blocking NK cells were pre-stimulated for 48 hours with or without IL-15 (5 ng/ml). These NK cells were isolated from human PBMCs using the NK isolation kit (NK Cell Isolation Kit, from Miltenyi Biotec (cat. No. 130-092-657)) according to the manufacturer's instructions. After culturing, the NK cells (250,000 cells/reaction) were co-cultured with the SKOV3 cells ($2.5 \times^{10}$e4 cells/reaction) for 48 hours in the presence of the anti-TIGIT antibodies (7A6 VH3/VK5, 7A6 VH4/Vk4, 7A6 VH3/Vk5-DLE) each at 10 ug/ml, with the E:T ratio set at 10:1. The tumor cells were counted, using the Incucyte® Live-Cell Analysis System (Sartorius).

The results are presented in FIG. 19. As shown, all tested anti-TIGIT antibodies significantly increased the cytotoxic ability of NK cells against SKOV3 tumor cells.

Example 7: Assay for In Vivo Anticancer Efficacy 7.1. Assay for In Vivo Efficacy of Anti-TIGIT Antibody in MC38 Colon Cancer Model Human PVR (MC38-hPVR)-expressing MC38 colon cancer cells (CrownBio) were in vitro stored at 37° C. in DMEM medium supplemented with 10% FBS (fetal bovine serum) and 4 ug/ml puromycin under a 5% $CO_2$ atmosphere. Cells in the exponential growth phase were harvested and quantified with a cell counter prior to tumor inoculation.

The prepared tumor cell solution ($2 \times 10^5$ tumor cells in 0.1 mL of PBS solution) was subcutaneously injected into the right flank of the C57BL6 hTIGIT knock-in mouse (from GemPharmatech Co., Ltd.) to induce tumor growth. Randomization was performed when the average tumor size (volume) reached 80-100 mm³. A total of 15 mice were used in this experiment and they were randomly divided into three groups (5 mice/group).

After tumor cell inoculation, the pathological state and mortality of the animals were checked daily, and weight increase/decrease was measured three times a week after randomization. Mortality and observed clinical symptoms were recorded daily for each animal. Tumor size (volume) was measured bi-dimensionally using a caliper three times a week after randomization and calculated using the formula:

$$V(mm^3) = (L \times W \times W)/2$$

[where V is the tumor volume (mm$^3$), L is the length of tumor (the longest axis of tumor), and W is the width (the longest length perpendicular to L)].

Inoculation, tumor size, and weight measurement were performed in a Laminar Flow Cabinet. The weight and tumor size were measured using StudyDirector™ software (version 3.1.399.19).

Immediately after grouping, treatment with the antibody or vehicle was carried out. PBS solution was used as a vehicle (control; group 1), and 7A6 VH3/Vk5 produced from CHO cells and Tiragolumab were each treated at a dose of 20 mg/kg (respectively, groups 2 and 3) (see Table 13).

TABLE 13

| Group | Treatment | Dose Level (mg/kg) | Dosing Solution (mg/mL) | Dosing Volume (μL/g) | ROA | Dosing Frequency & Duration |
|-------|-----------|------|------|------|------|------|
| 1 | Vehicle | — | — | 10 | i.p. | BIW x 3 weeks |
| 2 | 7A6 VH3/Vk5 | 20 | 2 | 10 | i.p. | BIW x 3 weeks |
| 3 | Tiragolumab | 20 | 2 | 10 | i.p. | BIW x 3 weeks |

BIW: Bi-weekly (twice a week)
i.p.: intraperitoneal injection

During the test period, there was no observed weight loss in the groups injected with the antibodies (groups 2 and 3; a dose of 20 mg/kg i.p. injection).

The tumor sizes of the mice, as measured above, are presented in FIG. 20.

As seen in FIG. 20, the 7A6 VH3/Vk5 antibody showed a significant inhibitory effect on tumor growth, compared to the PBS control group, on the 21$^{st}$ day after antibody treatment. When analyzing the size of MC38 tumors between test groups on a matching day using an unpaired t-test, the tumor growth inhibitory effect by the 7A6 VH3/Vk5 antibody was especially pronounced on day 9 (p-value, 0.029) and day 21 (p-value, 0.007) compared to the control group. The 7A6 VH3/Vk5 antibody (group 2) also demonstrated superior anti-tumor efficacy compared to the comparator antibody Tiragolumab (group 1) (e.g., on day 21, p-value, 0.013).

Tumor growth inhibition (ΔTGI) was calculated as mean % ΔInhibition:

$$\Delta TGI(\text{Mean } \% \text{ } \Delta Inhibition) =$$

$$((\text{mean}(C) - \text{mean}(C0)) - (\text{mean}(T) - \text{mean}(T0)))/$$

$$(\text{mean}(C) - \text{mean}(C0)) * 100\%$$

[T: Tumor size of the test group at the measurement point, T0: Initial tumor size of the test group, C: Tumor size of the control group at the measurement point, and C0: Initial tumor size of the control group]

The tumor growth inhibition (TGI) for the 7A6 VH3/Vk5 antibody was 67.9%, showing an enhanced inhibitory effect compared to Tiragolumab (TGI=55.2%).

7.2. In Vivo Assay for Enhancement of Antitumor Efficacy by Ttreatment with Anti-TIGIT Antibody and Anti-PD1 Antibody in Combination in a CT26 Colon Cancer Model CT-26 tumor cells (CrownBio) were maintained in vitro in RPMI1640 medium supplemented with 10% FBS at 37° C. under a 5% $CO_2$ atmosphere. Cells in the exponential growth phase were harvested and quantified using a cell counter prior to tumor cell inoculation.

A prepared tumor cell solution ($5 \times 10^5$ tumor cells in 0.1 mL of PBS solution) was subcutaneously injected into the right back flank of BALB/c hPD-1/hTIGIT double knock-in mice (GemPharmatech Co., Ltd.), and tumors were allowed to grow. The day of tumor inoculation was designated as "Day 0". Randomization was performed when the average tumor size (volume) reached 70-100 mm$^3$. A total of 30 mice were used in this assay, and they were randomly divided into 5 groups (6 mice/group).

After tumor cell inoculation, the animals were measured for body weight. A PBS solution was used as the vehicle (control group; group 1), 7A6 VH3/Vk5 and 7A6 VH3/Vk5-DLE were treated at a dose of 20 mg/kg each (group 3 and group 4 respectively), anti-PD1 antibody Keytruda (Pembrolizumab; Merck) was treated at a dose of 5 mg/kg (group 4), and 7A6 VH3/Vk5 and Keytruda 5 mg/kg were administered at respective doses of 20 mg/kg and 5 mg/kg in combination (group 5).

The experiment was terminated when the mean tumor burden of the vehicle-treated group (control) reached 3000 mm$^3$ on day 25 (refer to Table 14).

TABLE 14

| Group | Treatment | Dose level (mg/kg) | Dosing Solution (mg/mL) | Dosing Volume (μL/g) | ROA | Dosing Frequency & Duration |
|-------|-----------|------|------|------|------|------|
| 1 | Vehicle | — | — | 10 | i.p. | BIW x 3 weeks |
| 2 | Keytruda | 5 | 0.5 | 10 | i.p. | BIW x 3 weeks |
| 3 | 7A6 VH3/k5 | 20 | 2 | 10 | i.p. | BIW x 3 weeks |
| 4 | Keytruda | 5 | 0.5 | 10 | i.p. | BIW x 3 weeks |
|   | 7A6 VH3/k5 | 20 | 2 | 10 | i.p. | BIW x 3 weeks |

BIW: Bi-weekly(twice a week)

TGI % was calculated according to the following equation:

$$TGI(\%) = 100 \times (1 - T/C)$$

(T and C stand for mean tumor volumes (or weights) of the test (T) and control (C) groups, respectively).

The results are summarized in Table 15 and depicted in FIG. 21.

TABLE 15

| Group | Treatment | Tumor Size (mm3) at randomization | Tumor Size (mm3) on day 25 | TGI(%) | P value Compared with control vehicle group on Day 25. (Unpaired t-test) |
|---|---|---|---|---|---|
| 1 | Vehicle | 73.39 | 2867.67 | — | — |
| 2 | Keytruda | 73.46 | 1392.99 | 51.43% | 0.022 |
| 3 | 7A6 VH3/Vk5 | 73.51 | 1264.40 | 55.91% | 0.024 |
| 4 | Keytruda + 7A6 VH3/Vk5 | 73.3 | 602.79 | 78.98% | 0.001 |

As shown in Table 15 and FIG. 21, on day 25, both the 7A6 VH3/Vk5-treated group (group 3) and the Keytruda-treated group (group 2) exhibited tumor growth reductions with TGI (Tumor Growth Inhibition) values of 51.43% and 55.91%, respectively. The combination of Keytruda and 7A6 VH3/Vk5 (Group 5) showed the most pronounced tumor formation delay and inhibitory effect with a TGI of 78.98%. On day 25, all the 7A6 VH3/Vk5-, Keytruda-, and the Keytruda+7A6 VH3/Vk5-treated groups were statistically significantly higher in tumor growth inhibitory effect than the control (p-value <0.05). Complete tumor removal was observed in the 7A6 VH3/Vk5-treated group (1 mouse) and the Keytruda +7A6 VH3/Vk5-treated group (2 mice). No significant weight differences were noted in any antibody-treated groups.

Furthermore, the effect on immune cells in the tumor microenvironment (TME) was examined and the results are depicted in FIG. 22.

For FACS analysis, tumors were dissected from euthanized mice and dissociated into single cells using the gentleMACS (Gentle MACSTM Octo Dissociator with Heaters) and Multi Tissue Dissociation Kit 1 (Miltenyi Biotech). Cells were stained with the following fluorescent-labeled antibodies against surface markers, such as anti-mouse CD45 FITC (Biolegend), anti-mouse CD3-BUV395 (BD), anti-mouse CD4-BV421 (Biolegend), anti-mouse CD8-PE-eFluor610 (eBiosciences), anti-mouse CD335 (eBiosciences), and live/dead-APC-eF780 (eBiosciences). Additionally, cells were fixed and permeabilized using the fixation/ permeabilization concentrate and diluent kit (ThermoFisher) and then stained with anti-mouse Foxp3 (eBiosciences). Cells were analyzed by flow cytometry (LSRFortessa X-20, BD), and data were analyzed using FlowJo data analysis software.

As shown in FIG. 22, the combined administration of the anti-TIGIT antibody and anti-PD1 antibody decreased the frequency of Tregs in tumors, with the resultant increase of CD3, CD4, and CD8+ T cells (FIG. 22).

7.3. In Vivo Assay for Efficacy of Anti-TIGIT Antibody in Humanized Liver Cancer Mouse Model with Patient-Derived Tumor Xenograft (PDX)

Human CD34+ hematopoietic stem cells (HSC) from cord blood of three donors (Jackson Laboratory, USA) were transplanted into immunodeficient NSG mice (NOD.Cg-Prkdscid Il2rgtm1Wjl/SzJ) (Jackson Laboratory, USA) for in vivo assay. Liver cholangiocarcinoma LIXFC 2479 (Charles river) tumor cells were obtained from surgical samples post-resection of cancer patients. Tumor fragments were transplanted into immunodeficient mice at passage 1, and were cultured (passaged) as tumor xenografts until a stable growth pattern was established. Tumor fragments were obtained from nude mouse xenografts through successive passages. After being dissected from the donor mice, the tumor was cut into sections (with a peripheral length of 3-4 mm) and placed into PBS containing 10% penicillin/ streptomycin. The sections were then subcutaneously transplanted into one flank of the recipient mouse, which was designated as patient-derived tumor xenograft (PDX) model.

The animals were divided into two groups, each consisting of six mice. Two mice from each group were reconstituted with HSCs from each of the three donors, ensuring similar median tumor volume (50-150 mm$^3$) and weight at the start. The randomization day was set as "Day 0". PBS was used as a control (group 1). Mice in group 2 were treated with 7A6 VH3/Vk5 at a dose of 20 mg/kg. The test substances were administered twice weekly via intraperitoneal injection for four weeks, with tumor size being monitored until the end of the experiment on day 28. Detailed information is presented as shown in FIG. 16, below:

TABLE 16

| Group | Treatment | Dose level [mg/kg] | Dosing volume* [ml/kg] | Dosing days | Route | n = ** |
|---|---|---|---|---|---|---|
| 1 | Vehicle | 10 ml/kg | 10 | BIW x3 | i.p. | 2 + 2 + 2 |
| 2 | 7A6 VH3/Vk5 | 20 mg/kg | 10 | BIW x3 | i.p. | 2 + 2 + 2 |

*based on last body weight measurement
**donor 1 + donor 2 + donor 3
BIW: Bi-weekly(twice a week),
ROA: Route of administration Tumor growth inhibition (ATGI) was calculated as Mean % ΔInhibition:

$$\Delta TGI(\text{Mean \% } \Delta\text{Inhibition}) =$$
$$((\text{mean}(C) - \text{mean}(C0)) - (\text{mean}(T) - \text{mean}(T0)))/$$
$$(\text{mean}(C) - \text{mean}(C0)) * 100\%$$

[T: Size of tumor at the time of measurement for the test group,
T0: Initial tumor size for the test group,
C: Size of the tumor at the time of measurement for the control group,
C0: Initial tumor size for the control group]
The results obtained (tumor size) are presented in FIG. 23. As shown in FIG. 23, the anti-TIGIT 7A6 VH3/Vk5 antibody significantly inhibited tumor growth compared to the control group. For the evaluation of TGI, the tumor sizes between the anti-TIGIT antibody-treated group and the control group were compared on day 28. The tumor growth inhibition ($\Delta$TGI) by the 7A6 VH3/Vk5 antibody was 76.6%, demonstrating that the antibody has significant anti-cancer effects in the liver cancer PDX tumor model, which is considered to have greater physiological relevance to human cancer than synthetic mouse models.

Example 8: Anti-Tumor Efficacy of Anti-Tigit Antibody in Human PBMC and Tumor-Infiltrating T Cells 8.1. TIGIT expression on T cell subset in tumor microenvironment (TME)

To measure the potential effects of the anti-TIGIT antibody in the human tumor microenvironment, TIGIT expression was examined in the liver of HCC (hepatocellular carcinoma) patients and HFE (hemochromatosis) donors. HFE (hemochromatosis) is considered a condition with normal liver function and immunologically healthy. To investigate the expression of TIGIT in T cell subsets, tumor-infiltrating lymphocytes derived from normal donors and HCC cancer patients were prepared (refer to Example 3.1). These cells were stained for cell surface markers (CD3, CD4, CD8, CD127, CD25, TIGIT) (antibodies to CD3, CD4, CD8, CD127, and CD25 were obtained from Bioleg-end, and TIGIT antibody was obtained from R&D Systems), and analyzed via flow cytometry and FlowJo software. The Mean Fluorescence Intensity (MFI) of TIGIT in each T cell subset was measured using FlowJo software (BD Biosci-ences).

The results obtained are presented in FIG. 24. As shown in FIG. 24, TIGIT expression on tumor-infiltrating T cells in HCC patients was higher than in normal donors. Among the tumor-infiltrating T cells in HCC patients, Treg cells expressed TIGIT at a highest level, compared to CD4+ and CD8+ T cells. These findings suggest that Treg cells may be a desirable target for the inhibitory activity of the anti-TIGIT antibody.

8.2. Cytokine Production in T Cells Derived from Liver Cancer Patients

TIGIT-expressing immune cells can cause functional impairment in cancer patients. The ability of the anti-TIGIT antibody treatment to restore or enhance the immune response in HCC patients was tested.

To measure the anti-TIGIT antibody-mediated cytokine production from T cells, human PBMCs obtained from hepatocellular carcinoma (HCC) patients or healthy donors were cultured with anti-CD3 and anti-CD28 antibodies in the presence of the anti-TIGIT 7A6 VH3/Vk5 antibody (10 ug/ml) or the same amount of the reference antibody (anti-TIGIT 10A7, 22G2). Intracellular cytokine production was measured (refer to Example 3.2.2).

The results obtained are presented in FIG. 25. Compared to the reference antibodies, anti-TIGIT antibody 10A7 (Ge-nentech) and 22G2 (BMS), the treatment with the anti-TIGIT 7A6 VH3/Vk5 antibody increased cytokine produc-tion in CD4+ and CD8+ T cells from the PBMCs of HCC patients. Since IL-2 and IFN-$\gamma$ are cytokines have core functions in the immune system, enhancing the proliferation and death activity of NK and T cells, the data obtained shows the efficacy of the anti-TIGIT 7A6 antibody treatment in HCC patients.

8.3. Efficacy of Anti-TIGIT Antibody on T Cells of Lung Cancer Patients

The production of cytokines in immune cells from human PBMCs derived from non-small-cell lung carcinoma (NSCLC) patients was tested upon treatment with anti-TIGIT antibodies (each 10 ug/ml) (refer to Example 3.2.2).

The obtained results are shown in FIG. 26. Compared to the reference antibodies, anti-TIGIT antibody 10A7 (Genen-tech) and 22G2 (BMS), the anti-TIGIT 7A6 VH3/Vk5 antibody increased cytokine production from CD4+ and CD8+ T cells in PBMCs of NSCLC patients to a higher level. These results confirm the efficacy of the anti-TIGIT 7A6 antibody in NSCLC patients.

8.4. Efficacy of Anti-TIGIT Antibody on T Cells of Col-orectal Cancer Patients

TIGIT-expressing immune cells induce functional impair-ments in cancer patients, and an examination was made to investigate whether the treatment with anti-TIGIT antibody could restore or enhance the immune response of colorectal cancer patients. The production of cytokines in immune cells from human PBMCs derived from colorectal cancer (CRC) patients was tested upon treatment with anti-TIGIT antibody (each 10 ug/ml) (refer to Example 3.2.2).

The obtained results are shown in FIG. 27. Compared to the reference antibodies, anti-TIGIT antibody 10A7 (Genen-tech) and 22G2 (BMS), the anti-TIGIT 7A6 VH3/Vk5 antibody increased cytokine production from CD4+ and CD8+ T cells in PBMCs of colorectal cancer patients to a higher level. These results suggest the efficacy of the anti-TIGIT 7A6 antibody in colorectal cancer patients.

Example 9: Assay for T Cell Activation Through Inhibition of Tigit-PVR Interaction by Anti-Tigit Fab Fragment 9.1. Immunological Effects of Anti-TIGIT Fab on Central Memory T Cells and Effector Memory T Cells To verify the specific blocking effect of the anti-TIGIT 7A6 VH3/Vk5 antibody on the TIGIT/PVR pathway, the anti-TIGIT-Fab fragment (disulfide linkage between 7A6_VH3 variable region and 7A6_VK5 variable region) of the antibody was produced in HEK293 cells and purified using Immobilized metal affinity chromatography. The anti-TIGIT Fab fragment was used to exhibit only the specific blocking function without Fc-induced effects.

The activation of central memory T cells [Tcm] (FIG. 28a) and effector memory T cells [Tem] (FIG. 28b) was examined through specific binding of the anti-TIGIT Fab fragment to the TIGIT protein, which provides long-term potent cytotoxic protection against cancer. Specifically, 500, 000 PBMC cells were activated with anti-CD3 (0.2 ug/ml) (BD Biosciences) and anti-CD28 antibodies (1 ug/ml) (BD Biosciences), and then treated with the anti-TIGIT Fab fragment (10 ug/ml) for 48 hours. Brefeldin A (Sigma) and Monensin (Sigma) were added to each well to a final concentration of 1/1000 and incubated for an additional 4 hours. The central memory T cells and effector memory T cells were stained. In this regard, the cells were washed and stained at room temperature for 10 minutes with the follow-ing antibodies: Alive/Dead (ThermoFisher LIVE/DEAD™ Fixable Near-IR Dead Cell Stain Kit, for 633 or 635 nm excitation), Anti-CD3-APC (Biolegend), Anti-CD8-PerCP (Biolegend), Anti-CD45RA-Brillant Violet 421 (Biolegend), Anti-CCR7-Brilliant Violet 510 (Biolegend). After staining, the cytokine levels in central memory and effector memory T cells were measured as follows. Cells were fixed and permeabilized using the Foxp3/Transcription Factor Fixa-tion/Permeabilization Concentrate and Diluent kit (Ther-moFisher) according to the manufacturer's instructions. The cells were stained with fluorophore-conjugated antibodies against intracellular IL-2, IFN$\gamma$, and TNFa (all from Biolegend). The cells were analyzed by flow cytometry (Cyto-FLEX, Beckman Coulter), and the data were analyzed using FlowJo software (BD Biosciences).

The obtained results are shown in FIGS. 28*a* (central memory T cells) and 28*b* (effector memory T cells). As understood from the results, the anti-TIGIT-Fab fragment induced enhanced activation levels of Tcm and Tem, demonstrating that the anti-TIGIT (7A6 VH3/Vk5) antibody mediates a specific blocking activity that facilitates long-lasting immune responses against cancer.

9.2. Anti-TIGIT Fab Fragment-Mediated Stimulation of Cytotoxicity against A375 Tumor Cells A375 tumor cells (35 k cells/well) were stained with Syto-9 dye and co-cultured with PBMC and CytoStim (1/50) in the presence of the Fab fragment generated from the humanized anti-TIGIT antibody (Fab 7A6 VH0/Vk0, 3VH3/Vk5, VH4/Vk4) (each 10ug/ml). The tumor cells were counted using the Incucyte® Live-Cell analysis system (Sartorius).

The results are shown in FIG. 29. All tested anti-TIGIT Fab fragments VH0/VK0, VH3/Vk5, and VH4/Vk4 blocked the TIGIT-CD155 (PVR) interaction and increased cytotoxicity against A375 tumor cells. These results confirm that the humanized anti-TIGIT 7A6 antibody effectively blocks the TIGIT-CD155 (PVR) pathway and induces enhanced immune function.

Example 10: Immunomodulatory Effects of Anti-Tigit Antibody on Regulatory T Cells and NK Cells 10.1. High-level Expression of TIGIT on Regulatory T Cells (Tregs)

Markers for T cell subsets and TIGIT protein from the PBMCs of a healthy donor were stained (Anti-CD3-APC (Biolegend), Alive/Dead (ThermoFisher LIVE/DEAD™ Fixable Near-IR Dead Cell Stain Kit), Anti-CD8-PerCP (Biolegend), Anti-CD4-Alexa Fluor700 (Biolegend), Anti-CD127-PE (Biolegend), Anti-CD25-Brilliant Violet 421 (Biolegend), and Anti-TIGIT-PeCy7 (Biolegend)). After staining, the cells were spun down and analyzed by flow cytometry.

The results are depicted in FIG. 30. TIGIT was expressed at a higher level in regulatory T cells (Tregs) compared to non-Tregs CD4+ and CD8+ T cells.

10.2. Treg Depletion Activity of Anti-TIGIT 7A6 VH3/Vk5 Antibody

The anti-TIGIT 7A6 VH3/Vk5 antibody (10 ug/ml) was co-cultured with human PBMCs in the presence of anti-CD3 antibody (BD Biosciences) and anti-CD28 antibody (BD Biosciences). The anti-TIGIT 10A7 (Genentech) was used as a control. The frequency of Tregs, CD4+ T, and CD8+ T cells was assessed by flow cytometry.

The obtained results are depicted in FIGS. 31*a* (Tregs), 31*b* (CD4+ T cells), 31*c* (CD8+ T cells), and 31*d*. The anti-TIGIT 7A6 VH3/Vk5 antibody specifically targeted Treg cells without altering the ratio of CD4+ and CD8+ T cells. Moreover, the anti-TIGIT antibody depleted Tregs at a higher level, compared to the control anti-TIGIT antibody (10A7) (FIG. 31*d*).

10.3. NK Cell-Mediated Treg Depletion Activity of Anti-TIGIT 7A6 VH3/Vk5 antibody Tregs and NK cells were co-cultured overnight in the presence or absence of the anti-TIGIT antibody 7A6 VH3/Vk5 or VH3/Vk5-DLE (each 10 ug/ml). On the next day, the remaining Tregs and NK cells were counted by flow cytometry. Treg cells and NK cells were isolated from human PBMCs using the Miltenyi kits (CD4+ CD25+ CD127-dim reg T cell isolation kit II, cat no. 130-094-775) and Miltenyi kits (NK Cell Isolation Kit, cat no. 130-092-657), respectively, according to the manufacturer's instructions.

The results obtained are shown in FIG. 32. The number of Treg cells decreased upon treatment with the anti-TIGIT 7A6VH3/Vk5 antibody and the VH3/VK5-DLE antibody, while the number of NK cells remained unchanged. These results indicate that the tested anti-TIGIT antibody efficiently depletes Tregs via antibody-dependent cellular cyto-toxicity in conjunction with NK cells.

Also, an examination was made to see whether Fc receptor binding is necessary for NK cell-mediated Treg depletion by the anti-TIGIT antibody.

Tregs and NK cells were co-cultured overnight in the presence of anti-TIGIT antibody 7A6 VH3/Vk5-DLE (10 ug/ml). Treg cells and NK cells were isolated from human PBMCs using the Miltenyi kits (CD4+ CD25+ CD127-dim reg T cell isolation kit II, cat no. 130-094-775) and Miltenyi kits (NK Cell Isolation Kit, cat no. 130-092-657), respectively, according to the manufacturer's instructions. Fc receptors were blocked using Fc blocking antibodies CD16 and Human TruStain FcX™ (BioLegend). On the next day, the remaining Tregs and NK cells were counted by flow cytometry.

The results obtained are shown in FIG. 33. The anti-TIGIT antibody significantly reduced Tregs, and this reduction was inhibited when the FcR was blocked by blocking antibodies. These results indicate that Fc receptor binding is necessary for NK cell-mediated Treg depletion by the anti-TIGIT antibody.

10.4. Fc-Dependent T Cell Activation

The production of cytokines in human T cells (CD4+ T cells and CD8+ T cells) was measured either with or without pre-blocking of FcgRIIIA. Five hundred thousand PBMC cells were pre-incubated at room temperature for 5 minutes with the FcgRIIIA antibody (Biolegend cat no. 422302). The PBMC cells were then cultured with 0.2 ug/ml anti-CD3 (BD Biosciences) and 1 ug/ml anti-CD28 (BD Biosciences) monoclonal antibodies in the presence of anti-TIGIT 7A6VH3/Vk5 (10 ug/ml) or isotype control antibody (10 ug/ml). After culturing, cells were spun down at 400×g for 10 minutes at 4° C., and the intracellular cytokine concentrations in T cells were measured. In this regard, cells were stained with the Zombie Aqua fixable dead cell dye solution (Biolegend) and labeled with fluorophore-conjugated anti-bodies (Biolgend) against CD3, CD4, and CD8+ cell surface markers for CD4+ and CD8+ T cells for 30 minutes on ice. Cells were fixed and permeabilized using the eBioscience™ Foxp3/Transcription Factor Fixation/Permeabilization Concentrate and Diluent kit (ThermoFisher) according to the manufacturer's instructions. The cells were stained with fluorophore-conjugated antibodies against intracellular IL-2 (Biolegend) and IFNγ (Biolegend). The cells were then analyzed using a flow cytometer (CytoFLEX, Beckman Coulter), and the data was analyzed using FlowJo software (BD Biosciences).

The results obtained are depicted in FIGS. 34*a* (CD4+ T cells) and 34*b* (CD8+ T cells). Blocking of FcgRIIIA significantly reduced cytokine production in both CD4+ and CD8+ T cells, suggesting that the anti-TIGIT antibody requires FcgR interaction for T cell activation and Treg depletion. The anti-TIGIT antibody demonstrated enhanced T cell responses through FcgR engagement.

Statistics

Statistical significance was evaluated using GraphPad Prism 9 software (GraphPad Software, USA) through ordinary one-way ANOVA, paired, and unpaired Student's tests. Data are presented as mean±SEM. **$p<0.0001$, *$p<0.001$, **$p<0.01$, *$p<0.05$, ns=not significant, as stated in figure legends.

The invention claimed is:

1. An anti-TIGIT antibody or an antigen-binding fragment thereof, wherein the anti-TIGIT antibody comprises:
- a polypeptide comprising the amino acid sequence of SEQ ID NO: 1 (CDR-H1),
- a polypeptide comprising the amino acid sequence of SEQ ID NO: 2 (CDR-H2),
- a polypeptide comprising the amino acid sequence of SEQ ID NO: 3 (CDR-H3),
- a polypeptide comprising the amino acid sequence of SEQ ID NO: 4 (CDR-L1),
- a polypeptide comprising the amino acid sequence of SEQ ID NO: 5 (CDR-L2), and
- a polypeptide comprising the amino acid sequence of SEQ ID NO: 6 (CDR-L3).

2. The anti-TIGIT antibody or antigen-binding fragment thereof according to claim 1, wherein the anti-TIGIT antibody comprises:
- a polypeptide comprising the amino acid sequence of SEQ ID NO: 1 (CDR-H1),
- a polypeptide comprising the amino acid sequence of SEQ ID NO: 2 (CDR-H2),
- a polypeptide comprising the amino acid sequence of SEQ ID NO: 3 (CDR-H3),
- a polypeptide comprising the amino acid sequence of SEQ ID NO: 7 or 8 (CDR-L1),
- a polypeptide comprising the amino acid sequence of SEQ ID NO: 5 (CDR-L2), and

- a polypeptide comprising the amino acid sequence of SEQ ID NO: 6 (CDR-L3).

3. The anti-TIGIT antibody or antigen-binding fragment thereof according to claim 1, wherein the anti-TIGIT antibody comprises:
- a heavy chain variable region comprising the amino acid sequence of SEQ ID NO: 9, 10, 11, 12, 13, or 14, and
- a light chain variable region comprising the amino acid sequence of SEQ ID NO: 15, 16, 17, 18, 19, or 20.

4. The anti-TIGIT antibody or antigen-binding fragment thereof according to claim 1, wherein the anti-TIGIT antibody or antigen-binding fragment thereof binds to at least one amino acid selected from the amino acids at positions 51-70 in the amino acid sequence of TIGIT protein, and the amino acids at positions 51-70 are represented by SEQ ID NO: 31.

5. The anti-TIGIT antibody or antigen-binding fragment thereof according to claim 1, wherein the anti-TIGIT antibody is an animal antibody, a chimeric antibody, or a humanized antibody.

6. The anti-TIGIT antibody or antigen-binding fragment thereof according to claim 1, wherein the antigen-binding fragment is scFv, scFv-Fc, (scFv)2, Fab, Fab', or F(ab')2 of the anti-TIGIT antibody.

7. A pharmaceutical composition for prevention or treatment of cancer, the composition comprising the anti-TIGIT antibody or antigen-binding fragment thereof according to claim 1.

8. The pharmaceutical composition according to claim 7, wherein the cancer is solid cancer or hematologic cancer.

9. The pharmaceutical composition according to claim 7, further comprising a drug targeting PD-1, PD-L1, or both of them.

10. A pharmaceutical composition for immunopotentiation, the composition comprising the anti-TIGIT antibody or antigen-binding fragment thereof according to claim 1.

11. The pharmaceutical composition according to claim 10, wherein the composition further comprises a drug targeting PD-1, PD-L1, or both of them.

12. A pharmaceutical composition for prevention or treatment of an infectious disease, the composition comprising the anti-TIGIT antibody or antigen-binding fragment thereof according to claim 1.

13. The pharmaceutical composition for prevention or treatment of an infectious disease according to claim 12, wherein the infectious disease is an infection of virus, bacteria, fungi, or parasite, or a disease caused by the infection.

14. The pharmaceutical composition for prevention or treatment of an infectious disease according to claim 12, further comprises a drug targeting PD-1, PD-L1, or both of them.

15. A method of prevention or treatment of cancer in a subject, comprising administering a pharmaceutically effective amount of the anti-TIGIT antibody or antigen-binding fragment thereof according to claim 1 to the subject.

16. The method according to claim 15, further comprising administering a drug targeting PD-1, PD-L1, or both of them to the subject.

17. A method of immunopotentiation in a subject, comprising administering a pharmaceutically effective amount of the anti-TIGIT antibody or antigen-binding fragment thereof according to claim 1 to the subject.

18. The method according to claim 17, further comprising administering a drug targeting PD-1, PD-L1, or both of them to the subject.

19. A method of prevention or treatment of an immune-related disease in a subject, comprising administering a pharmaceutically effective amount of the anti-TIGIT antibody or antigen-binding fragment thereof according to claim 1 to the subject, wherein the immune-related disease is an infectious disease or an inflammatory disease.

20. The method according to claim 19, further comprising administering a drug targeting PD-1, PD-L1, or both of them to the subject.

* * * * *